United States Patent
Bharadwaj et al.

(10) Patent No.: US 10,544,413 B2
(45) Date of Patent: Jan. 28, 2020

(54) METHODS AND SYSTEMS FOR SORTING DROPLETS AND BEADS

(71) Applicant: 10X Genomics, Inc., Pleasanton, CA (US)

(72) Inventors: Rajiv Bharadwaj, Pleasanton, CA (US); Michael Schnall-Levin, San Francisco, CA (US); Anthony Makarewicz, Livermore, CA (US); Steven Short, Pleasanton, CA (US)

(73) Assignee: 10X Genomics, Inc., Pleasanton, CA (US)

( * ) Notice: Subject to any disclaimer, the term of this patent is extended or adjusted under 35 U.S.C. 154(b) by 0 days.

(21) Appl. No.: 16/031,880

(22) Filed: Jul. 10, 2018

(65) Prior Publication Data

US 2018/0334670 A1 Nov. 22, 2018

Related U.S. Application Data

(63) Continuation of application No. PCT/US2018/033280, filed on May 17, 2018.

(60) Provisional application No. 62/508,219, filed on May 18, 2017.

(51) Int. Cl.
| | |
|---|---|
| *C12N 15/10* | (2006.01) |
| *G01N 15/14* | (2006.01) |
| *B01L 3/00* | (2006.01) |
| *G01N 21/64* | (2006.01) |
| *C12Q 1/6806* | (2018.01) |
| *G01N 15/10* | (2006.01) |
| *C12Q 1/6834* | (2018.01) |

(52) U.S. Cl.
CPC .... *C12N 15/1065* (2013.01); *B01L 3/502715* (2013.01); *B01L 3/502761* (2013.01); *B01L 3/502784* (2013.01); *C12N 15/1075* (2013.01); *C12Q 1/6806* (2013.01); *G01N 15/1031* (2013.01); *G01N 15/1056* (2013.01); *G01N 15/1404* (2013.01); *G01N 15/1484* (2013.01); *G01N 21/6428* (2013.01); *B01L 2200/0652* (2013.01); *B01L 2200/0673* (2013.01); *B01L 2300/0867* (2013.01); *B01L 2400/043* (2013.01); *B01L 2400/0415* (2013.01); *B01L 2400/086* (2013.01); *C12N 15/1006* (2013.01); *C12Q 1/6834* (2013.01); *C12Q 2563/149* (2013.01); *C12Q 2563/179* (2013.01); *C12Q 2565/629* (2013.01); *G01N 2015/1006* (2013.01); *G01N 2015/1081* (2013.01); *G01N 2015/149* (2013.01)

(58) Field of Classification Search
None
See application file for complete search history.

(56) References Cited

U.S. PATENT DOCUMENTS

| | | |
|---|---|---|
| 5,700,692 A | 12/1997 | Sweet |
| 5,837,200 A | 11/1998 | Diessel et al. |
| 6,057,149 A | 5/2000 | Burns et al. |
| 6,123,798 A | 9/2000 | Gandhi et al. |
| 6,176,962 B1 | 1/2001 | Soane et al. |
| 6,177,479 B1 | 1/2001 | Nakajima et al. |
| 6,281,018 B1 | 8/2001 | Kirouac et al. |
| 6,778,724 B2 | 8/2004 | Wang et al. |
| 6,808,075 B2 | 10/2004 | Bohm et al. |
| 6,877,528 B2 | 4/2005 | Gilbert et al. |
| 6,915,679 B2 | 7/2005 | Chien et al. |
| 6,976,590 B2 | 12/2005 | Deshpande et al. |
| 6,994,218 B2 | 2/2006 | Kawano et al. |
| 7,104,405 B2 | 9/2006 | Bohm et al. |
| 7,241,988 B2 | 7/2007 | Gruber et al. |
| 7,264,972 B2 | 9/2007 | Foster |
| 7,452,725 B2 | 11/2008 | Leary et al. |
| 7,569,788 B2 | 8/2009 | Deshpande et al. |
| 7,584,857 B2 | 9/2009 | Bohm et al. |
| 7,622,076 B2 | 11/2009 | Davies et al. |
| 7,699,767 B2 | 4/2010 | Mueth et al. |
| 7,704,395 B2 | 4/2010 | Mueth et al. |
| 7,723,116 B2 | 5/2010 | Evans et al. |
| 7,767,444 B2 | 8/2010 | Liu et al. |
| 7,772,287 B2 | 8/2010 | Higuchi et al. |
| 7,901,947 B2 | 3/2011 | Pollack et al. |

(Continued)

FOREIGN PATENT DOCUMENTS

| | | |
|---|---|---|
| GB | 2097692 A | 11/1982 |
| WO | WO-2004/002627 A2 | 1/2004 |

(Continued)

OTHER PUBLICATIONS

Klein et al.( Cell 161.5 (2015): 1187-1201.). (Year: 2015).*

(Continued)

*Primary Examiner* — Tracy Vivlemore
*Assistant Examiner* — Sahana S Kaup
(74) *Attorney, Agent, or Firm* — Clark & Elbing LLP

(57) ABSTRACT

Methods and systems for sorting droplets are provided. In some cases, occupied droplets may be sorted from unoccupied droplets. In some cases, singularly occupied droplets may be sorted from unoccupied droplets and multiply occupied droplets. Methods and systems for sorting cell beads are provided. In some cases, cell beads may be sorted from particles unoccupied with cell derivatives. In some cases, singularly occupied cell beads may be sorted from unoccupied particles and multiply occupied cell beads. Methods and systems for selectively polymerizing droplets based on occupancy and size of the droplets are provided.

30 Claims, 20 Drawing Sheets

(56) References Cited

U.S. PATENT DOCUMENTS

| | | |
|---|---|---|
| 7,927,797 B2 | 4/2011 | Nobile et al. |
| 7,943,671 B2 | 5/2011 | Herminghaus et al. |
| 7,963,399 B2 | 6/2011 | Bohm et al. |
| 8,029,744 B2 | 10/2011 | Noda et al. |
| 8,096,421 B2 | 1/2012 | Shinoda |
| 8,186,913 B2 | 5/2012 | Toner et al. |
| 8,198,092 B2 | 6/2012 | Durack et al. |
| 8,241,914 B2 | 8/2012 | Durack et al. |
| 8,246,805 B2 | 8/2012 | Shinoda |
| 8,298,767 B2 | 10/2012 | Brenner et al. |
| 8,387,803 B2 | 3/2013 | Thorslund et al. |
| 8,408,399 B2 | 4/2013 | Bohm et al. |
| 8,454,906 B2 | 6/2013 | Mathies et al. |
| 8,467,040 B2 | 6/2013 | Luscher |
| 8,524,173 B2 | 9/2013 | Yamanaka et al. |
| 8,529,026 B2 | 9/2013 | Clarke et al. |
| 8,563,274 B2 | 10/2013 | Brenner et al. |
| 8,567,608 B2 | 10/2013 | Deshpande et al. |
| 8,592,221 B2 | 11/2013 | Fraden et al. |
| 8,609,422 B2 | 12/2013 | Durack et al. |
| 8,613,890 B2 | 12/2013 | Muraki |
| 8,633,015 B2 | 1/2014 | Ness et al. |
| 8,658,368 B2 | 2/2014 | Quake et al. |
| 8,658,430 B2 | 2/2014 | Miller et al. |
| 8,679,756 B1 | 3/2014 | Brenner et al. |
| 8,741,192 B2 | 6/2014 | Torii et al. |
| 8,795,500 B2 | 8/2014 | Shinoda |
| 8,807,879 B2 | 8/2014 | Toner et al. |
| 8,820,538 B1 | 9/2014 | Lin |
| 8,821,006 B2 | 9/2014 | Norikane et al. |
| 8,857,462 B2 | 10/2014 | Miller et al. |
| 8,871,500 B2 | 10/2014 | Foster et al. |
| 8,944,083 B2 | 2/2015 | Collier et al. |
| 8,986,628 B2 | 3/2015 | Stone et al. |
| 9,012,390 B2 | 4/2015 | Holtze et al. |
| 9,017,623 B2 | 4/2015 | Fraden et al. |
| 9,089,844 B2 | 7/2015 | Hiddessen et al. |
| 9,102,980 B2 | 8/2015 | Brenner et al. |
| 9,108,173 B2 | 8/2015 | Lee et al. |
| 9,126,160 B2 | 9/2015 | Ness et al. |
| 9,132,394 B2 | 9/2015 | Makarewicz, Jr. et al. |
| 9,133,009 B2 | 9/2015 | Baroud et al. |
| 9,156,010 B2 | 10/2015 | Colston, Jr. et al. |
| 9,194,861 B2 | 11/2015 | Hindson et al. |
| 9,207,160 B2 | 12/2015 | Shinoda |
| 9,216,392 B2 | 12/2015 | Hindson et al. |
| 9,248,417 B2 | 2/2016 | Hindson et al. |
| 9,266,104 B2 | 2/2016 | Link |
| 9,273,308 B2 | 3/2016 | Link et al. |
| 9,328,376 B2 | 5/2016 | Hiddessen et al. |
| 9,339,850 B2 | 5/2016 | Deshpande et al. |
| 9,388,465 B2 | 7/2016 | Hindson et al. |
| 9,393,560 B2 | 7/2016 | Ness et al. |
| 9,399,215 B2 | 7/2016 | Cauley, III et al. |
| 9,403,294 B2 | 8/2016 | Cauley, III |
| 9,409,174 B2 | 8/2016 | Makarewicz, Jr. et al. |
| 9,410,149 B2 | 8/2016 | Brenner et al. |
| 9,410,150 B2 | 8/2016 | Brenner et al. |
| 9,410,201 B2 | 8/2016 | Hindson et al. |
| 9,417,190 B2 | 8/2016 | Hindson et al. |
| 9,427,737 B2 | 8/2016 | Heredia et al. |
| 9,486,757 B2 | 11/2016 | Romanowsky et al. |
| 9,492,797 B2 | 11/2016 | Makarewicz et al. |
| 9,500,664 B2 | 11/2016 | Ness et al. |
| 9,527,049 B2 | 12/2016 | Hiddessen et al. |
| 9,562,837 B2 | 2/2017 | Link |
| 9,567,631 B2 | 2/2017 | Hindson et al. |
| 9,623,384 B2 | 4/2017 | Hindson et al. |
| 9,638,620 B2 | 5/2017 | Di Carlo et al. |
| 9,644,204 B2 | 5/2017 | Hindson et al. |
| 9,683,792 B2 | 6/2017 | Possinger et al. |
| 9,687,848 B2 | 6/2017 | Makarewicz, Jr. et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,700,891 B2 | 7/2017 | Smith et al. |
| 9,701,998 B2 | 7/2017 | Hindson et al. |
| 9,702,808 B2 | 7/2017 | Lin |
| 9,764,322 B2 | 9/2017 | Hiddessen et al. |
| 9,824,068 B2 | 11/2017 | Wong |
| 9,856,530 B2 | 1/2018 | Hindson et al. |
| 9,946,577 B1 | 4/2018 | Stafford et al. |
| 9,951,386 B2 | 4/2018 | Hindson et al. |
| 9,975,122 B2 | 5/2018 | Masquelier et al. |
| 10,071,377 B2 | 9/2018 | Bharadwaj et al. |
| 10,137,449 B2 | 11/2018 | Bharadwaj et al. |
| 10,150,117 B2 | 12/2018 | Bharadwaj et al. |
| 2002/0058332 A1 | 5/2002 | Quake et al. |
| 2002/0127736 A1 | 9/2002 | Chou et al. |
| 2003/0228610 A1 | 12/2003 | Seul |
| 2004/0068019 A1 | 4/2004 | Higuchi et al. |
| 2004/0109793 A1 | 6/2004 | McNeely et al. |
| 2005/0103690 A1 | 5/2005 | Kawano et al. |
| 2005/0249636 A1 | 11/2005 | Tacklind et al. |
| 2005/0266582 A1 | 12/2005 | Modlin et al. |
| 2006/0078888 A1 | 4/2006 | Griffiths et al. |
| 2006/0078893 A1 | 4/2006 | Griffiths et al. |
| 2007/0065808 A1 | 3/2007 | Bohm et al. |
| 2007/0117086 A1 | 5/2007 | Evans et al. |
| 2007/0166200 A1 | 7/2007 | Zhou et al. |
| 2007/0196397 A1 | 8/2007 | Torii et al. |
| 2008/0003142 A1* | 1/2008 | Link .................. B01F 3/0807 422/82.08 |
| 2008/0038810 A1 | 2/2008 | Pollack et al. |
| 2008/0050283 A1 | 2/2008 | Chou et al. |
| 2008/0053205 A1 | 3/2008 | Pollack et al. |
| 2008/0056948 A1 | 3/2008 | Dale et al. |
| 2008/0138876 A1 | 6/2008 | Ragsdale |
| 2008/0166720 A1 | 7/2008 | Hsieh et al. |
| 2008/0295909 A1 | 12/2008 | Locascio et al. |
| 2009/0012187 A1 | 1/2009 | Chu et al. |
| 2009/0035770 A1 | 2/2009 | Mathies et al. |
| 2009/0047713 A1 | 2/2009 | Handique |
| 2009/0131543 A1 | 5/2009 | Weitz et al. |
| 2009/0155563 A1 | 6/2009 | Petsev et al. |
| 2009/0235990 A1 | 9/2009 | Beer |
| 2009/0269248 A1 | 10/2009 | Falb et al. |
| 2009/0269824 A1 | 10/2009 | Kim et al. |
| 2009/0325217 A1 | 12/2009 | Luscher |
| 2010/0006441 A1 | 1/2010 | Renaud et al. |
| 2010/0022414 A1 | 1/2010 | Link et al. |
| 2010/0022680 A1 | 1/2010 | Karnik et al. |
| 2010/0105866 A1 | 4/2010 | Fraden et al. |
| 2010/0163109 A1 | 7/2010 | Fraden et al. |
| 2010/0184928 A1 | 7/2010 | Kumacheva |
| 2010/0216208 A1 | 8/2010 | Mueth et al. |
| 2011/0005978 A1 | 1/2011 | Bohm et al. |
| 2011/0053798 A1 | 3/2011 | Hindson et al. |
| 2011/0086377 A1 | 4/2011 | Thwar et al. |
| 2011/0223314 A1 | 9/2011 | Zhang et al. |
| 2011/0267457 A1 | 11/2011 | Weitz et al. |
| 2012/0015382 A1 | 1/2012 | Weitz et al. |
| 2012/0091059 A1 | 4/2012 | Beer et al. |
| 2012/0121480 A1 | 5/2012 | Frenz et al. |
| 2012/0122714 A1 | 5/2012 | Samuels et al. |
| 2012/0142018 A1 | 6/2012 | Jiang |
| 2012/0196288 A1* | 8/2012 | Beer .................. B01L 3/502761 435/6.12 |
| 2012/0199226 A1 | 8/2012 | Weitz et al. |
| 2012/0211084 A1 | 8/2012 | Weitz et al. |
| 2012/0219947 A1 | 8/2012 | Yurkovetsky et al. |
| 2012/0220494 A1* | 8/2012 | Samuels ............ C12N 15/1075 506/16 |
| 2012/0222748 A1 | 9/2012 | Weitz et al. |
| 2012/0231444 A1 | 9/2012 | Quake et al. |
| 2012/0236299 A1 | 9/2012 | Chiou et al. |
| 2012/0301869 A1 | 11/2012 | Evans |
| 2012/0315690 A1 | 12/2012 | Di Carlo et al. |
| 2013/0046030 A1 | 2/2013 | Rotem et al. |
| 2013/0059310 A1 | 3/2013 | Brenner et al. |
| 2013/0064776 A1 | 3/2013 | El Harrak et al. |
| 2013/0084572 A1 | 4/2013 | Hindson et al. |
| 2013/0109575 A1 | 5/2013 | Kleinschmidt et al. |
| 2013/0130919 A1 | 5/2013 | Chen et al. |

(56) References Cited

U.S. PATENT DOCUMENTS

| | | |
|---|---|---|
| 2013/0149737 A1 | 6/2013 | Seidel et al. |
| 2013/0203172 A1 | 8/2013 | Wex et al. |
| 2013/0236901 A1 | 9/2013 | Potier et al. |
| 2013/0281316 A1 | 10/2013 | Ismagilov et al. |
| 2013/0337575 A1 | 12/2013 | Fox et al. |
| 2014/0024023 A1 | 1/2014 | Cauley, III et al. |
| 2014/0080226 A1 | 3/2014 | Cauley, III et al. |
| 2014/0087412 A1 | 3/2014 | Fouras et al. |
| 2014/0155295 A1 | 6/2014 | Hindson et al. |
| 2014/0161685 A1 | 6/2014 | Lee et al. |
| 2014/0179544 A1 | 6/2014 | Steenblock et al. |
| 2014/0199730 A1 | 7/2014 | Agresti et al. |
| 2014/0220350 A1 | 8/2014 | Kim et al. |
| 2014/0221239 A1 | 8/2014 | Carman et al. |
| 2014/0235506 A1 | 8/2014 | Hindson et al. |
| 2014/0272996 A1 | 9/2014 | Bemis |
| 2014/0273198 A1 | 9/2014 | Saito et al. |
| 2014/0273201 A1 | 9/2014 | Saito et al. |
| 2014/0273202 A1 | 9/2014 | Saito et al. |
| 2014/0287963 A1 | 9/2014 | Hindson et al. |
| 2014/0312534 A1 | 10/2014 | Cauley, III |
| 2014/0326339 A1 | 11/2014 | Toner et al. |
| 2014/0338753 A1 | 11/2014 | Sperling et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0017648 A1 | 1/2015 | Hiddessen et al. |
| 2015/0031034 A1 | 1/2015 | Hindson et al. |
| 2015/0034163 A1 | 2/2015 | Abate et al. |
| 2015/0050688 A1 | 2/2015 | Thrasher et al. |
| 2015/0066385 A1 | 3/2015 | Schnall-Levin et al. |
| 2015/0224466 A1 | 8/2015 | Hindson et al. |
| 2015/0258543 A1 | 9/2015 | Baroud et al. |
| 2015/0267246 A1 | 9/2015 | Baroud et al. |
| 2015/0292988 A1 | 10/2015 | Bharadwaj et al. |
| 2015/0298091 A1 | 10/2015 | Weitz et al. |
| 2015/0336096 A1 | 11/2015 | Smith et al. |
| 2015/0352597 A1 | 12/2015 | Deshpande et al. |
| 2015/0355071 A1 | 12/2015 | Gluckstad |
| 2015/0360236 A1 | 12/2015 | Garcia et al. |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol et al. |
| 2016/0053303 A1 | 2/2016 | Brenner et al. |
| 2016/0059204 A1 | 3/2016 | Hindson et al. |
| 2016/0091145 A1 | 3/2016 | Weitz et al. |
| 2016/0097087 A1 | 4/2016 | Wiyatno et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0250637 A1 | 9/2016 | Neild et al. |
| 2016/0257984 A1 | 9/2016 | Hardenbol et al. |
| 2016/0271576 A1 | 9/2016 | Arab et al. |
| 2016/0281136 A1 | 9/2016 | Jarosz et al. |
| 2016/0281137 A1 | 9/2016 | Jarosz et al. |
| 2016/0281138 A1 | 9/2016 | Jarosz et al. |
| 2016/0281160 A1 | 9/2016 | Jarosz et al. |
| 2016/0281161 A1 | 9/2016 | Jarosz et al. |
| 2016/0299053 A1 | 10/2016 | Jiang |
| 2016/0304860 A1 | 10/2016 | Hindson et al. |
| 2016/0314242 A1 | 10/2016 | Schnall-Levin et al. |
| 2016/0332163 A1 | 11/2016 | Wang et al. |
| 2016/0348093 A1 | 12/2016 | Price et al. |
| 2016/0362724 A1 | 12/2016 | Bailey et al. |
| 2017/0009274 A1 | 1/2017 | Abate et al. |
| 2017/0014824 A1 | 1/2017 | Boyd et al. |
| 2017/0016041 A1 | 1/2017 | Greenfield et al. |
| 2017/0028365 A1 | 2/2017 | Link et al. |
| 2017/0056884 A1 | 3/2017 | Hiddessen et al. |
| 2017/0065979 A1 | 3/2017 | Ness et al. |
| 2017/0080425 A1 | 3/2017 | Toner et al. |
| 2017/0106134 A1 | 4/2017 | Dreschel et al. |
| 2017/0114385 A1 | 4/2017 | Di Carlo et al. |
| 2017/0122861 A1 | 5/2017 | Lin |
| 2017/0128937 A1 | 5/2017 | Hung et al. |
| 2017/0128938 A9 | 5/2017 | Gilbert et al. |
| 2017/0128940 A1 | 5/2017 | Amini et al. |
| 2017/0128943 A1 | 5/2017 | Fraden et al. |
| 2017/0136461 A1 | 5/2017 | Smith et al. |
| 2017/0144161 A1 | 5/2017 | Hindson et al. |
| 2017/0145476 A1 | 5/2017 | Ryvkin et al. |
| 2017/0151536 A1 | 6/2017 | Weitz et al. |
| 2017/0159109 A1 | 6/2017 | Zheng et al. |
| 2017/0165663 A1 | 6/2017 | Hong et al. |
| 2017/0175179 A1 | 6/2017 | Hiddessen et al. |
| 2017/0235876 A1 | 8/2017 | Jaffe et al. |
| 2017/0246638 A1 | 8/2017 | Possinger et al. |
| 2017/0260584 A1 | 9/2017 | Zheng et al. |
| 2017/0282145 A1 | 10/2017 | Merten et al. |
| 2017/0291174 A1 | 10/2017 | Makarewicz, Jr. et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0056294 A1 | 3/2018 | Di Carlo et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0094313 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0142292 A1 | 5/2018 | Hindson et al. |
| 2018/0236443 A1 | 8/2018 | Masquelier et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0060906 A1 | 2/2019 | Bharadwaj et al. |
| 2019/0064173 A1 | 2/2019 | Bharadwaj et al. |

FOREIGN PATENT DOCUMENTS

| | | | |
|---|---|---|---|
| WO | WO-2004/091763 A2 | 10/2004 | |
| WO | WO-2006/040551 A2 | 4/2006 | |
| WO | WO-2007140015 A2 * | 12/2007 | ........ B01L 3/502784 |
| WO | WO-2008/121342 A2 | 10/2008 | |
| WO | WO-2010/104604 A1 | 9/2010 | |
| WO | WO-2010128858 A1 | 11/2010 | |
| WO | WO-2012/013316 A1 | 2/2012 | |
| WO | WO-2012/142664 A1 | 10/2012 | |
| WO | WO-2012156744 A2 * | 11/2012 | ......... C12N 15/1075 |
| WO | WO-2012/167142 A2 | 12/2012 | |
| WO | WO-2013/096643 A1 | 6/2013 | |
| WO | WO-2013/112121 A1 | 8/2013 | |
| WO | WO-2014/028378 A2 | 2/2014 | |
| WO | WO-2014/117784 A1 | 8/2014 | |
| WO | WO-2014/165559 A2 | 10/2014 | |
| WO | WO-2014/210353 A2 | 12/2014 | |
| WO | WO-2015/015199 A2 | 2/2015 | |
| WO | WO-2015/076251 A1 | 5/2015 | |
| WO | WO-2015/132317 A1 | 9/2015 | |
| WO | WO-2015/132318 A1 | 9/2015 | |
| WO | WO-2015/134984 A1 | 9/2015 | |
| WO | WO-2015/157567 A1 | 10/2015 | |
| WO | WO-2015/160919 A1 | 10/2015 | |
| WO | WO-2015/164212 A1 | 10/2015 | |
| WO | WO-2015/191534 A2 | 12/2015 | |

(56) References Cited

FOREIGN PATENT DOCUMENTS

| WO | WO-2015/200869 A1 | 12/2015 |
|---|---|---|
| WO | WO-2015/200871 A1 | 12/2015 |
| WO | WO-2015/200893 A2 | 12/2015 |
| WO | WO-2016/035284 A1 | 3/2016 |
| WO | WO-2016/065056 A1 | 4/2016 |
| WO | WO-2016/069939 A1 | 5/2016 |
| WO | WO-2016/075172 A1 | 5/2016 |
| WO | WO-2016/085742 A1 | 6/2016 |
| WO | WO-2016/087068 A1 | 6/2016 |
| WO | WO-2016/114970 A1 | 7/2016 |
| WO | WO-2016/115273 A1 | 7/2016 |
| WO | WO-2016/130578 A1 | 8/2016 |
| WO | WO-2016/137973 A1 | 9/2016 |
| WO | WO-2016/138148 A1 | 9/2016 |
| WO | WO-2016/149096 A1 | 9/2016 |
| WO | WO-2016/151107 A1 | 9/2016 |
| WO | WO-2016/168584 A1 | 10/2016 |
| WO | WO-2016/174229 A1 | 11/2016 |
| WO | WO-2016/187179 A1 | 11/2016 |
| WO | WO-2016/187256 A2 | 11/2016 |
| WO | WO-2017/005872 A1 | 1/2017 |
| WO | WO-2017/015123 A1 | 1/2017 |
| WO | WO-2017/060876 A1 | 4/2017 |
| WO | WO-2017/070056 A1 | 4/2017 |
| WO | WO-2017/075549 A1 | 5/2017 |
| WO | WO-2017/083375 A1 | 5/2017 |
| WO | WO-2017/087910 A1 | 5/2017 |
| WO | WO-2017/096158 A1 | 6/2017 |
| WO | WO-2017/117490 A1 | 7/2017 |
| WO | WO-2017/138984 A1 | 8/2017 |
| WO | WO-2017/139690 A1 | 8/2017 |
| WO | WO-2017/180949 A1 | 10/2017 |
| WO | WO-2017/184707 A1 | 10/2017 |
| WO | WO-2017/197338 A1 | 11/2017 |
| WO | WO-2017/197343 A2 | 11/2017 |
| WO | WO-2018/039338 A1 | 3/2018 |
| WO | WO-2018/075693 A1 | 4/2018 |
| WO | WO-2018/213643 A1 | 11/2018 |
| WO | WO-2018/226546 A1 | 12/2018 |
| WO | WO-2019/040637 A1 | 2/2019 |

OTHER PUBLICATIONS

Chokkalingam et al.( Lab on a chip 13.24 (2013): 4740-4744). (Year: 2013).*
U.S. Appl. No. 15/977,805, 10X Genomics, Inc.
U.S. Appl. No. 15/977,812, 10X Genomics, Inc.
U.S. Appl. No. 15/977,824, 10X Genomics, Inc.
U.S. Appl. No. 15/977,861, 10X Genomics, Inc.
U.S. Appl. No. 15/977,875, 10X Genomics, Inc.
Abate et al., "Beating Poisson encapsulation statistics using close-packed ordering," Lab Chip. 9(18):2628-31 (2009).
Abate et al., "High-throughput injection with microfluidics using picoinjectors," Proc Natl Acad Sci U S A. 107(45): 19163-6 (2010).
Abate et al., "Valve based flow focusing for drop formation," Appl Phys Lett. 94(2):023503-1-3 (2009) (3 pages).
AGC Chemicals, "Amorphous Fluoropolymer CYTOP:Chemistry for a Blue Planet," Jul. 2015 (10 pages).
AGC Chemicals, "Water/oil-repellent fluororesin coating material CYTOP(TM),", 2015 (1 page).
Aghvami et al., "Rapid prototyping of cyclic olefin copolymer (COC) microfluidic devices," Sens Actuators B Chem. 247: 940-949 (2017).
Akartuna et al., "Chemically induced coalescence in droplet-based microfluidics," Lab Chip. DOI:10.1039/c4lc01285b (2014) (5 pages).
Akselband et al., "Enrichment of slow-growing marine microorganisms from mixed cultures using gel microdrop (GMD) growth assay and fluorescence-activated cell sorting," J Exp Mar Bio Ecol. 329(2): 196-205 (2006).
Akselband et al., "Rapid mycobacteria drug susceptibility testing using Gel Microdrop (GMD) Growth Assay and flow cytometry," J Microbiol Methods. 62(2): 181-197 (2005).

Anna et al., "Formation of dispersions using 'flow focusing' in microchannels," Appl Phys Lett. 82(3): 364-366 (2003).
Attia et al., "Micro-injection moulding of polymer microfluidic devices," Microfluid Nanofluidics. 7(1): 1-28 (2009) (30 pages).
Baret et al., "Fluorescence-activated droplet sorting (FADS): efficient microfluidic cell sorting based on enzymatic activity," Lab Chip. 9(13): 1850-1859 (2009).
Baret, "Surfactants in droplet-based microfluidics," Lab Chip. 12(3): 422-433 (2012).
Becker et al., "Polymer microfabrication technologies for microfluidic systems," Anal Bioanal Chem. 390(1): 89-111 (2008).
Beer et al., "On-chip, real-time, single-copy polymerase chain reaction in picoliter droplets," Anal Chem. 79(22): 8471-8475 (2007).
Boone et al. "Plastic advances microfluidic devices," Anal Chem. 74(3): 78A-86A (2002).
Braeckmans et al., "Scanning the code. Encoded microcarrier beads signal the way to better combinatorial libraries and biological assays," Modern Drug Discovery. 6(2):28-30; 32 (2003) (4 pages).
Bransky et al., "A microfluidic droplet generator based on a piezoelectric actuator," Lab Chip. 9(4): 516-520 (2009).
Brouzes et al., "Droplet microfluidic technology for single-cell high-throughput screening," Proc Natl Acad Sci U S A. 106(34): 14195-14200 (2009).
Burns et al. "Microfabricated structures for integrated DNA analysis," Proc Natl Acad Sci U S A. 93(11): 5556-5561 (1996).
Burns et al., "An integrated nanoliter DNA analysis device," Science. 282(5388): 484-487 (1998).
Burns et al., "The intensification of rapid reactions in multiphase systems using slug flow in capillaries," Lab Chip. 1(1): 10-15 (2001).
Carroll et al. "The selection of high-producing cell lines using flow cytometry and cell sorting," Expert Opin Biol Ther. 4(11): 1821-1829 (2004).
Chakraborty et al., "Microfluidic step-emulsification in axisymmetric geometry," Lab Chip. 17(21): 3609-3620 (2017).
Chechetkin et al. "Sequencing by hybridization with the generic 6-mer oligonucleotide microarray: an advanced scheme for data processing," J Biomol Struct Dyn. 18(1): 83-101 (2000).
Chen et al. "Chemical transfection of cells in picoliter aqueous droplets in fluorocarbon oil," Anal Chem. 83(22): 8816-8820 (2011).
Chien et al., "Multiport flow-control system for lab-on-a-chip microfluidic devices," Fresenius J Anal Chem. 371(2): 106-11 (2001).
Chokkalingam et al., "Probing cellular heterogeneity in cytokine-secreting immune cells using droplet-based microfluidics," Lab Chip. 13(24): 4740-4744 (2013).
Chokkalingam et al., "Self-synchronizing pairwise production of monodisperse droplets by microfluidic step emulsification," Appl Phys Lett. 93(25): 254101-1-254101-3 (2008).
Chou et al., "Disposable microdevices for DNA analysis and cell sorting," Proc Solid-State Sensor and Actuator Workshop, Jun. 8-11, Hilton Head, SC, pp. 11-14 (1998).
Chu et al., "Controllable monodisperse multiple emulsions," Angew Chem Int Ed. 46(47): 8970-8974 (2007).
Clausell-Tormos et al. "Droplet-based microfluidic platforms for the encapsulation and screening of mammalian cells and multicellular organisms," Chem Biol. 15(5): 427-437 (2008).
Curcio, Mario, Thesis: "Improved techniques for high-throughput molecular diagnostics," Doctor of Philosophy, Royal Institute of Technology, 2002 (131 pages).
Damean et al., "Simultaneous measurement of reactions in microdroplets filled by concentration gradients," Lab Chip. 9(12): 1707-1713 (2009).
Dangla et al., "Droplet microfluidics driven by gradients of confinement," Proc Natl Acad Sci U S A. 110(3): 853-858 (2013).
Dangla et al., "The physical mechanisms of step emulsification," J Phys D Appl Phys. 46(11):114003 (2013) (8 pages).
De Bruin et al., "UBS investment research: Q-Series: DNA sequencing," UBS Securities LLC. Jul. 12, pp. 1-15 (2007).
De Mello et al., Chip technology for micro-separation. *Microsystem Technology: Biomethods*, vol. 10. Köhler J.M., Mejevaia T., Saluz H.P., 129-177 (1999).

(56) References Cited

OTHER PUBLICATIONS

Demirci et al., "Single cell epitaxy by acoustic picolitre droplets," Lab Chip. 7(9): 1139-1145 (2007).
Doerr, "The smallest bioreactor," Nat Methods. 2(5): 326 (2005).
Dowding et al., "Oil core/polymer shell microcapsules by internal phase separation from emulsion droplets. II: Controlling the release profile of active molecules," Langmuir. 21(12): 5278-5284 (2005).
Draper et al., "Compartmentalization of electrophoretically separated analytes in a multiphase microfluidic platform," Anal Chem. 84(13): 5801-5808 (2012).
Dressler et al., "Droplet-based microfluidics: enabling impact on drug discovery," J Biomol Screen. 19(4): 483-496 (2014).
Drmanac et al., "Sequencing by hybridization (SBH): advantages, achievements, and opportunities," Adv Biochem Eng Biotechnol. 77: 75-101 (2002).
Duffy et al., "Rapid prototyping of microfluidic systems in poly(dimethylsiloxane)," Anal Chem. 70(23): 4974-4984 (1998).
Eastburn et al., "Ultrahigh-throughput mammalian single-cell reverse-transcriptase polymerase chain reaction in microfluidic drops," Anal Chem. 85(16): 8016-8021 (2013).
Eggersdorfer et al, "Supplementary Information: Tandem emulsification for high-throughput production of double emulsions," Lab Chip. 17(5):936-942 (2017) (2 pages).
Eggersdorfer et al, "Tandem emulsification for high-throughput production of double emulsions," Lab Chip. 17(5): 936-942 (2017).
Esser-Kahn et al., "Triggered release from polymer capsules," Macromolecules. 44(14): 5539-5553 (2011).
Fisher et al., "A scalable, fully automated process for construction of sequence-ready human exome targeted capture libraries," Genome Biol. 12(1):R1 (2011) (15 pages).
Fredrickson et al., "Macro-to-micro interfaces for microfluidic devices," Lab Chip. 4(6): 526-533 (2004).
Freiberg et al., "Polymer microspheres for controlled drug release," Int J Pharm. 282(1-2): 1-18 (2004).
Fu et al., "A microfabricated fluorescence-activated cell sorter," Nature Biotechnol. 17(11): 1109-1111 (1999).
Fulton et al., "Advanced multiplexed analysis with the FlowMetrix system," Clin Chem. 43(9): 1749-1756 (1997).
Gai et al., "Spatiotemporal periodicity of dislocation dynamics in a two-dimensional microfluidic crystal flowing in a tapered channel," Proc Natl Acad Sci U S A. 113(43):12082-12087 (2016).
Gai et al., "Supporting Information: Spatiotemporal periodicity of dislocation dynamics in a two-dimensional microfluidic crystal flowing in a tapered channel," Proc Natl Acad Sci U S A. 1-9 (2016).
Galambos et al., "Precision alignment packaging for microsystems with multiple fluid connections," Proceedings of 2001 ASME: International Mechanical Engineering Conference and Exposition, Nov. 11-16, New York, NY. pp. 1-8 (2001).
Garstecki et al., "Formation of monodisperse bubbles in a microfluidic flow-focusing device," Appl Phys Lett. 85(13): 2649-2651 (2004).
Gartner et al., "The microfluidic toolbox—examples for fluidic interfaces and standardization concepts," Proc SPIE Int Soc Opt Eng. 6 pages (2003).
Ghadessy et al., "Directed evolution of polymerase function by compartmentalized self replication," Proc Natl Acad Sci U S A. 98(8): 4552-4557 (2001).
Granieri, Lucia, Thesis: "Droplet-based microfluidics and engineering of tissue plasminogen activator for biomedical applications," Doctor of Philosophy, L'Universite de Strasbourg, 2009 (131 pages).
Grasland-Mongrain et al., "Droplet coalescence in microfluidic devices," http://www.eleves.ens.fr./home/grasland/rapports/stage4.pdf, retrieved Jun. 4, 2007.
Guo et al., "Droplet microfluidics for high-throughput biological assays," Lab Chip. 21(12): 2146-2155 (2012).
Gyarmati et al., "Reversible disulphide formation in polymer networks: A versatile functional group from synthesis to applications," Eur Polym J. 49(6): 1268-1286 (2013).
Hashimshony et al., "CEL-Seq: Single-cell RNA-seq by multiplexed linear amplification," Cell Rep. 2(3): 666-673 (2012) (14 pages).

Hati et al., "Production of monodisperse drops from viscous fluids," Lab Chip. DOI: 10.1039/c7lc01322a (2018) (7 pages).
He et al., "Selective encapsulation of single cells and subcellular organelles into picoliter- and femtoliter-volume droplets," Anal Chem. 77(6): 1539-1544 (2005).
Holtze et al., "Biocompatible surfactants for water-in-fluorocarbon emulsions," Lab Chip. 8(10): 1632-1639 (2008).
Hosokawa et al., "Massively parallel whole genome amplification for single-cell sequencing using droplet microfluidics," Sci Rep. 7(1): 5199 (2017) (11 pages).
Huang et al., "Coating of poly(dimethylsiloxane) with n-dodecyl-Beta-D-maltoside to minimize nonspecific protein adsorption," Lab Chip. 5(10):1005-1007 (2005).
Huang et al., "Collective generation of milliemulsions by step-emulsification," RSC Adv. 7(24): 14932-14938 (2017).
Huebner et al., "Quantitative detection of protein expression in single cells using droplet microfluidics," Chem Commun. 12:1218-1220 (2007).
Hug et al., "Measurement of the number of molecules of a single mRNA species in a complex mRNA preparation," J Theor Biol. 221(4): 615-624 (2003).
Hwang et al., "Surface modification of cyclic olefin copolymer substrate by oxygen plasma treatment," Surf Coat Tech. 202(15): 3669-3674 (2008).
International Search Report and Written Opinion for International Application No. PCT/US2018/033280, dated Aug. 7, 2018 (19 pages).
Jena et al., "Cyclic olefin copolymer based microfluidic devices for biochip applications: Ultraviolet surface grafting using 2-methacryloyloxyethyl phosphorylcholine," Biomicrofluidics. 6(1): 012822-1-012822-12 (2012) (12 pages).
Jung et al., "Micro machining of injection mold inserts for fluidic channel of polymeric biochips," Sensors. 7(8): 1643-1654 (2007).
Kahkeshani et al., "Drop formation using ferrofluids driven magnetically in a step emulsification device," Lab Chip. 16(13): 2474-2480 (2016).
Katsura et al., "Indirect micromanipulation of single molecules in water-in-oil emulsion," Electrophoresis. 22(2): 289-293 (2001).
Kawai et al., Mass-production system of nearly monodisperse diameter gel particles using droplets formation in a microchannel. *Micro Total Analysis Systems 2002*, vol. 1. Baba Y., Shoji S., van den Berg A., 368-370 (2002).
Kenis et al., "Microfabrication inside capillaries using multiphase laminar flow patterning," Science. 285(5424): 83-85 (1999).
Khomiakova et al., "Analysis of perfect and mismatched DNA duplexes by a generic hexanucleotide microchip," Mol Biol (Mosk). 37(4): 726-741 (2003) (English abstract only) (1 page).
Kim et al., "Albumin loaded microsphere of amphiphilic poly(ethylene glycol)/poly(alpha-ester) multiblock copolymer," Eur J Pharm Sci. 23(3): 245-251 (2004).
Kim et al., "Fabrication of monodisperse gel shells and functional microgels in microfluidic devices," Angew Chem Int Ed Engl. 46(11): 1819-1822 (2007) (5 pages).
Kim et al., "Rapid prototyping of microfluidic systems using a PDMS/polymer tape composite," Lab Chip. 9(9): 1290-1293 (2009).
Klein et al., "Droplet barcoding for single-cell transcriptomics applied to embryonic stem cells," Cell. 161(5): 1187-1201 (2015) (22 pages).
Kobayashi et al., "Effect of slot aspect ratio on droplet formation from silicon straight-through microchannels," J Colloid Interface Sci. 279(1):277-80 (2004).
Kobayashi et al., "Preparation characteristics of oil-in-water emulsions using differently charged surfactants in straight-through microchannel emulsification," Colloids Surf A Physicochem Eng Asp. 229(1-3): 33-41 (2003).
Köster et al., "Drop-based microfluidic devices for encapsulation of single cells," Lab Chip. 8(7): 1110-1115 (2008).
Lagally et al., "Single-molecule DNA amplification and analysis in an integrated microfluidic device," Anal Chem. 73(3): 565-570 (2001).
Lagus et al., "A review of the theory, methods, and recent applications of high-throughput single-cell droplet microfluidics," J Phys D: Appl Phys. 46: 114005 (21 pages) (2013).

(56) References Cited

OTHER PUBLICATIONS

Li et al., "Step-emulsification in a microfluidic device," Lab Chip. 15(4):1023-31 (2015).
Li et al., Microfluidic Lab-on-a-Chip. *Ewing's Analytical Instrumentation Handbook*. . . Cazes, J., 581-679 (2005) (120 pages).
Loscertales et al., "Micro/nano encapsulation via electrified coaxial liquid jets," Science. 295(5560): 1695-1698 (2002).
Love et al., "A microengraving method for rapid selection of single cells producing antigen specific antibodies," Nat Biotechnol. 24(6): 703-707 (2006).
Lowe, Adam, Thesis: "Norbornenes and [n]polynorbornanes as molecular scaffolds for anion recognition," Doctor of Philosophy, Deakin University, 2010 (361 pages).
Maan et al., "Microfluidic emulsification in food processing," J Food Eng. 147:1-7 (2015).
Maan et al., "Spontaneous droplet formation techniques for monodisperse emulsions preparation Perspectives for food applications," J Food Eng. 107(3-4):334-46 (2011).
Macosko et al., "Supplemental Information: Highly parallel genome-wide expression profiling of individual cells using nanoliter droplets," Cell. 161(5): 1202-1214 (2015) (31 pages).
Mair et al., "Injection molded microfluidic chips featuring integrated interconnects," Lab Chip. 6(10): 1346-1354 (2006).
Makino et al., "Preparation of hydrogel microcapsules effects of preparation conditions upon membrane properties," Colloids Surf B Biointerfaces. 12(2): 97-104 (1998).
Man, Piu, Dissertation: "Monolithic structures for integrated microfluidic analysis," Doctor of Philosophy, The University of Michigan, 2001 (144 pages).
Mazutis et al., "Selective droplet coalescence using microfluidic systems," Lab Chip. 12(10): 1800-1806 (2012).
Mazutis et al., "Single-cell analysis and sorting using droplet-based microfluidics," available in PMC Aug. 11, 2014. Published in final edited form as Nat Protoc. 8(5): 870-891 (2013) (48 pages).
Merriman et al., "Progress in ion torrent semiconductor chip based sequencing," Electrophoresis. 33(23): 3397-3417 (2012).
Mittal et al., "Dynamics of step-emulsification: From a single to a collection of emulsion droplet generators," Phys Fluids. 26: 082109-1-082109-14 (2014).
Moore et al., "Behavior of capillary valves in centrifugal microfluidic devices prepared by three-dimensional printing," Microfluid Nanofluid. 10(4): 877-888 (2011).
Navin, "The first five years of single-cell cancer genomics and beyond," Genome Res. 25(10): 1499-1507 (2015).
Nisisako et al., "Droplet formation in a microchannel network," Lab Chip. 2(1): 24-26 (2002).
Nisisako et al., "Droplet formation in a microchannel on PMMA plate," *Micro Total Analysis Systems 2001*. Ramsey, J.M., van den Berg, A., 137-138 (2001).
Nisisako et al., "Microfluidic large-scale integration on a chip for mass production of monodisperse droplets and particles," Lab Chip. 8(2): 287-293 (2008).
Novak et al., "Single cell multiplex gene detection and sequencing using microfluidically-generated agarose emulsions," Available in PMC Jan. 10, 2012, published in final edited form as: Angew Chem Int Ed Engl. 50(2):390-5 (2011) (10 pages).
Oberholzer et al., "Polymerase chain reaction in liposomes," Chem Biol. 2(10):677-82 (1995).
Ogawa et al., "Production and characterization of O/W emulsions containing cationic droplets stabilized by lecithin-chitosan membranes," J Agric Food Chem. 51(9):2806-12 (2003).
Okushima et al., "Controlled production of monodisperse double emulsions by two-step droplet breakup in microfluidic devices," Langmuir. 20(23):9905-8 (2004).
Perez et al., "Poly(lactic acid)-poly(ethylene glycol) nanoparticles as new carriers for the delivery of plasmid DNA," J Control Release. 75(1-2):211-24 (2001).
Priest et al., "Generation of monodisperse gel emulsions in a microfluidic device," Appl Phys Lett. 88: 024106-1-024106-3 (2006).
Ramsey, J.M., "The burgeoning power of the shrinking laboratory," Nat Biotechnol. 17(11):1061-2 (1999).
Rotem et al., "High-throughput single-cell labeling (Hi-SCL) for RNA-Seq using drop-based microfluidics," PLoS One. 10(5):e0116328 (2015) (14 pages).
Rotem et al., "Single cell chip-seq using drop-based microfluidics," Frontiers of Single Cell Analysis, Sep. 5-7, Stanford, CA. Abstract 50 (2013) (1 page).
Ryan et al., "Rapid assay for mycobacterial growth and antibiotic susceptibility using gel microdrop encapsulation," J Clin Microbiol. 33(7):1720-6 (1995).
Sahin et al., "Microfluidic EDGE emulsification: the importance of interface interactions on droplet formation and pressure stability," Sci Rep. 6(26407):1-7 (2016).
Schirinzi et al., "Combinatorial sequencing-by-hybridization: analysis of the NF1 gene," Genet Test. 10(1):8-17 (2006).
Schmitt et al., "Bead-based multiplex genotyping of human papillomaviruses," J Clin Microbiol. 44(2):504-12 (2006).
Schuler et al., "Digital droplet PCR on disk," Lab Chip. 16 (1): 208-216 (2016).
Seiffert et al., "Smart microgel capsules from macromolecular precursors," J Am Chem Soc. 132(18):6606-9 (2010).
Shah et al., "Fabrication of monodisperse thermosensitive microgels and gel capsules in microfluidic devices," Soft Matter. 4:2303-9 (2008).
Shim et al., "Supporting Information: Control and measurement of the phase behavior of aqueous solutions using microfluidics," S1-S13 (2007) (13 pages).
Song et al., "Reactions in droplets in microfluidic channels," Angew Chem Int Ed Engl. 45(44):7336-56 (2006).
Stolovicki et al., "Throughput enhancement of parallel step emulsifier devices by shear-free and efficient nozzle clearance," Lab Chip. DOI: 10.1039/c71c01037k (2017) (7 pages).
Su et al., "Microfluidics-based biochips: technology issues, implementation platforms, and design-automation challenges," IEEE Transactions on Computer-Aided Design of Integrated Circuits and Systems. 25(2):211-23 (2006).
Sun et al., "Progress in research and application of liquid phase chip technology," China Journal of Experimental Surgery. 22(5) (2005) (5 pages).
Tawfik et al., "Man-made cell-like compartments for molecular evolution," Nat Biotechnol. 16(7):652-6 (1998).
Tewhey et al., "Microdroplet-based PCR enrichment for large-scale targeted sequencing," Nat Biotechnol. 27(11):1025-31 (2009) (11 pages).
Theberge et al., "Microdroplets in microfluidics: an evolving platform for discoveries in chemistry and biology," Angew Chem Int Ed Engl. 49(34):5846-68 (2010).
Thorsen et al., "Dynamic pattern formation in a vesicle-generating microfluidic device," Phys Rev Lett. 86(18):4163-6 (2001).
Tubeleviciute et al., "Compartmentalized self-replication (CSR) selection of Thermococcus litoralis Sh1 B DNA polymerase for diminished uracil binding," Protein Eng Des Sel. 23(8):589-97 (2010).
Turner et al., "Methods for genomic partitioning," Annu Rev Genomics Hum Genet. 10:263-84 (2009).
Van Dijke et al., "EDGE emulsification for food-grade dispersions," J Food Eng. 97(3): 348-354 (2010).
Van Dijke et al., "Effect of viscosities of dispersed and continuous phases in microchannel oil-in-water emulsification," Microfluid Nanofluid. 9(1):77-85 (2010).
Van Dijke et al., "Microchannel Emulsification: From Computational Fluid Dynamics to Predictive Analytical Model," Langmuir. 24(18): 10107-10115 (2008).
Van Dijke et al., "Parallelized edge-based droplet generation (EDGE) devices," Lab Chip. 9(19): 2824-2830 (2009).
Van Dijke et al., "Simultaneous Formation of Many Droplets in a Single Microfluidic Droplet Formation Unit," AIChE J. 56(3): 833-836 (2010).
Van Dijke et al., "The mechanism of droplet formation in microfluidic EDGE systems," Soft Matter. 6(2): 321-330 (2010).

(56) References Cited

OTHER PUBLICATIONS

Wagner et al., "Biocompatible fluorinated polyglycerols for droplet microfluidics as an alternative to PEG-based copolymer surfactants," Lab Chip. 16(1):65-9 (2016) (7 pages).

Wang et al., "A novel thermo-induced self-bursting microcapsule with magnetic-targeting property," Chemphyschem. 10(14):2405-9 (2009).

Ward et al., "Microfluidic flow focusing: drop size and scaling in pressure versus flow-rate-driven pumping," Electrophoresis. 26(19):3716-24 (2005).

Weaver et al., "Rapid clonal growth measurements at the single-cell level: gel microdroplets and flow cytometry," Biotechnology (N Y). 9(9):873-7 (1991).

Weigl et al., "Microfluidic diffusion-based separation and detection," Science. 283:346-7 (1999) (4 pages).

Whitesides et al., "Flexible methods for microfluidics," Phys Today. 54(6): 42-48 (2001).

Williams et al., "Amplification of complex gene libraries by emulsion PCR," Nat Methods. 3(7):545-50 (2006).

Zeng et al., "High-performance single cell genetic analysis using microfluidic emulsion generator arrays," Anal Chem. 82(8):3183-90 (2010).

Zhao et al., "Preparation of hemoglobin-loaded nano-sized particles with porous structure as oxygen carriers," Biomaterials. 28(7):1414-22 (2007).

Zilionis et al., "Single-cell barcoding and sequencing using droplet microfluidics," Nat Protoc. 12(1): 44-73 (2017).

Zong et al., "Genome-wide detection of single-nucleotide and copy-number variations of a single human cell," Science. 338(6114):1622-6 (2012) (6 pages).

Hosokawa, et al. Massively parallel whole genome amplification for single-cell sequencing using droplet microfluidics. Scientific Reports 7, Article No. 5199 (2017).

U.S. Appl. No. 16/443,629, 10X Genomics, Inc.

* cited by examiner

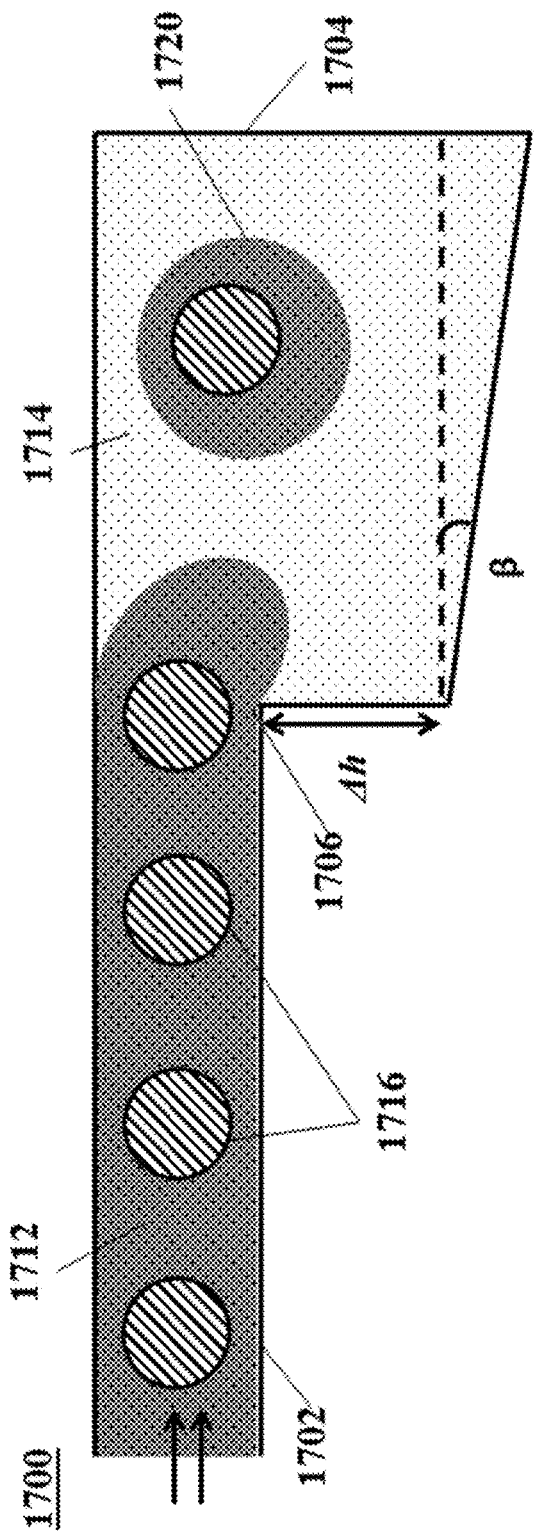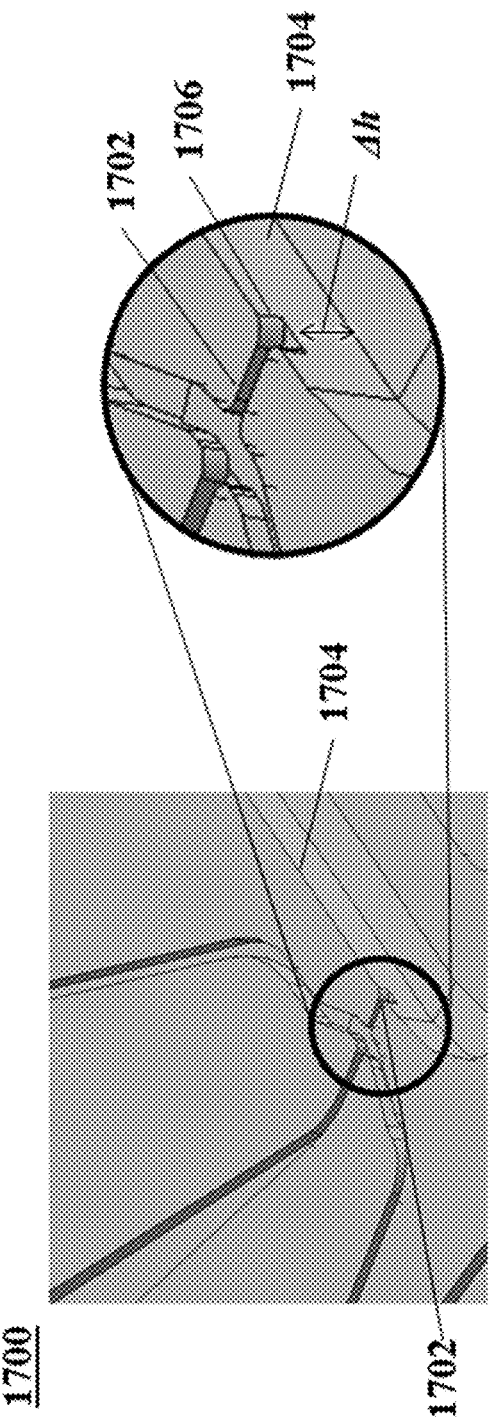
FIG. 17A
FIG. 17B

METHODS AND SYSTEMS FOR SORTING DROPLETS AND BEADS

CROSS-REFERENCE

This application is a continuation of International Application No. PCT/US2018/033280, filed May 17, 2018, which claims the benefit of U.S. Provisional Patent Application No. 62/508,219, filed May 18, 2017, each of which is entirely incorporated herein by reference.

BACKGROUND

A sample may be processed for various purposes, such as identification of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed using various reaction environments, such as partitions. Partitions may be wells or droplets. Droplets or wells may enable biological samples to be partitioned and processed separately. For example, such droplets may be fluidically isolated from other droplets, enabling accurate control of respective environments in the droplets.

A plurality of droplets can be generated such that one or more droplets include cells and/or particles. The cells and/or particles can be of interest for use in various (e.g., single cell) applications, such as nucleic acid amplification and/or sequencing applications.

SUMMARY

As recognized herein, when a plurality of droplets is generated, some droplets may not include any particles, such as cells and beads. A particle may be a bead, such as a gel bead and/or a cell bead. A particle may be a biological particle, such as a cell or cell derivative. A particle, such as a gel bead, may have a molecular barcode coupled thereto. Thus, recognized herein is a need to sort the plurality of droplets into a first subset of droplets that include particles and a second subset of droplets that do not. In some instances, when a plurality of cell beads is generated, some particles generated with the plurality of cell beads may not include any cells (e.g., non-cell bead). Recognized herein is a need to isolate the plurality of cell beads, such as by sorting a plurality of particles into a first subset of particles that include cells (e.g., cell beads) and a second subset of particles that do not.

In some aspects, the systems and methods for sorting described herein may yield an output comprising mostly singularly occupied droplets (containing a single particle of interest). For example, at least about 90%, 95%, 96%, 97%, 98%, 99%, or more of a plurality of droplets may be singularly occupied droplets. Droplets may be sorted, such as by (i) introducing field-attractable particles (e.g., magnetic particles) into the droplets and subjecting the droplets to a field (e.g., magnetic field), (ii) subjecting the droplets to a pressure pulse and separating the droplets based on hydrodynamic forces, and/or (iii) directing the droplets to interface physical structures (e.g., having apertures) in a flow path of the droplets and separating the droplets based on mechanical properties (e.g., deformability) of the droplets.

In some aspects, the systems and methods for sorting described herein may yield an output comprising mostly singularly occupied cell beads (containing a single cell). For example, at least about 90%, 95%, 96%, 97%, 98%, 99%, or more of a population of beads (or particles) may be singularly occupied cell beads. Cell beads may be isolated (or sorted), such as by (i) generating cell beads with field-attractable particles (e.g., magnetic particles), such as by polymerizing the droplets containing the field-attractable particles, and subjecting the cell beads to a field (e.g., magnetic field), (ii) subjecting the cell beads to a pressure pulse and separating the cell beads via hydrodynamic forces, and/or (iii) directing the cell beads to interface physical structures (e.g., having apertures) in a flow path of the cell beads and separating the cell beads based on mechanical properties (e.g., deformability) of the cell beads. In some cases, already sorted droplets, which are mostly singularly occupied droplets (e.g., containing a single cell), may be polymerized to generate cell beads that are mostly singularly occupied. In some cases, a plurality of droplets may be selectively polymerized, such that mostly (or only) singularly occupied droplets are polymerized to generate cell beads that are mostly singularly occupied.

Provided herein are methods and systems for sorting droplets that can isolate droplets that include biological particles (e.g., a cell) and/or other particles (e.g., gel beads, cell beads, etc.) from droplets that do not include biological particles and/or other particles. The methods and systems may isolate droplets that are singularly occupied from droplets that are non-singularly occupied, such as from unoccupied droplets or multiply occupied droplets. In another aspect, provided herein are methods and systems that can isolate particles that include cells (e.g., cell beads) from particles that do not include cells. The methods and systems may isolate cell beads that are singularly occupied from particles that are non-singularly occupied, such as from unoccupied particles or multiply occupied cell beads. The isolated droplets (that include biological particles and/or other particles) and/or isolated cell beads (that include cells) can be subject to further applications, such as nucleic acid amplification and/or sequencing. Beneficially, such pre-sorting may increase efficiency of downstream applications by significantly saving time and resources (e.g., valuable reagents).

The methods and systems generally operate by generating a plurality of droplets such that each of the plurality of droplets comprises field-attractable particles. A given droplet in the plurality of droplets may or may not include one or more particles (e.g., biological particles, beads, etc.). Thus, the plurality of droplets comprising field attractable particles can comprise a first subset of droplets that include one or more particles and a second subset of droplets that do not include any particles. A given droplet in the first subset of droplets that include one or more particles can comprise a sufficiently discrepant number or concentration of field-attractable particles than a given droplet in the second subset of droplets that do not include any particles such that when the plurality of droplets is subject to an electric or magnetic field, the first subset of droplets and the second subset of droplets are separated from each other. In some cases, when the plurality of droplets is subjected to an electric or magnetic field, singularly occupied droplets may be separated from unoccupied droplets and otherwise multiply occupied droplets.

In some instances, a plurality of particles may be generated with field-attractable particles, such as by polymerizing the plurality of droplets comprising the field-attractable particles. A given particle may or may not include a cell. Thus, the plurality of particles comprising field attractable particles may comprise a first subset of particles (e.g., cell beads) that include cells and a second subset of particles that does not include cells. A given cell bead in the first subset of particles can comprise a sufficiently discrepant number or concentration of field-attractable particles than a given particle in the second subset of particles, such that when the plurality of particles is subject to an electric or magnetic field, the first subset of particles and the second subset of particles are separated from each other. In some cases, when the plurality of particles is subjected to an electric or magnetic field, singularly occupied cell beads may be separated from unoccupied particles and otherwise multiply occupied cell beads.

In some instances, a plurality of droplets can be generated without field-attractable particles. A given droplet in the plurality of droplets may or may not include one or more particles. Thus, the plurality of droplets can comprise a first subset of droplets that include one or more particles and a second subset of droplets that do not include any particles. The plurality of droplets can be subject to a pressure pulse and the first subset of droplets and the second subset of droplets can be separated from each other via hydrodynamic forces. In some cases, the plurality of droplets can be subject to an electric field, and the first subset and the second subset of droplets can be separated via dielectrophoresis. In some cases, singularly occupied droplets may be separated from unoccupied droplets and otherwise multiply occupied droplets.

In some instances, a plurality of particles can be generated without field-attractable particles. A given particle in the plurality particles may or may not include one or more cells. Thus, the plurality of particles can comprise a first subset of particles (e.g., cell beads) that include one or more cells and a second subset of particles that do not include any cells. The plurality of particles can be subject to a pressure pulse and the first subset of particles and the second subset of particles can be separated from each other via hydrodynamic forces. In some cases, the plurality of particles can be subject to an electric field, and the first subset and the second subset can be separated via dielectrophoresis. In some cases, singularly occupied cell beads may be separated from unoccupied particles and otherwise multiply occupied cell beads.

In some instances, a plurality of droplets comprising a first subset of droplets that include one or more particles and a second subset of droplets that do not include any particles can be sorted via a passive mechanism based on mechanical properties of the droplets, such as the respective deformability properties of the droplets. When the plurality of droplets is directed to pass through one or more apertures, each aperture having a size smaller than a minimum dimension of a droplet, only deforming droplets may pass through the apertures and non-deforming droplets may be trapped on the apertures. Unoccupied droplets may have higher deformability and/or lower surface tension properties compared to occupied droplets, thus allowing occupied droplets to be trapped on one or more apertures, and allowing unoccupied droplets to pass through the one or more apertures, thereby separating the first subset and second subset of droplets from the plurality of droplets.

In some instances, a plurality of particles comprising a first subset of particles (e.g., cell beads) that include one or more cells and a second subset of particles that do not include any particles can be sorted via a passive mechanism based on mechanical properties of the particles, such as the respective deformability properties (or rigidity) of the particles. When the plurality of particles is directed to pass through one or more apertures, each aperture having a size smaller than a minimum dimension of a particle, only deforming particles may pass through the apertures and non-deforming particles may be trapped on the apertures. Unoccupied particles (e.g., not having cells or their derivatives) may have higher deformability and/or lower surface tension properties compared to cell beads, thus allowing cell beads to be trapped on one or more apertures, and allowing unoccupied particles to pass through the one or more apertures, thereby separating the first subset and second subset of particles from the plurality of particles.

In an aspect, provided is a method for sorting droplets, comprising: (a) bringing a first phase in contact with a second phase to generate a plurality of droplets, wherein the first phase and second phase are immiscible, wherein the plurality of droplets comprises field-attractable particles and wherein (i) a first subset of the plurality of droplets includes biological particles or particles having coupled thereto molecular barcodes, and (ii) a second subset of the plurality of droplets does not include the biological particles; (b) directing the plurality of droplets along a first channel towards an intersection of the first channel with a second channel and a third channel; and (c) subjecting the plurality of droplets comprising the field-attractable particles to an electric or magnetic field under conditions sufficient to separate at least a portion of the first subset of the plurality of droplets from at least a portion of the second subset of the plurality of droplets, wherein upon separation, the at least the portion of the first subset of the plurality of droplets flows along the second channel and the at least the portion of the second subset of the plurality of droplets flows along the third channel.

In some embodiments, the second subset of the plurality of droplets does not include the particles having coupled thereto molecular barcodes.

In some embodiments, a concentration of the field-attractable particles in the second subset of the plurality of droplets is substantially uniform.

In some embodiments, each droplet of the first subset of the plurality of droplets comprises less field attractable particles than each droplet of the second subset of the plurality of droplets. In some embodiments, wherein the electric or magnetic field induces forces on the second subset of the plurality of droplets that is greater than forces induced on the first subset of the plurality of droplets.

In some embodiments, the field-attractable particles are magnetic-field attractable particles. In some embodiments, the field-attractable particles are paramagnetic particles.

In some embodiments, the field-attractable particles are electric-field attractable particles. In some embodiments, the field-attractable particles are conductive particles.

In some embodiments, the first subset of the plurality of droplets includes biological particles and the particles having coupled thereto molecular barcodes. In some embodiments, the particles having coupled thereto molecular barcodes are beads. In some embodiments, the beads are gel beads.

In some embodiments, the method further comprises, subsequent to (c), subjecting nucleic acid molecules derived from the biological particles in the first subset to nucleic acid sequencing. In some embodiments, the method further comprises, subsequent to (c), subjecting the first subset of the plurality of droplets to nucleic acid amplification conditions to yield amplification products of the nucleic acid molecules from the biological particles in the first subset. In some embodiments, the method further comprises subjecting the amplification products to nucleic acid sequencing.

In some embodiments, the conditions of the electric or magnetic field sufficient to separate the at least the portion of the first subset of the plurality of droplets and the at least the portion of the second subset of the plurality of droplets are determined based at least in part on a ratio between sizes of the plurality of droplets and sizes of the biological particles and/or particles having coupled thereto molecular barcodes in the first subset of the plurality of droplets.

In some embodiments, the plurality of droplets is directed along the first channel using a pressure pulse.

In some embodiments, the molecular barcodes are releasably coupled to the particles.

In some embodiments, the method further comprises subjecting individual droplets of the first subset of the plurality of droplets to a stimulus to facilitate polymerization in the biological particles. In some embodiments, the stimulus is an optical stimulus. In some embodiments, the optical stimulus a laser or ultraviolet light. In some embodiments, the stimulus is a chemical stimulus. In some embodiments, the stimulus is applied prior to the intersection. In some embodiments, the stimulus is applied along the first channel. In some embodiments, the stimulus is applied along the second channel. In some embodiments, the method further comprises (i) detecting the individual droplets and (ii) subjecting the individual droplets to the stimulus upon detecting the individual droplets.

In some embodiments, the biological particles are cells enclosed within or comprising a gel or polymer matrix.

In some embodiments, the first subset comprises a third subset of droplets each comprising a single biological particle and a fourth subset of droplets each comprising multiple biological particles, the method further comprising: directing the first subset of the plurality of droplets along the second channel towards a second intersection of the second channel with a fourth channel and a fifth channel, and subjecting the first subset to an electric or magnetic field under conditions sufficient to separate at least a portion of the third subset from at least a portion of the fourth subset, wherein upon separation, the at least the portion of the third subset of droplets flows along a fourth channel and the at least the portion of the fourth subset of droplets flows along a fifth channel.

In another aspect, provided is a system for sorting droplets, comprising: a fluid flow path comprising a first channel, a second channel and a third channel; a fluid flow unit that is configured to subject a plurality of droplets to flow along the first channel, wherein the plurality of droplets is generated upon bringing a first phase in contact with a second phase, wherein the first phase and second phase are immiscible, wherein the plurality of droplets comprises field-attractable particles, and wherein (i) a first subset of the plurality of droplets includes biological particles or particles having coupled thereto molecular barcodes, and (ii) a second subset of the plurality of droplets does not include the biological particles; a field application unit that is configured to apply an electric or magnetic field; and a controller operatively coupled to the fluid flow unit and the field application unit, wherein the controller is programmed to (i) direct the fluid flow unit to subject the plurality of droplets to flow along the first channel to an intersection of the first channel with the second channel and the third channel, and (ii) direct the field application unit to subject the plurality of droplets comprising the field-attractable particles to the electric or magnetic field under conditions sufficient to separate at least a portion of the first subset of the plurality of droplets from at least a portion of the second subset of the plurality of droplets, wherein upon separation, the at least the portion of the first subset of the plurality of droplets flows along the second channel and the at least the portion of the second subset of the plurality of droplets flows along the third channel.

In some embodiments, the second subset of the plurality of droplets does not include the particles having coupled thereto molecular barcodes.

In some embodiments, the field application unit is configured to apply the electric field. In some embodiments, the field application unit is configured to apply the magnetic field. In some embodiments, the field application unit is configured to apply the electric field and magnetic field.

In some embodiments, the field-attractable particles are magnetic-field attractable particles. In some embodiments, the field-attractable particles are paramagnetic particles.

In some embodiments, the field-attractable particles are electric-field attractable particles. In some embodiments, the field-attractable particles are conductive particles.

In some embodiments, the fluid flow unit includes at least one pump that is configured to provide negative pressure. In some embodiments, the fluid flow unit includes at least one compressor that is configured to provide positive pressure.

In some embodiments, the fluid flow unit is configured to apply a pressure pulse to direct the plurality of droplets along the first channel.

In some embodiments, the fluid flow unit is configured to apply a pressure pulse to direct the first or second subset of the plurality of droplets along the second channel or third channel, respectively.

In some embodiments, the controller is programmed to direct the fluid flow unit to subject the first subset of the plurality of droplets to a pressure pulse at the intersection to subject the first subset of the plurality of droplets to flow along the second channel.

In some embodiments, the fluid flow unit includes an actuator that is configured to subject the plurality of droplets to flow.

In some embodiments, the controller is programmed to determine the conditions of the electric or magnetic field sufficient to separate the at least the portion of the first subset of the plurality of droplets and the at least the portion of the second subset of the plurality of droplets based at least in part on a ratio between sizes of the plurality of droplets and/or sizes of the biological particles or particles having coupled thereto molecular barcodes in the first subset of the plurality of droplets.

In some embodiments, each droplet of the first subset of the plurality of droplets comprises less field attractable particles than each droplet of the second subset of the plurality of droplets. In some embodiments, wherein the electric or magnetic field induces forces on the second subset of the plurality of droplets that is greater than forces induced on the first subset of the plurality of droplets.

In some embodiments, the biological particles are cells enclosed within or comprising a gel or polymer matrix.

In another aspect, provided is a non-transitory computer-readable medium comprising machine-executable code that, upon execution by one or more computer processors, implements a method for sorting droplets, comprising: (a) bringing a first phase in contact with a second phase to generate a plurality of droplets, wherein the first phase and second phase are immiscible, wherein the plurality of droplets comprises field-attractable particles, and wherein (i) a first subset of the plurality of droplets includes biological particles or particles having coupled thereto molecular barcodes, and (ii) a second subset of the plurality of droplets does not include the biological particles; (b) directing the plurality of droplets along a first channel towards an intersection of the first channel with a second channel and a third channel; and (c) subjecting the plurality of droplets comprising the field-attractable particles to an electric or magnetic field under conditions sufficient to separate at least a portion of the first subset of the plurality of droplets from at least a portion of the second subset of the plurality of droplets, wherein upon separation, the at least the portion of the first subset of the plurality of droplets flows along the second channel and the at least the portion of the second subset of the plurality of droplets flows along the third channel.

In another aspect, provided is a method for sorting droplets, comprising: (a) bringing a first phase in contact with a second phase to generate a plurality of droplets, wherein the first phase and second phase are immiscible, and wherein (i) a first subset of the plurality of droplets includes biological particles or particles, which particles comprise molecular barcodes coupled thereto, and (ii) a second subset of the plurality of droplets does not include the biological particles; (b) directing the plurality of droplets along a first channel towards an intersection of the first channel with a second channel and a third channel; and (c) at the intersection, subjecting the plurality of droplets to a pressure pulse under conditions sufficient to separate at least a portion of the first subset of the plurality of droplets from at least a portion of the second subset of the plurality of droplets, wherein upon separation, the at least the portion of the first subset of the plurality of droplets flows along the second channel and the at least the portion of the second subset of the plurality of droplets flows along the third channel.

In some embodiments, the second subset of the plurality of droplets does not include the particles having coupled thereto molecular barcodes.

In some embodiments, the pressure pulse induces forces on the second subset of the plurality of droplets that is greater than forces induced on the first subset of the plurality of droplets.

In some embodiments, the first subset of the plurality of droplets includes biological particles and the particles having coupled thereto molecular barcodes. In some embodiments, the particles having coupled thereto molecular barcodes are beads. In some embodiments, the beads are gel beads.

In some embodiments, the method further comprises, subsequent to (c), subjecting nucleic acid molecules derived from the biological particles in the first subset to nucleic acid sequencing. In some embodiments, the method further comprises, subsequent to (c), subjecting the first subset of the plurality of droplets to nucleic acid amplification conditions to yield amplification products of the nucleic acid molecules from the biological particles in the first subset. In some embodiments, the method further comprises subjecting the amplification products to nucleic acid sequencing.

In some embodiments, the molecular barcodes are releasably coupled to the particles.

In some embodiments, the method further comprises subjecting individual droplets of the first subset of the plurality of droplets to a stimulus to facilitate polymerization in the biological particles. In some embodiments, the method further comprises (i) detecting the individual droplets and (ii) subjecting the individual droplets to the stimulus upon detecting the individual droplets.

In some embodiments, the biological particles are cells enclosed within or comprising a gel or polymer matrix.

In another aspect, provided is a system for sorting droplets, comprising: a fluid flow path comprising a first channel, a second channel and a third channel; a fluid flow unit that is configured to subject a plurality of droplets to flow along the first channel, wherein the plurality of droplets is generated upon bringing a first phase in contact with a second phase, wherein the first phase and second phase are immiscible, and wherein (i) a first subset of the plurality of droplets includes biological particles or particles having coupled thereto molecular barcodes, and (ii) a second subset of the plurality of droplets does not include the biological particles; a pressure application unit that is configured to apply a pressure pulse; and a controller operatively coupled to the fluid flow unit and the pressure application unit, wherein the controller is programmed to (i) direct the fluid flow unit to subject the plurality of droplets to flow along the first channel to an intersection of the first channel with the second channel and the third channel, and (ii) direct the pressure application unit to subject the plurality of droplets to the pressure pulse under conditions sufficient to separate at least a portion of the first subset of the plurality of droplets from at least a portion of the second subset of the plurality of droplets, wherein upon separation, the at least the portion of the first subset of the plurality of droplets flows along the second channel and the at least the portion of the second subset of the plurality of droplets flows along the third channel.

In another aspect, provided is a non-transitory computer-readable medium comprising machine-executable code that, upon execution by one or more computer processors, implements a method for sorting droplets, comprising: (a) bringing a first phase in contact with a second phase to generate a plurality of droplets, wherein the first phase and second phase are immiscible, and wherein (i) a first subset of the plurality of droplets includes biological particles or particles having coupled thereto molecular barcodes, and (ii) a second subset of the plurality of droplets does not include the biological particles; (b) directing the plurality of droplets along a first channel towards an intersection of the first channel with a second channel and a third channel; and (c) subjecting the plurality of droplets to a pressure pulse under conditions sufficient to separate at least a portion of the first subset of the plurality of droplets from at least a portion of the second subset of the plurality of droplets, wherein upon separation, the at least the portion of the first subset of the plurality of droplets flows along the second channel and the at least the portion of the second subset of the plurality of droplets flows along the third channel.

In another aspect, provided is a method for droplet processing, comprising: (a) bringing a first phase in contact with a second phase to generate a plurality of droplets, wherein the first phase and second phase are immiscible, wherein (i) a first subset of the plurality of droplets includes biological particles, and (ii) a second subset of the plurality of droplets does not include the biological particles; (b) directing the plurality of droplets along a first channel towards an intersection of the first channel with a second channel and a third channel; (c) prior to the intersection, selectively subjecting individual droplets of the first subset of the plurality of droplets to a stimulus to facilitate polymerization in the biological particles; and (d) separating at least a portion of the first subset of the plurality of droplets from at least a portion of the second subset of the plurality of droplets at the intersection, wherein upon separation, the at least the portion of the first subset of the plurality of droplets flows along the second channel and the at least the portion of the second subset of the plurality of droplets flows along the third channel.

In some embodiments, the first subset of the plurality of droplets include particles having coupled thereto molecular barcodes.

In some embodiments, the second subset of the plurality of droplets does not include the particles having coupled thereto molecular barcodes.

In some embodiments, the method further comprises (i) detecting the individual droplets and (ii) selectively subjecting the individual droplets to the stimulus upon detecting the individual droplets.

In another aspect, provided is a method for sorting droplets, comprising: (a) bringing a first phase in contact with a second phase to generate a plurality of droplets, wherein the first phase and second phase are immiscible, wherein the plurality of droplets comprises field-attractable particles and wherein the plurality of droplets comprises (i) a first subset of droplets each including, and not more than, one biological particle, and (ii) a second subset of droplets each either not including any biological particle or including more than one biological particle; (b) directing the plurality of droplets along a first channel towards an intersection of the first channel with a second channel and a third channel; and (c) subjecting the plurality of droplets comprising the field-attractable particles to an electric or magnetic field under conditions sufficient to separate at least a portion of the first subset of the plurality of droplets from at least a portion of the second subset of the plurality of droplets, wherein upon separation, the at least the portion of the first subset of the plurality of droplets flows along the second channel and the at least the portion of the second subset of the plurality of droplets flows along the third channel.

In some embodiments, the first subset of the plurality of droplets include particles having coupled thereto molecular barcodes. In some embodiments, the particles having coupled thereto molecular barcodes are beads. In some embodiments, the beads are gel beads.

In some embodiments, a concentration of the field-attractable particles in droplets of the second subset which do not include any biological particle is substantially uniform.

In some embodiments, each droplet of the first subset of the plurality of droplets comprises (i) less field attractable particles than each droplet of the second subset of the plurality of droplets which do not include any biological particle, and (ii) more field attractable particles than each droplet of the second subset of the plurality of droplets which includes more than one biological particle. In some embodiments, forces induced by the electric or magnetic field on droplets of the second subset which do not include any biological particle is greater than forces induced on the first subset, which forces induced on the first subset are greater than forces induced on droplets of the second subset which includes more than one biological particle.

In some embodiments, the field-attractable particles are magnetic-field attractable particles. In some embodiments, the field-attractable particles are paramagnetic particles.

In some embodiments, the field-attractable particles are electric-field attractable particles. In some embodiments, the field-attractable particles are conductive particles.

In some embodiments, the method further comprises, subsequent to (c), subjecting nucleic acid molecules derived from the biological particles in the first subset to nucleic acid sequencing.

In some embodiments, the method further comprises, subsequent to (c), subjecting the first subset of the plurality of droplets to nucleic acid amplification conditions to yield amplification products of the nucleic acid molecules from the biological particles in the first subset. In some embodiments, the method further comprises subjecting the amplification products to nucleic acid sequencing.

In some embodiments, the conditions of the electric or magnetic field sufficient to separate the at least the portion of the first subset of the plurality of droplets and the at least the portion of the second subset of the plurality of droplets are determined based at least in part on a ratio between sizes of the plurality of droplets and sizes of the biological particles in the first subset of the plurality of droplets.

In some embodiments, the plurality of droplets is directed along the first channel using a pressure pulse.

In some embodiments, the method further comprises subjecting individual droplets of the first subset of the plurality of droplets to a stimulus to facilitate polymerization in the biological particles. In some embodiments, the stimulus is applied prior to the intersection. In some embodiments, the method further comprises (i) detecting the individual droplets and (ii) subjecting the individual droplets to the stimulus upon detecting the individual droplets.

In some embodiments, the biological particles are cells enclosed within or comprising a gel or polymer matrix.

In another aspect, provided is a method for sorting droplets, comprising: (a) bringing a first phase in contact with a second phase to generate a plurality of droplets, wherein the first phase and second phase are immiscible, wherein the plurality of droplets comprises (i) a first subset of droplets each including, and not more than, one biological particle, and (ii) a second subset of droplets each either not including any biological particle or including more than one biological particle; (b) directing the plurality of droplets along a first channel towards an intersection of the first channel with a second channel and a third channel; and (c) subjecting the plurality of droplets to a pressure pulse under conditions sufficient to separate at least a portion of the first subset of the plurality of droplets from at least a portion of the second subset of the plurality of droplets, wherein upon separation, the at least the portion of the first subset of the plurality of droplets flows along the second channel and the at least the portion of the second subset of the plurality of droplets flows along the third channel.

In some embodiments, the first subset of the plurality of droplets include particles having coupled thereto molecular barcodes. In some embodiments, the particles having coupled thereto molecular barcodes are beads. In some embodiments, the beads are gel beads.

In some embodiments, forces induced by the pressure pulse on droplets of the second subset which do not include any biological particle is greater than forces induced on the first subset, which forces induced on the first subset are greater than forces induced on droplets of the second subset which includes more than one biological particle.

In some embodiments, the method further comprises, subsequent to (c), subjecting nucleic acid molecules derived from the biological particles in the first subset to nucleic acid sequencing. In some embodiments, the method further comprises, subsequent to (c), subjecting the first subset of the plurality of droplets to nucleic acid amplification conditions to yield amplification products of the nucleic acid molecules from the biological particles in the first subset. In some embodiments, the method further comprises subjecting the amplification products to nucleic acid sequencing.

In some embodiments, the method further comprises subjecting individual droplets of the first subset of the plurality of droplets to a stimulus to facilitate polymerization in the biological particles. In some embodiments, the method further comprises (i) detecting the individual droplets and (ii) subjecting the individual droplets to the stimulus upon detecting the individual droplets.

In some embodiments, the biological particles are cells enclosed within or comprising a gel or polymer matrix.

In another aspect, provided is a method for sorting particles, comprising: (a) providing a plurality of particles, wherein the plurality of particles comprises (i) a first subset of particles each including a biological particle from or contents of a plurality of cells and (ii) a second subset of particles each not including a biological particle from or contents of the plurality of cells; and (b) sorting the plurality of particles, thereby isolating at least a portion of the first subset of particles from at least a portion of the second subset of particles.

In some embodiments, the first subset of particles comprises a third subset of particles each including, but not more than, one biological particle from the plurality of cells and a fourth subset of particles each including more than one biological particle from the plurality of cells. In some embodiments, the method further comprises sorting the first subset of particles, thereby isolating at least a portion of the third subset of particles from at least a portion of the fifth subset of particles.

In some embodiments, (b) comprises subjecting the plurality of particles to a magnetic or electric field. In some embodiments, each particle of the plurality of particles comprises field-attractable particles.

In some embodiments, wherein (b) comprises subjecting the plurality of particles to a pressure pulse.

In another aspect, provided is a method for sorting particles, comprising: (a) providing a plurality of particles generated from a plurality of cells, wherein the plurality of particles comprises (i) a first subset of particles each including, but not more than, one biological particle from or contents of a single cell from the plurality of cells and (ii) a second subset of particles each either not including a biological particle from or contents of the plurality of cells or including more than one biological particle from or contents of the plurality of cells; and (b) sorting the plurality of particles, thereby isolating at least a portion of the first subset of particles from at least a portion of the second subset of particles.

In some embodiments, (b) comprises subjecting the plurality of particles to a magnetic or electric field. In some embodiments, each particle of the plurality of particles comprises field-attractable particles.

In some embodiments, (b) comprises subjecting the plurality of particles to a pressure pulse.

In another aspect, provided is a method for processing droplets. The method can comprise: providing a plurality of gel beads in a first phase, wherein the plurality of gel beads comprise (i) molecular barcodes and (ii) field-attractable particles; and subjecting the plurality of gel beads comprising the field-attractable particles to an electric or magnetic field under conditions sufficient to separate the plurality of gel beads from at least 50% of the first phase, thereby providing the plurality of gel beads in a second phase that is immiscible with respect to the first phase.

In some embodiments, the plurality of gel beads can be separated from at least 60% of the first phase. In some embodiments, the plurality of gel beads can be separated from at least 80% of the first phase. In some embodiments, the plurality of gel beads can be separated from at least 90% of the first phase.

In some embodiments, the first phase can be an oil phase. In some embodiments, the second phase can be an aqueous phase.

In another aspect, provided is a method for sorting gel beads, comprising: processing a plurality of droplets to generate a plurality of gel beads, wherein the plurality of droplets comprises field-attractable particles and wherein (i) a first subset of the plurality of gel beads includes biological particles or particles having coupled thereto molecular barcodes, and (ii) a second subset of the plurality of gel beads does not include the biological particles, directing the plurality of gel beads along a first channel towards an intersection of the first channel with a second channel and a third channel; and subjecting the plurality of gel beads to an electric or magnetic field under conditions sufficient to separate the first subset of the plurality of gel beads from the second subset of the plurality of gel beads, wherein upon separation, the first subset of the plurality of gel beads flows along the second channel and the second subset of the plurality of gel beads flows along the third channel.

In some embodiments, the processing comprises polymerizing the plurality of droplets.

In another aspect, provided is a method for sorting gel beads, comprising: processing a plurality of droplets to generate a plurality of gel beads, wherein (i) a first subset of the plurality of gel beads includes biological particles or particles having coupled thereto molecular barcodes, and (ii) a second subset of the plurality of gel beads does not include the biological particles, directing the plurality of gel beads along a first channel towards an intersection of the first channel with a second channel and a third channel; and at the intersection, subjecting the plurality of gel beads to a pressure pulse under conditions sufficient to separate the first subset of the plurality of gel beads from the second subset of the plurality of gel beads, wherein upon separation, the first subset of the plurality of gel beads flows along the second channel and the second subset of the plurality of gel beads flows along the third channel.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 17A shows a cross-section view of another example of a microfluidic channel structure with a geometric feature for controlled partitioning. FIG. 17B shows a perspective view of the channel structure of FIG. 17A.

DETAILED DESCRIPTION

Figure 1:
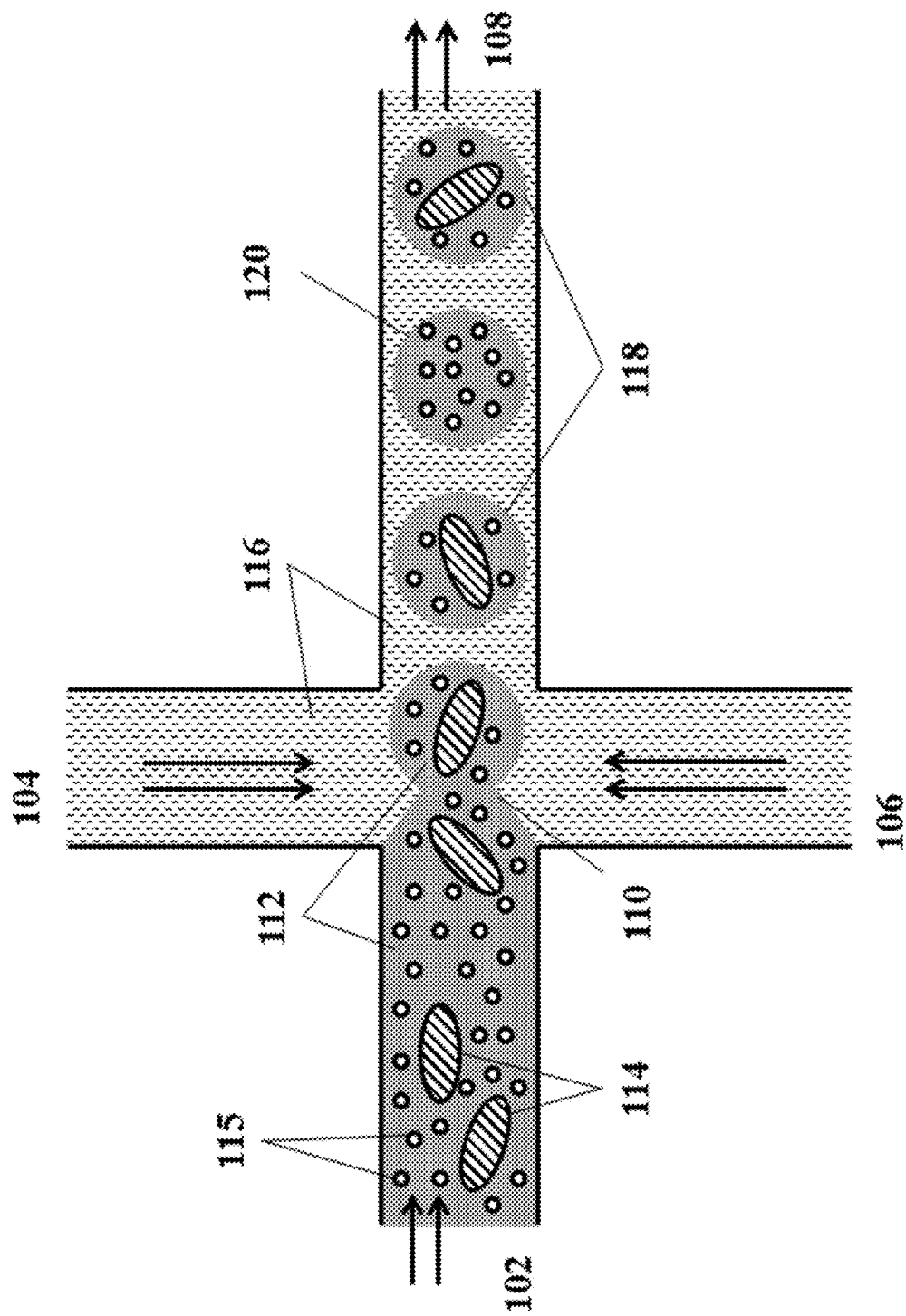
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The efficiency of many single cell applications can increase by improving cell throughput. For example, this can be achieved by sorting a plurality of droplets that may or may not contain cells and/or particles therein to collect only the droplets that contain the cells and/or particles therein. The plurality of droplets may be sorted to isolate singularly occupied droplets from non-singularly occupied droplets (e.g., unoccupied, multiply occupied, etc.). In another example, higher efficiency can be achieved by isolating a plurality of cell beads from a plurality of particles that may or may not contain cells therein. The plurality of particles may be sorted to isolate singularly occupied cell beads (e.g., particles containing cells or their derivatives) from non-singularly occupied cell beads (e.g., unoccupied particles, multiply occupied cell beads, etc.). The isolated population of droplets that contain (e.g., singularly contain) the cells and/or particles therein, and/or cell beads that contain (e.g., singularly contain) the cells therein, can then be subject to further applications, such as nucleic acid amplification and/or sequencing applications.

Provided are methods and systems for sorting droplets. The methods and systems generally operate by generating a plurality of droplets such that each of the plurality of droplets comprises field-attractable particles. A given droplet in the plurality of droplets may or may not include therein one or more cells and/or other particles (e.g., cell beads, gel beads, etc.). In some cases, the other particles (e.g., gel beads) may have molecular barcodes coupled thereto. Thus, the plurality of droplets comprising field attractable particles can comprise a first subset of droplets that include one or more cells and/or other particles and a second subset of droplets that do not include any cells and/or other particles. A given droplet in the first subset of droplets that includes one or more cells and/or other particles can comprise a sufficiently discrepant number or concentration of field-attractable particles than a given droplet in the second subset of droplets that does not include any cells and/or other particles such that when the plurality of droplets is subject to an electric or magnetic field, the first subset of droplets and the second subset of droplets are separated from each other. In some cases, when the plurality of droplets is subjected to an electric or magnetic field, singularly occupied droplets may be separated from unoccupied droplets and otherwise multiply occupied droplets.

In some instances, a plurality of droplets can be generated with or without field-attractable particles. A given droplet in the plurality of droplets may or may not include one or more cells and/or particles. Thus, the plurality of droplets can comprise a first subset of droplets that include one or more cells and/or particles and a second subset of droplets that do not include any cells and/or particles. The plurality of droplets can be subject to a pressure pulse and the first subset of droplets and the second subset of droplets can be separated from each other via hydrodynamic forces. In some cases, singularly occupied droplets may be separated from unoccupied droplets and otherwise multiply occupied droplets.

In an aspect, the methods and systems described herein provide for the compartmentalization, depositing, or partitioning of macromolecular constituent contents of individual biological particles from a sample material containing biological particles into discrete compartments or partitions (referred to interchangeably herein as partitions), where each partition maintains separation of its own contents from the contents of other partitions. The partition can be a droplet in an emulsion. The partition can be a well. The partition can be a bead, such as a gel bead and/or a cell bead. A partition may or may not contain biological particles and/or macromolecular constituents thereof. In accordance with some embodiments, each partition may contain at least some field attractable particles. The amount and/or concentration of field attractable particles in each partition can vary depending on whether the partition contains biological particles (or other particles, such as beads). In accordance with some other embodiments, a partition may not contain field attractable particles.

In some instances, unique identifiers, such as barcodes, may be previously, subsequently or concurrently delivered to the partitions that hold the compartmentalized or partitioned biological particle, in order to allow for the later attribution of the characteristics of the individual biological particle to the particular partition. Barcodes may be delivered, for example on an oligonucleotide, to a partition via any suitable mechanism. Barcoded oligonucleotides can be delivered to a partition via a microcapsule. In some cases, barcoded oligonucleotides can be initially associated with the microcapsule and then released from the microcapsule upon application of a stimulus which allows the oligonucleotides to dissociate or to be released from the microcapsule.

A microcapsule, in some instances, can comprise a bead. In some cases, a bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

In some instances, the bead may contain molecular precursors (e.g., monomers or polymers), which may form a polymer network via polymerization of the precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers.

A bead may comprise natural and/or synthetic materials. For example, a polymer can be a natural polymer or a synthetic polymer. In some cases, a bead can comprise both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some cases, a chemical cross-linker may be a precursor used to cross-link monomers during polymerization of the monomers and/or may be used to attach oligonucleotides (e.g., barcoded oligonucleotides) to the bead. In some cases, polymers may be further polymerized with a cross-linker species or other type of monomer to generate a further polymeric network. Non-limiting examples of chemical cross-linkers (also referred to as a "crosslinker" or a "cross-linker agent" herein) include cystamine, gluteraldehyde, dimethyl suberimidate, N-Hydroxysuccinimide crosslinker BS3, formaldehyde, carbodiimide (EDC), SMCC, Sulfo-SMCC, vinylsilane, N,N'diallyltartardiamide (DATD), N,N'-Bis(acryloyl)cystamine (BAC), or homologs thereof. In some cases, the crosslinker used in the present disclosure contains cystamine.

Crosslinking may be permanent or reversible, depending upon the particular crosslinker used. Reversible crosslinking may allow for the polymer to linearize or dissociate under appropriate conditions. In some cases, reversible crosslinking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and oligonucleotides. Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, the bead may comprise covalent or ionic bonds between polymeric precursors (e.g., monomers, oligomers, linear polymers), oligonucleotides, primers, and other entities. In some cases, the covalent bonds can be carbon-carbon bonds or thioether bonds.

In some cases, a bead may comprise an acrydite moiety, which in certain aspects may be used to attach one or more oligonucleotides (e.g., barcode sequence, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as an oligonucleotide (e.g., barcode sequence, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of oligonucleotides may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina® sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 19:
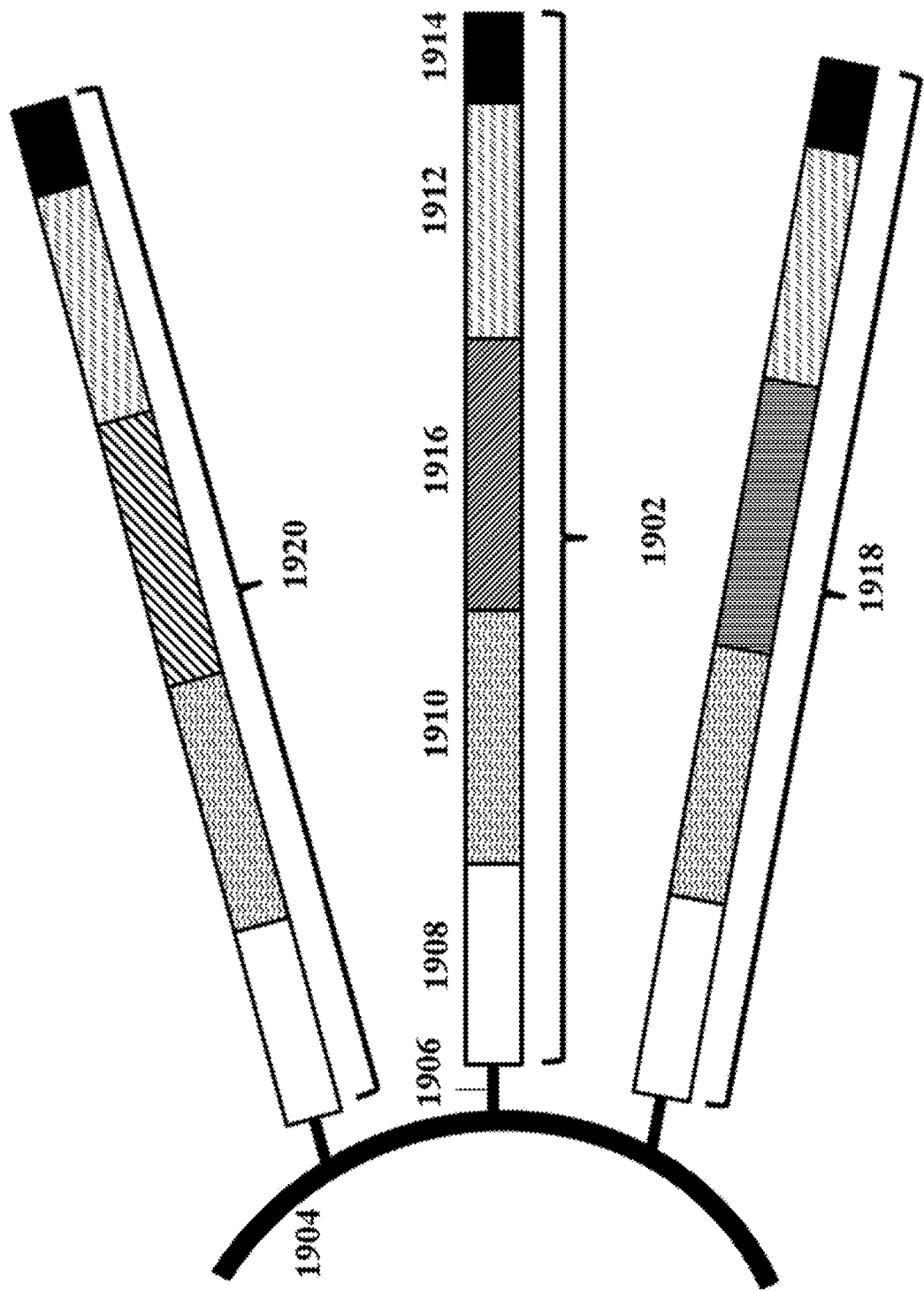
FIG. 19 illustrates an example of a barcode carrying bead.

FIG. 19 illustrates an example of a barcode carrying bead. A nucleic acid molecule 1902, such as an oligonucleotide, can be coupled to a bead 1904 by a releasable linkage 1906, such as, for example, a disulfide linker. The same bead 1904 may be coupled (e.g., via releasable linkage) to one or more other nucleic acid molecules 1918, 1920. The nucleic acid molecule 1902 may be or comprise a barcode. As noted elsewhere herein, the structure of the barcode may comprise a number of sequence elements. The nucleic acid molecule 1902 may comprise a functional sequence 1908 that may be used in subsequent processing. For example, the functional sequence 1908 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 1902 may comprise a barcode sequence 1910 for use in barcoding the sample (e.g., DNA, RNA, protein, etc.). In some cases, the barcode sequence 1910 can be bead-specific such that the barcode sequence 1910 is common to all nucleic acid molecules (e.g., including nucleic acid molecule 1902) coupled to the same bead 1904. Alternatively or in addition, the barcode sequence 1910 can be partition-specific such that the barcode sequence 1910 is common to all nucleic acid molecules coupled to one or more beads that are partitioned into the same partition. The nucleic acid molecule 1902 may comprise a specific priming sequence 1912, such as an mRNA specific priming sequence (e.g., poly-T sequence), a targeted priming sequence, and/or a random priming sequence. The nucleic acid molecule 1902 may comprise an anchoring sequence 1914 to ensure that the specific priming sequence 1912 hybridizes at the sequence end (e.g., of the mRNA). For example, the anchoring sequence 1914 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 1902 may comprise a unique molecular identifying sequence 1916 (e.g., unique molecular identifier (UMI)). In some cases, the unique molecular identifying sequence 1916 may comprise from about 5 to about 8 nucleotides. Alternatively, the unique molecular identifying sequence 1916 may compress less than about 5 or more than about 8 nucleotides. The unique molecular identifying sequence 1916 may be a unique sequence that varies across individual nucleic acid molecules (e.g., 1902, 1918, 1920, etc.) coupled to a single bead (e.g., bead 1904). In some cases, the unique molecular identifying sequence 1916 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 19 shows three nucleic acid molecules 1902, 1918, 1920 coupled to the surface of the bead 1904, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 1908, 1910, 1912, etc.) and variable or unique sequence segments (e.g., 1916) between different individual nucleic acid molecules coupled to the same bead.

In operation, a biological particle (e.g., cell, DNA, RNA, etc.) can be co-partitioned along with a barcode bearing bead 1904. The barcoded nucleic acid molecules 1902, 1918, 1920 can be released from the bead 1904 in the partition. By way of example, in the context of analyzing sample RNA, the poly-T segment (e.g., 1912) of one of the released nucleic acid molecules (e.g., 1902) can hybridize to the poly-A tail of a mRNA molecule. Reverse transcription may result in a cDNA transcript of the mRNA, but which transcript includes each of the sequence segments 1908, 1910, 1916 of the nucleic acid molecule 1902. Because the nucleic acid molecule 1902 comprises an anchoring sequence 1914, it will more likely hybridize to and prime reverse transcription at the sequence end of the poly-A tail of the mRNA. Within any given partition, all of the cDNA transcripts of the individual mRNA molecules may include a common barcode sequence segment 1910. However, the transcripts made from the different mRNA molecules within a given partition may vary at the unique molecular identifying sequence 1912 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by any swelling method as is known to one having skill in the art. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by any de-swelling method as is known to one having skill in the art. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to precursor, another species linked to a precursor, or a precursor itself comprises a labile bond, such as chemically, thermally, or photo-sensitive bonds e.g., disulfide bonds, UV sensitive bonds, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

Species that do not participate in polymerization may also be encapsulated in beads during bead generation (e.g., during polymerization of precursors). Such species may be entered into polymerization reaction mixtures such that generated beads comprise the species upon bead formation. In some cases, such species may be added to the gel beads after formation. Such species may include, for example, oligonucleotides, reagents for a nucleic acid amplification reaction (e.g., primers, polymerases, dNTPs, co-factors (e.g., ionic co-factors)) including those described herein, reagents for enzymatic reactions (e.g., enzymes, co-factors, substrates), or reagents for a nucleic acid modification reactions such as polymerization, ligation, or digestion. Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead.

Beads may be of uniform size or heterogeneous size. In some cases, the diameter of a bead may be at least about 1 micrometers (μm), 90 μm, 100 μm, 250 μm, 500 μm, 1 mm, or greater. In some cases, a bead may have a diameter of less than about 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

Beads may be of any suitable shape. Examples of bead shapes include, but are not limited to, spherical, non-spherical, oval, oblong, amorphous, circular, cylindrical, and variations thereof.

In addition to, or as an alternative to the cleavable linkages between the beads and the associated molecules, such as barcode containing oligonucleotides, described above, the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a oligonucleotide, e.g., barcoded oligonucleotide) may result in release of the species from the bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., an oligonucleotide, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent breaks the various disulfide bonds resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be desirable to avoid exposing such beads to the stimulus or stimuli that cause such degradation prior to the desired time, in order to avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

The methods, compositions, devices, and kits of this disclosure may be used with any suitable agent to degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

The compartments or partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can comprise droplets of aqueous fluid within a non-aqueous continuous phase, e.g., an oil phase. The partitions can comprise droplets of a first phase within a second phase, wherein the first and second phases are immiscible. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in detail in, e.g., U.S. Patent Application Publication No. 2010/0105112, which is entirely incorporated herein by reference for all purposes.

In the case of droplets in an emulsion, allocating individual biological particles to discrete partitions may generally be accomplished by introducing a flowing stream of biological particles in an aqueous fluid into a flowing stream of a non-aqueous fluid, such that droplets are generated at the junction of the two streams. By providing the aqueous stream at a certain concentration of biological particles, the occupancy of the resulting partitions (e.g., number of biological particles per partition) can be controlled. Where single biological particle partitions are desired, the relative flow rates of the immiscible fluids can be selected such that, on average, the partitions contain less than one biological particle per partition, in order to ensure that those partitions that are occupied, are primarily singularly occupied. In some embodiments, the relative flow rates of the fluids can be selected such that a majority of partitions are occupied, e.g., allowing for only a small percentage of unoccupied partitions. The flows and channel architectures can be controlled as to ensure a desired number of singularly occupied partitions, less than a certain level of unoccupied partitions and/or less than a certain level of multiply occupied partitions.

The systems and methods described herein can be operated such that a majority of occupied partitions include no more than one biological particle per occupied partition. In some cases, the partitioning process is conducted such that fewer than 25% of the occupied partitions contain more than one biological particle, and in many cases, fewer than 20% of the occupied partitions have more than one biological particle. In some cases, fewer than 10% or even fewer than 5% of the occupied partitions include more than one biological particle per partition.

In some cases, it is desirable to avoid the creation of excessive numbers of empty partitions. For example, from a cost perspective and/or efficiency perspective, it may desirable to minimize the number of empty partitions. However, while this may be accomplished by providing sufficient numbers of biological particles into the partitioning zone, the Poissonian distribution may expectedly increase the number of partitions that may include multiple biological particles. As such, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied. In some cases, the flow of one or more of the cells, or other fluids directed into the partitioning zone can be conducted such that, in many cases, no more than about 50% of the generated partitions, no more than about 25% of the generated partitions, or no more than about 10% of the generated partitions are unoccupied. These flows can be controlled so as to present non-Poissonian distribution of single occupied partitions while providing lower levels of unoccupied partitions. The above noted ranges of unoccupied partitions can be achieved while still providing any of the single occupancy rates described above. For example, in many cases, the use of the systems and methods described herein creates resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

After the partitions are generated, comprising in part singularly occupied partitions, in part multiply occupied partitions, and/or in part unoccupied partitions, the occupied partitions can be sorted from the unoccupied partitions. In some cases, singularly occupied partitions may be isolated from non-singularly occupied partitions (e.g., multiply occupied partitions and unoccupied partitions). Such sorting can be achieved by including field attractable particles during the generation of droplets in an emulsion. For example, a flowing stream of aqueous fluid containing biological particles and field attractable particles can be introduced into a flowing stream of a non-aqueous fluid, such that droplets are generated at the junction of the two streams.

As will be appreciated, the above-described occupancy rates are also applicable to partitions that include both biological particles and additional reagents, including, but not limited to, microcapsules carrying barcoded oligonucleotides. The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded oligonucleotides and a biological particle.

Although described in terms of providing substantially singularly occupied partitions, above, in certain cases, it is desirable to provide multiply occupied partitions, e.g., containing two, three, four or more cells and/or microcapsules (e.g., beads) comprising barcoded oligonucleotides within a single partition. Accordingly, as noted above, the flow characteristics of the biological particle and/or bead containing fluids and partitioning fluids may be controlled to provide for such multiply occupied partitions. In particular, the flow parameters may be controlled to provide a desired occupancy rate at greater than about 50% of the partitions, greater than about 75%, and in some cases greater than about 80%, 90%, 95%, or higher.

In some cases, additional microcapsules are used to deliver additional reagents to a partition. In such cases, it may be advantageous to introduce different beads into a common channel or droplet generation junction, from different bead sources, i.e., containing different associated reagents, through different channel inlets into such common channel or droplet generation junction. In such cases, the flow and frequency of the different beads into the channel or junction may be controlled to provide for the desired ratio of microcapsules from each source, while ensuring the desired pairing or combination of such beads into a partition with the desired number of biological particles.

The partitions described herein may comprise small volumes, e.g., less than about 10 microliters (μL), 5 μL, 1 μL, 900 picoliters (μL), 800 μL, 700 μL, 600 μL, 500 μL, 400 μL, 300 μL, 200 μL, 100 μL, 50 μL, 20 μL, 10 μL, 1 μL, 500 nanoliters (nL), 100 nL, 50 nL, or less.

For example, in the case of droplet based partitions, the droplets may have overall volumes that are less than about 1000 μL, 900 μL, 800 μL, 700 μL, 600 μL, 500 μL, 400 μL, 300 μL, 200 μL, 100 μL, 50 μL, 20 μL, 10 μL, 1 μL, or less. Where co-partitioned with microcapsules, it will be appreciated that the sample fluid volume, e.g., including co-partitioned biological particles, within the partitions may be less than about 90% of the above described volumes, less than about 80%, less than about 70%, less than about 60%, less than about 50%, less than about 40%, less than about 30%, less than about 20%, or less than about 10% the above described volumes.

As is described elsewhere herein, partitioning species may generate a population or plurality of partitions. In such cases, any suitable number of partitions can be generated to generate the plurality of partitions. For example, in a method described herein, a plurality of partitions may be generated that comprises at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more. Moreover, the plurality of partitions may comprise both unoccupied partitions (e.g., empty partitions) and occupied partitions.

Microfluidic channel networks can be utilized to generate partitions as described herein. Alternative mechanisms may also be employed in the partitioning of individual biological particles, including porous membranes through which aqueous mixtures of cells are extruded into non-aqueous fluids.

FIG. 1 shows an example of a microfluidic channel structure for partitioning individual biological particles. As described elsewhere herein, in some cases, the majority of occupied partitions can include no more than one biological particle per occupied partition and, in some cases, some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

As shown in FIG. 1, the channel structure can include channel segments 102, 104, 106 and 108 communicating at a channel junction 110. In operation, a first aqueous fluid 112 that includes suspended biological particles (e.g., cells) 114 and suspended field-attractable particles 115, may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. A discrete droplet generated may include an individual biological particle 114 and field-attractable particles 115 (such as droplets 118). A discrete droplet generated may include more than one individual biological particle 114 and field-attractable particles 115 (not shown in FIG. 1). A discrete droplet may contain field-attractable particles 115 but no biological particle 114 (such as droplet 120).

The field-attractable particles 115 may be paramagnetic particles. In some cases, the field-attractable particles may be superparamagnetic particles. For example, the field-attractable particles can comprise polystyrene magnetic particles (e.g., polystyrene core particle coated with at least a layer of magnetite (e.g., iron oxide) and polystyrene), amino magnetic particles, carboxyl magnetic particles, dimethylamino magnetic particles, hydroxyethyl magnetic particles, and/or a combination of the above. A paramagnetic particle can comprise a polymer matrix of amine silane, glucuronic acid, bromoacetyl, chitosan, carboxymethyldextran, citric acid, starch, DEAE-starch, phosphate-starch, dextran, dextran-sulfate, lipid, oleic acid, diphosphate, polyaspartic acid, polyacrylamide, polyacrylic acid, polydimethylamine, polyethylene glycole alpha-methoxy-omega-amine, polyethylene glycol alpha-,omega-diphosphate, poly(maleic acid-co-olefin), polystyrenesulfonate, polyvinyl alcohol, poly(4-vinylpyridine), poly-diallyldimethylamin, uncoated magnetite, and/or other matrices. A paramagnetic particle may have micrometer or nanometer size. For example, a paramagnetic particle can have a maximum dimension (e.g., width, length, height, diameter, etc.) of at most about 20 micrometers (µm), 10 µm, 9 µm, 8 µm, 7 µm, 6 µm, 5 µm, 4 µm, 3 µm, 2 µm, 1 µm, 0.5 µm, or less. The paramagnetic particle can have a maximum dimension of at most about 500 nanometer (nm), 400 nm, 300 nm, 200 nm, 100 nm, 50 nm, 40 nm, 30 nm, 20 nm, 10 nm, 9 nm, 8 nm, 7 nm, 6 nm, 5 nm, 4 nm, 3 nm, 2 nm, 1 nm, or less. Alternatively, a paramagnetic particle can have a maximum dimension that is greater than about 20 µm. The paramagnetic particles may be responsive when exposed to magnetic fields. In some cases, the paramagnetic particles can be smooth surface particles, wherein a thick polymer layer coats the magnetite (e.g., iron oxide) layer. The smooth surface can shield the magnetite from interfering with enzyme activities or other undesirable effects with other particles or cells caused by exposure to the magnetite. In some cases, the paramagnetic particles can be cross-linked particles, wherein the particles are coated with cross-linked polymer on the surfaces of the iron oxide crystals. The cross-linked polymer can render the paramagnetic particle resistant to common organic solvents, such as acetone, acetonitrile, dimethylformanide (DMF) and chloroform. The magnetite content on each paramagnetic particle can be adjusted (e.g., to have higher or lower percentage) to be more responsive or less responsive to the same magnetic field. In some cases, the field-attractable particles can be diamagnetic particles or ferromagnetic particles.

In some cases, the field-attractable particles 115 may be conductive particles. A conductive particle may have micrometer or nanometer size. For example, a conductive particle can have a maximum dimension (e.g., width, length, height, diameter, etc.) of at most about 20 micrometers (µm), 10 µm, 9 µm, 8 µm, 7 µm, 6 µm, 5 µm, 4 µm, 3 µm, 2 µm, 1 µm, 0.5 µm, or less. The conductive particle can have a maximum dimension of at most about 500 nanometer (nm), 400 nm, 300 nm, 200 nm, 100 nm, 50 nm, 40 nm, 30 nm, 20 nm, 10 nm, 9 nm, 8 nm, 7 nm, 6 nm, 5 nm, 4 nm, 3 nm, 2 nm, 1 nm, or less. Alternatively, a conductive particle can have a maximum dimension that is greater than about 20 µm. A conductive particle can have a substantially spherical shape. Alternatively, a conductive particle can have a different shape. The conductive particles may be responsive when exposed to electric fields. The conductive (e.g., metal) content on each conductive particle can be adjusted (e.g., to have higher or lower percentage) to be more responsive or less responsive to the same electric field. In some cases, the field-attractable particles 115 can comprise both paramagnetic and conductive particles.

The first aqueous fluid 112 can have a substantially uniform concentration of field-attractable particles 115 as the first aqueous fluid 112 is introduced into junction 110. For example, the concentration of the field-attractable particles 115 in the first aqueous fluid 112 in the channel segment 102 at time x can be substantially uniform with the concentration of field-attractable particles 115 in the first aqueous fluid 112 in the channel segment 102 at time x+δ (where x and δ are positive). In some instances, the concentration of field-attractable particles 115 can be substantially uniform in only the volume of the first aqueous fluid 112, that is, the volume not including the volume of each of the biological particles 114 suspended in the first aqueous fluid 112.

This second fluid 116 can comprise an oil, such as a fluorinated oil, that includes a fluorosurfactant for stabilizing the resulting droplets, e.g., inhibiting subsequent coalescence of the resulting droplets. Examples of particularly useful partitioning fluids and fluorosurfactants are described for example, in U.S. Patent Application Publication No. 2010/0105112, which is entirely incorporated herein by reference for all purposes.

The generated droplets may comprise two subsets of droplets: (1) occupied droplets 118, containing one or more biological particles 114, and (2) unoccupied droplets 120, not containing any biological particles 114. Each droplet generated, occupied or unoccupied, may contain some number and/or concentration of field-attractable particles 115. In some instances, the concentration of the field-attractable particles 115 in each of the unoccupied droplets 120 can be substantially uniform, wherein the concentration is a number of field-attractable particles per total droplet volume (and not just the volume of the first aqueous fluid 112 in the droplet). In some instances, the concentration of the field-attractable particles 115 in each of the occupied droplets 118 can be substantially uniform, wherein the concentration is a number of field-attractable particles per total droplet volume. In other instances, as can be easily appreciated, the concentration of the field-attractable particles 115 in each of the occupied droplets 118 can vary with size and/or the number of biological particles 114 contained in the droplet. In any case, the concentration of field-attractable particles in any of the unoccupied droplets 120 can be greater than the concentration of field-attractable particles in any of the occupied droplets 118 to account for the volume occupied by the biological particle 114 in the occupied droplets 118. In most cases, the concentration of field-attractable particles in a droplet from the unoccupied droplets 120 can be greater than the concentration of field-attractable particles in a droplet from the occupied droplets 118 to account for the volume occupied by the biological particle 114 in the occupied droplets 118.

For example, assuming that (i) the droplet is spherical and has the radius $R_D$, (ii) a biological particle is spherical and has the radius $R_+$, and (iii) the concentration of field-attractable particles in the volume of aqueous fluid is substantially uniform, the ratio of a number of field-attractable particles in a singularly occupied droplet ($N_+$) to a number of field-attractable particles in an unoccupied droplet (N) will be:

$$\frac{N_+}{N_-} = 1 - \left(\frac{R_+}{R_D}\right)^3$$

As can be appreciated, the above ratio may change with deviations from the above assumptions. For example, an occupied droplet containing three biological particles can have a ratio of about:

$$1 - 3\left(\frac{R_+}{R_D}\right)^3.$$

In another aspect, in addition to or as an alternative to droplet based partitioning, biological particles may be encapsulated within a microcapsule, such as a cell bead, that comprises an outer shell or layer or porous matrix in which is entrained one or more individual biological particles or small groups of biological particles, and may include other reagents. Encapsulation of biological particles may be performed by a variety of processes. Such processes combine an aqueous fluid containing the biological particles and also containing the field-attractable particles to be analyzed with a polymeric precursor material that may be capable of being formed into a gel or other solid or semi-solid matrix upon application of a particular stimulus to the polymer precursor. Such stimuli include, e.g., thermal stimuli (either heating or cooling), photo-stimuli (e.g., through photo-curing), chemical stimuli (e.g., through crosslinking, polymerization initiation of the precursor (e.g., through added initiators), or the like.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein, such as to generate a plurality of particles, each particle comprising field-attractable particles. The plurality of particles may comprise a first subset of particles occupied by biological particles (e.g., cell beads) and a second subset of particles unoccupied by biological particles. In particular, and with reference to FIG. 1, the aqueous fluid comprising (i) the biological particles 114, (ii) the field-attractable particles 115, and (ii) the polymer precursor material (not shown) is flowed into channel junction 110, where it is partitioned into droplets 118 or 120 comprising or not comprising the individual biological particles 114, respectively, but always comprising the field-attractable particles 115, through the flow of non-aqueous fluid 116. In the case of encapsulation methods, non-aqueous fluid 116 may also include an initiator to cause polymerization and/or cross-linking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, e.g., a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethyl-methylenediamine (TEMED) may be provided within the second fluid streams in channel segments 104 and 106, which initiates the copolymerization of the acrylamide and BAC into a cross-linked polymer network or, hydrogel. Upon contact of the second fluid stream 116 with the first fluid stream 112 at junction 110 in the formation of droplets, the TEMED may diffuse from the second fluid 116 into the aqueous first fluid 112 comprising the linear polyacrylamide, which will activate the crosslinking of the polyacrylamide within the droplets, resulting in the formation of the gel, e.g., hydrogel, microcapsules (e.g., droplet 118, 120), as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions, e.g., $Ca^{2+}$, can be used as an encapsulation process using the described processes. Likewise, agarose droplets may also be transformed into capsules through temperature based gelling, e.g., upon cooling, or the like. In some cases, encapsulated biological particles can be selectively releasable from the microcapsule, e.g., through passage of time, or upon application of a particular stimulus, that degrades the microcapsule sufficiently to allow the cell, or its contents to be released from the microcapsule, e.g., into a partition, such as a droplet. For example, in the case of the polyacrylamide polymer described above, degradation of the microcapsule may be accomplished through the introduction of an appropriate reducing agent, such as DTT or the like, to cleave disulfide bonds that cross link the polymer matrix (See, e.g., U.S. Patent Application Publication No. 2014/0378345, which is entirely incorporated herein by reference for all purposes).

Encapsulated biological particles (e.g., cell beads) can provide certain potential advantages of being storable, and more portable than droplet based partitioned biological particles. Furthermore, in some cases, it may be desirable to allow biological particles to be analyzed to incubate for a select period of time, in order to characterize changes in such biological particles over time, either in the presence or absence of different stimuli. In such cases, encapsulation of individual biological particles may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively, encapsulated biological particles may be readily deposited into other partitions, e.g., droplets, as described above.

In accordance with certain aspects, the biological particles may be partitioned along with lysis reagents in order to release the contents of the biological particles within the partition. In such cases, the lysis agents can be contacted with the biological particle suspension concurrently with, or immediately prior to the introduction of the biological particles into the partitioning junction/droplet generation zone, e.g., through an additional channel or channels upstream of channel junction 110. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the biological particles to cause the release of the biological particles's contents into the partitions. For example, in some cases, surfactant based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a desired size, following cellular disruption.

In addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of oligonucleotides from their respective microcapsule (e.g., bead). In alternative aspects, this may be a different and non-overlapping stimulus, in order to allow an encapsulated biological particle to be released into a partition at a different time from the release of oligonucleotides into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes, can be assigned or associated with individual biological particles or populations of biological particle, in order to tag or label the biological particle's macromolecular components (and as a result, its characteristics) with the unique identifiers. These unique identifiers can then be used to attribute the biological particle's components and characteristics to an individual biological particle or group of biological particles. In some aspects, this is performed by co-partitioning the individual biological particle or groups of biological particles with the unique identifiers. In some aspects, the unique identifiers are provided in the form of oligonucleotides that comprise nucleic acid barcode sequences that may be attached to or otherwise associated with the nucleic acid contents of individual biological particle, or to other components of the biological particle, and particularly to fragments of those nucleic acids. The oligonucleotides are partitioned such that as between oligonucleotides in a given partition, the nucleic acid barcode sequences contained therein are the same, but as between different partitions, the oligonucleotides can, and do, have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

The co-partitioned oligonucleotides can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads (e.g., see FIG. 19), are provided that each includes large numbers of the above described barcoded oligonucleotides releasably attached to the beads, where all of the oligonucleotides attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the oligonucleotides into the partitions, as they are capable of carrying large numbers of oligonucleotide molecules, and may be configured to release those oligonucleotides upon exposure to a particular stimulus, as described elsewhere herein. In some cases, the population of beads will provide a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of oligonucleotide molecules attached. In particular, the number of molecules of oligonucleotides including the barcode sequence on an individual bead can be at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules, or more.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules.

In some cases, it may be desirable to incorporate multiple different barcodes within a given partition, either attached to a single or multiple beads within the partition. For example, in some cases, a mixed, but known barcode sequences set may provide greater assurance of identification in the subsequent processing, e.g., by providing a stronger address or attribution of the barcodes to a given partition, as a duplicate or independent confirmation of the output from a given partition.

The oligonucleotides are releasable from the beads upon the application of a particular stimulus to the beads. In some cases, the stimulus may be a photo-stimulus, e.g., through cleavage of a photo-labile linkage that releases the oligonucleotides. In other cases, a thermal stimulus may be used, where elevation of the temperature of the beads environment will result in cleavage of a linkage or other release of the oligonucleotides form the beads. In still other cases, a chemical stimulus is used that cleaves a linkage of the oligonucleotides to the beads, or otherwise results in release of the oligonucleotides from the beads. In one case, such compositions include the polyacrylamide matrices described above for encapsulation of biological particles, and may be degraded for release of the attached oligonucleotides through exposure to a reducing agent, such as DTT.

For example, in FIG. 1, concurrent to the stream of the first aqueous fluid 112 flowing through channel 102 towards the junction 110, a second aqueous stream comprising barcode carrying beads suspended in a third fluid can be flowed through another channel (not shown in FIG. 1) towards the junction 110. The third fluid can be the same fluid material as the first aqueous fluid 112. A non-aqueous partitioning fluid 116 is introduced into channel junction 110 from each of side channels 104 and 106, and the combined streams are flowed into outlet channel 108. Within channel junction 110, the two combined aqueous streams from channel segments 102 and the other channel carrying the third fluid are combined, and partitioned into droplets 118, 120. The occupied droplets may contain either one or more biological particles, either one or more barcode carrying beads, or both at least a biological particle and at least a barcode carrying bead. The unoccupied droplets may contain neither biological particles nor barcode carrying beads. However, all droplets, both occupied and unoccupied droplets, can comprise at least some concentration of field-attractable particles 115. As noted previously, by controlling the flow characteristics of each of the fluids combining at channel junction 110, as well as controlling the geometry of the channel junction, partitioning can be optimized to achieve a desired occupancy level of beads, biological particles, or both, within the partitions that are generated.

In some cases, assuming that (i) the droplet is spherical and has the radius $R_D$, (ii) a biological particle is spherical and has the radius $R_+$, (iii) a barcode carrying bead is spherical and has the radius $R_B$ and (iv) the concentration of field-attractable particles in the volume of aqueous fluid is substantially uniform, the ratio of a number of field-attractable particles in a singularly occupied droplet ($N_{+,B}$) (containing one of each of a biological particle and a barcode carrying bead) to a number of field-attractable particles in an unoccupied droplet ($N_-$) will be:

$$\frac{N_{+,B}}{N_-} = 1 - \left(\frac{R_+}{R_D}\right)^3 - \left(\frac{R_B}{R_D}\right)^3$$

Figure 2A:
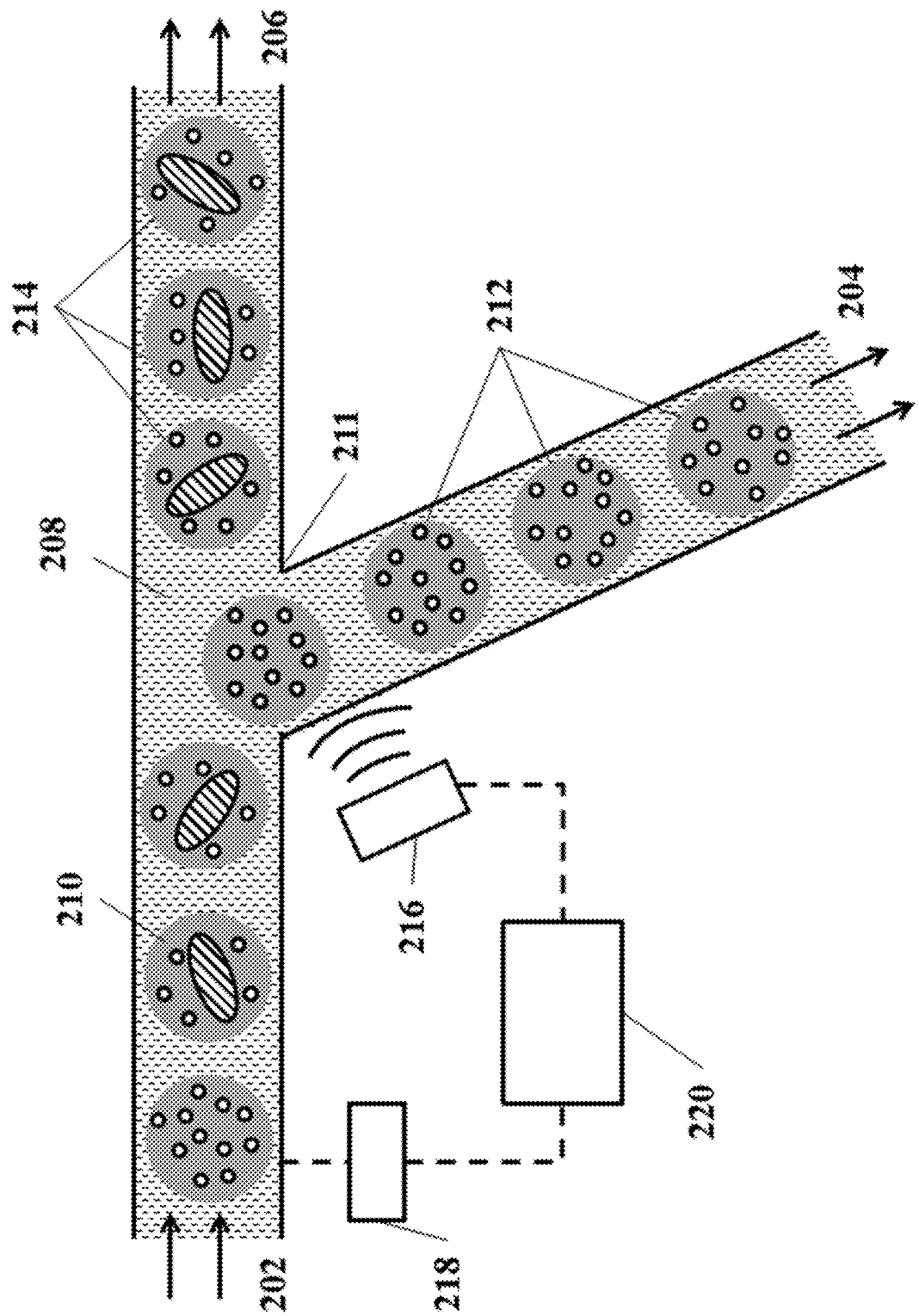
FIG. 2A shows an example of a microfluidic channel structure for separating occupied droplets from unoccupied droplets.

FIG. 2A shows an example of a microfluidic channel structure for separating occupied droplets from unoccupied droplets. As described elsewhere herein, when droplets are generated, there may be a first subset population of occupied droplets containing one or more biological particles and a second subset population of unoccupied droplets not containing any biological particles. In some cases, the droplets may additionally contain one or more barcode carrying beads. For example, a droplet may have only a biological particle, a droplet may have only a barcode carrying bead, a droplet may have both a biological particle and a barcode carrying bead, or a droplet may have neither biological particles nor barcode carrying beads. In some cases, the majority of occupied partitions can include no more than one biological particle per occupied partition and, in some cases, some of the generated partitions can be unoccupied (of any biological particle). In some cases, though, some of the occupied partitions may include more than one biological particle. In some cases, the partitioning process may be controlled such that fewer than 25% of the occupied partitions contain more than one biological particle, and in many cases, fewer than 20% of the occupied partitions have more than one biological particle, while in some cases, fewer than 10% or even fewer than 5% of the occupied partitions include more than one biological particle per partition.

As shown in FIG. 2A, the channel structure can include channel segments 202, 204, and 206 meeting at a channel intersection 211. In some instances, the outflow channel 108 of the emulsion carrying the generated droplets in FIG. 1 can be upstream of the channel segment 202, such that the generated droplets are directed to flow to the channel intersection 211 for subsequent sorting. A controller 220 can be operatively coupled to a fluid flow unit 218, to facilitate flow of fluid in the channel structure, and a field application unit 216, to apply one or more fields to the channel structure.

In operation, a plurality of discrete droplets, each comprising a first aqueous fluid 210 can flow as emulsions in a second fluid 208, wherein the second fluid 208 is immiscible to the first aqueous fluid 210. The droplets being transported along channel segment 202 into intersection 211 can comprise a first subset of droplets 214 that are each occupied with at least a biological particle and/or a barcode carrying bead and a second subset of droplets 212 that are each unoccupied. Every droplet, including occupied and unoccupied droplets, can comprise some concentration of field-attractable particles. As described above, a given unoccupied droplet can have a higher concentration of field-attractable particles than a given occupied droplet to account for the volume occupied by a biological particle and/or a barcode bead in an occupied droplet.

After sorting at or near the intersection 211, the first subset of droplets 214 can be directed to flow along channel segment 206 and away from the intersection 211, and the second subset of droplets 212 can be directed to flow along channel segment 204 and away from the intersection 211.

The fluid flow unit 218 can be configured to subject the second fluid 208 containing a plurality of droplets, including both occupied droplets and unoccupied droplets, to flow along the channel 202 towards the intersection 211. The fluid flow unit 218 can be configured to subject the second fluid 208 containing a plurality of droplets, wherein a majority of the droplets is unoccupied droplets, to flow along the channel 204 away from the intersection 211. The fluid flow unit 218 can be configured to subject the second fluid 208 containing a plurality of droplets, wherein a majority of the droplets is occupied droplets, to flow along the channel 206 away from the intersection 211. Alternatively, the fluid flow unit 218 can be configured to subject the second fluid 208 containing a plurality of droplets, wherein a majority of the droplets is unoccupied droplets, to flow along the channel 206 away from the intersection 211, and configured to subject the second fluid 208 containing a plurality of droplets, wherein a majority of the droplets is occupied droplets, to flow along the channel 204 away from the intersection 211. The fluid flow unit 218 can be operatively coupled to the controller 220. For example, the fluid flow unit 218 may receive instructions from the controller 220 regarding fluid pressure and/or velocity.

In some instances, the fluid flow unit 218 may comprise a compressor to provide positive pressure at an upstream location to direct the fluid from the upstream location to flow to a downstream location. In some instances, the fluid flow unit 218 may comprise a pump to provide negative pressure at a downstream location to direct the fluid from an upstream location to flow to the downstream location. In some instances, the fluid flow unit 218 may comprise both a compressor and a pump, each at different locations. In some instances, the fluid flow unit 218 may comprise different devices at different locations. The fluid flow unit 218 may comprise an actuator. While FIG. 2A depicts one fluid flow unit 218, it may be appreciated that there may be a plurality of fluid flow units 218, each in communication with the controller 220 and/or with each other. For example, there can be a separate fluid flow unit to direct the fluid in channel 202 towards the intersection 211, a separate fluid flow unit to direct the fluid in channel 204 away from the intersection 211, and a separate fluid flow unit to direct the fluid in channel 206 away from the intersection 211.

The field application unit 216 can be configured to apply a force field to the channel structure. In some instances, the field application unit 216 can be configured to apply a force field at or near the intersection 211 such that the second subset of droplets (unoccupied droplets) are generally directed along the channel segment 204 and away from the intersection 211, and the first subset of droplets (occupied droplets) are generally directed along the channel segment 206 and away from the intersection 211, thereby isolating the two subsets of droplets.

For example, the field application unit 216 can apply a magnetic field at or near the intersection 211. The field application unit 216 can be a magnet and/or a circuit (e.g., current carrying device) configured to generate a magnetic field. On account of each droplet containing field-attractable particles (e.g., paramagnetic particles), each droplet may be attracted (e.g., due to paramagnetic particles) or repelled (e.g., due to diamagnetic particles) to or away, respectively, from the magnetic field. The degree of attraction (or repulsion) can be proportional to a number (and/or a concentration) of field-attractable particles in each droplet. That is, the magnetic force acting on a droplet, from the same magnetic field, can be proportional to a number (and/or a concentration) of field-attractable particles in the droplet. As previously described above, assuming that (i) the droplet is spherical and has the radius $R_D$, (ii) a biological particle is spherical and has the radius $R_+$, and (iii) the concentration of field-attractable particles in the volume of aqueous fluid is substantially uniform, the ratio of a number of field-attractable particles in a singularly occupied droplet ($N_+$) (wherein the occupied droplet contains a single biological particle) to a number of field-attractable particles in an unoccupied droplet ($N_-$) will be, and thus the ratio of a magnetic force acting on a singularly occupied droplet ($F_{M+}$) to a magnetic force acting on an unoccupied droplet ($F_{M-}$) will be:

$$\frac{N_+}{N_-} = \frac{F_{M+}}{F_{M-}} = 1 - \left(\frac{R_+}{R_D}\right)^3$$

That is, there may be a stronger (differential) force acting on a given unoccupied droplet than a given occupied droplet. As can be appreciated, the above ratio may change with deviations from the above assumptions (e.g., non-spherical biological particle, non-spherical droplet, non-uniform concentration of field-attractable particles in volume of aqueous fluid, etc.).

In another example, the field application unit 216 can apply an electric field at or near the intersection 211. On account of each droplet containing field-attractable particles (e.g., conductive particles), each droplet may be attracted or repelled to or away, respectively, from the electric field. The degree of attraction (or repulsion) can be proportional to a number (and/or a concentration) of field-attractable particles in each droplet. That is, the electric force acting on a droplet, from the same electric field, can be proportional to a number (and/or a concentration) of field-attractable particles in the droplet. As previously described above, assuming that (i) the droplet is spherical and has the radius $R_D$, (ii) a biological particle is spherical and has the radius $R_+$, and (iii) the concentration of field-attractable particles in the volume of aqueous fluid is substantially uniform, the ratio of a number of field-attractable particles in a singularly occupied droplet ($N_+$) (wherein the occupied droplet contains a single biological particle) to a number of field-attractable particles in an unoccupied droplet ($N_-$) will be, and thus the ratio of an electric force acting on a singularly occupied droplet ($F_{E+}$) to an electric force acting on an unoccupied droplet ($F_E$) will be:

$$\frac{N_+}{N_-} = \frac{F_{E+}}{F_{E-}} = 1 - \left(\frac{R_+}{R_D}\right)^3$$

As can be appreciated, the above ratio may change with deviations from the above assumptions (e.g., non-spherical biological particle, non-spherical droplet, non-uniform concentration of field-attractable particles in volume of aqueous fluid, etc.). In some instances, the fluid flow unit 218 can apply both an electric field and a magnetic field.

The field application unit 216 can be operatively coupled to the controller 220. For example, the field application unit 216 may receive instructions from the controller 220 regarding force field strength, orientation, frequency, and/or other variables. While FIG. 2A depicts one field application unit 216, it may be appreciated that there may be a plurality of field application units 216, each in communication with the controller 220, other controllers, and/or with each other. For example, there can be a plurality of field application units, each located at a different location. The controller 220 may instruct the field application unit 216 to apply a force field sufficiently strong and in a sufficiently targeted direction towards the mixed (occupied and unoccupied) droplets such as to direct the unoccupied droplets in one channel and direct the occupied droplets to another channel. In an example, the field application unit 216 can be placed in a location closer to a first channel (e.g., channel 204) than a second channel (e.g., channel 206) to direct the unoccupied droplets (which are subject to a stronger force from the same field) to the first channel, assuming that the field is strongest when closest to the field application unit 216. The stronger a force from the field acts on a droplet, the more likely that the droplet will deviate from an initial flow direction (e.g., direction of flow in channel 202) into another channel having another direction. In some instances, the field application unit may be located at least in part downstream, from the intersection 211, of a channel intended to isolate unoccupied droplets (e.g., channel 204).

For example, a force field applied can be strong enough to direct the unoccupied droplets to flow to a first channel but weak enough to direct (or leave be) the occupied droplets to flow to a second channel. In some instances, a magnetic field applied by the field application unit 216 can have a magnetic flux density range from at least about $10^{-5}$ Teslas (T) to about 1 T. Alternatively, the magnetic flux density can be less than or equal to about $10^{-5}$ T and/or greater than or equal to about 1 T. In some instances, an electric field applied by the field application unit 216 can have an electric field strength of at least about 1 volt per meter (V/m), 2 V/m, 3 V/m, 4 V/m, 5 V/m, 10 V/m, or more. Alternatively, the electric field strength can be less than about 10 V/m, 5 V/m, 4 V/m, 3 V/m, 2 V/m, 1 V/m, or less.

Figure 2B:
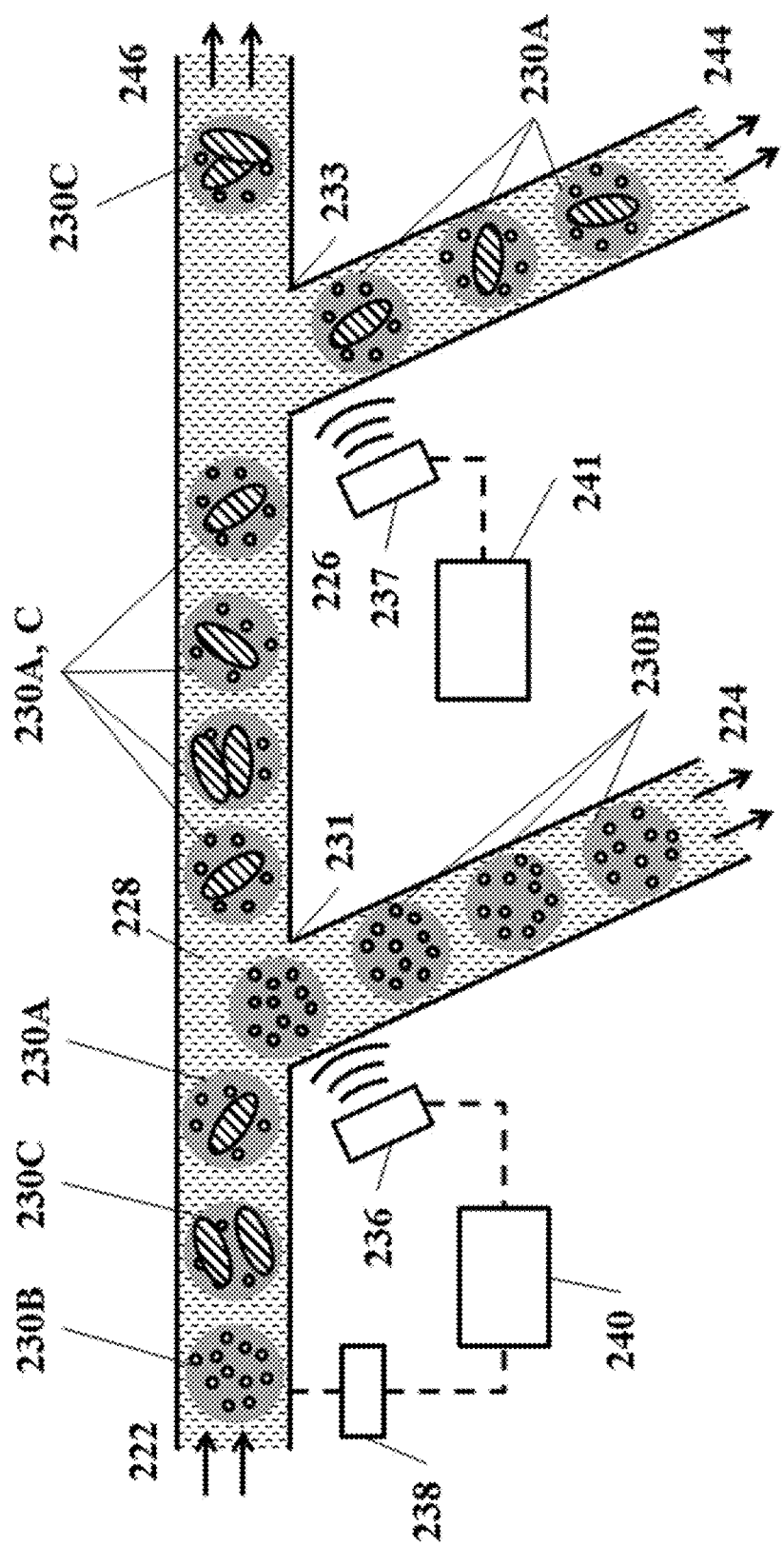
FIG. 2B shows an example of a multi-stage microfluidic channel structure for separating singularly occupied droplets.

FIG. 2B shows an example of a multi-stage microfluidic channel structure for separating singularly occupied droplets. As described elsewhere herein, when droplets are generated, there may be a first subset population of occupied droplets containing a single biological particle (e.g., cell), a second subset population of unoccupied droplets not containing any biological particles, and a third subset population of occupied droplets containing multiple (e.g., two or more) biological particles. In some cases, the droplets may additionally contain one or more barcode carrying beads. For example, a droplet may have only biological particle(s), a droplet may have only barcode carrying bead(s), a droplet may have both biological particle(s) and barcode carrying bead(s), or a droplet may have neither biological particle(s) nor barcode carrying bead(s). The generated droplets may be sorted to isolate the first subset population, second subset population, and third subset population in multiple stages.

As shown in FIG. 2B, the channel structure can include channel segments 222, 224, 226, 244, and 246. Channel segments 222, 224, and 226 may meet at channel intersection 231. Channel segments 226, 244, and 246 may meet at channel intersection 233. In some instances, the outflow channel 108 of the emulsion carrying the generated droplets in FIG. 1 can be upstream of the channel segment 222, such that the generated droplets are directed to flow to the channel intersection 231 for subsequent sorting. The generated droplets may comprise a first subset population of singularly occupied droplets (e.g., 230A), a second subset population of unoccupied droplets (e.g., 230B), and a third subset population of multiply occupied droplets (e.g., 230C). A first controller 240 can be operatively coupled to a fluid flow unit 238, to facilitate flow of fluid in the channel structure, and a first field application unit 236, to apply one or more fields to the channel structure. A second controller 241 can be operatively coupled to a second field application unit 237, to apply one or more fields to the channel structure.

In operation, a plurality of discrete droplets can flow as emulsions in a fluid 228. The droplets being transported along channel segment 222 into intersection 231 can comprise the first subset population of singularly occupied droplets (e.g., 230A), the second subset population of unoccupied droplets (e.g., 230B), and the third subset population of multiply occupied droplets (e.g., 230C). Every droplet, including singularly occupied, multiply occupied, and unoccupied droplets, can comprise some concentration of field-attractable particles. As described above, a given unoccupied droplet can have a higher concentration of field-attractable particles than a given occupied droplet to account for the volume occupied by a biological particle and/or a barcode bead in an occupied droplet. Within occupied droplets, a given singly occupied droplet can have a higher concentration of field-attractable particles than a given multiply occupied droplet to account for the differential volume occupied by the different numbers of biological particles (and/or barcode beads) in the droplet.

After a first stage of sorting at or near the intersection 231, the first and third subsets of droplets (e.g., 230A, C) can be directed to flow along channel segment 226 and away from the intersection 231, and the second subset of droplets 230B can be directed to flow along channel segment 224 and away from the intersection 231.

The fluid flow unit 238 can be configured to subject the fluid 228 containing a plurality of droplets including the occupied and/or unoccupied droplets (e.g., as emulsion suspensions) to or from intersections 231, 233 along channel segments 222, 224, 226, 244, and 246. The fluid flow unit 238 can be operatively coupled to the first controller 240.

For example, the fluid flow unit 238 may receive instructions from the first controller 240 regarding fluid pressure and/or velocity.

In some instances, the fluid flow unit 238 may comprise a compressor to provide positive pressure at an upstream location to direct the fluid from the upstream location to flow to a downstream location. In some instances, the fluid flow unit 238 may comprise a pump to provide negative pressure at a downstream location to direct the fluid from an upstream location to flow to the downstream location. In some instances, the fluid flow unit 238 may comprise both a compressor and a pump, each at different locations. In some instances, the fluid flow unit 238 may comprise different devices at different locations. The fluid flow unit 238 may comprise an actuator. While FIG. 2B depicts one fluid flow unit 238, it may be appreciated that there may be a plurality of fluid flow units 238, each in communication with the first controller 240, other controllers (e.g., second controller 241), and/or with each other. For example, there can be a separate fluid flow unit to direct the fluid in channel 222 towards the intersection 231, a separate fluid flow unit to direct the fluid in channel 224 away from the intersection 231, and a separate fluid flow unit to direct the fluid in channel 226 away from the intersection 231.

The first field application unit 236 can be configured to apply a force field to the channel structure. In some instances, the field application unit 236 can be configured to apply a force field at or near the intersection 231 such that the second subset of droplets (unoccupied droplets) are generally directed along the channel segment 224 and away from the intersection 231, and the first and third subset of droplets (occupied droplets) are generally directed along the channel segment 226 and away from the intersection 231, thereby separating the subsets of droplets. For example, as described elsewhere herein, the first field application unit 236 may apply a magnetic field at or near the intersection 231. On account of each droplet containing field-attractable particles (e.g., paramagnetic particles), each droplet may be attracted (e.g., due to paramagnetic particles) or repelled (e.g., due to diamagnetic particles) to or away, respectively, from the magnetic field. The degree of attraction (or repulsion) can be proportional to a number (and/or a concentration) of field-attractable particles in each droplet. That is, the magnetic force acting on a droplet, from the same magnetic field, can be proportional to a number (and/or a concentration) of field-attractable particles in the droplet. As described above, assuming that (i) the droplet is spherical and has the radius $R_D$, (ii) a biological particle is spherical and has the radius $R_+$, and (iii) the concentration of field-attractable particles in the volume of aqueous fluid is substantially uniform, the ratio of a number of field-attractable particles in a singularly occupied droplet ($N_+$) (wherein the occupied droplet contains a single biological particle) to a number of field-attractable particles in an unoccupied droplet (N) will be, and thus the ratio of a magnetic force acting on a singularly occupied droplet ($F_{M+}$) to a magnetic force acting on an unoccupied droplet ($F_{M-}$) will be:

$$\frac{N_+}{N_-} = \frac{F_{M+}}{F_{M-}} = 1 - \left(\frac{R_+}{R_D}\right)^3$$

Similarly, the ratio of a number of field-attractable particles in a doubly occupied droplet ($N_{2+}$) (wherein the occupied droplet contains two biological particles) to a number of field-attractable particles in an unoccupied droplet (N) will be, and thus the ratio of a magnetic force acting on a doubly occupied droplet ($F_{M,2+}$) to a magnetic force acting on an unoccupied droplet ($F_{M-}$) will be:

$$\frac{N_{2+}}{N_-} = \frac{F_{M,2+}}{F_{M-}} = 1 - 2\left(\frac{R_+}{R_D}\right)^3$$

That is, there may be a stronger (differential) force acting on a given unoccupied droplet than a given occupied droplet. Between occupied droplets, there may be a stronger (differential) force acting on a given singularly occupied droplet than a given doubly occupied droplet. Similarly, the more occupied a droplet is (with more biological particles), the less it will be affected by the magnetic field. As can be appreciated, the above ratios may change with deviations from the above assumptions (e.g., non-spherical biological particle, non-spherical droplet, non-uniform concentration of field-attractable particles in volume of aqueous fluid, etc.).

In another example, as described elsewhere herein, the first field application unit 236 can apply an electric field at or near the intersection 231. On account of each droplet containing field-attractable particles (e.g., conductive particles), each droplet may be attracted or repelled to or away, respectively, from the electric field. The degree of attraction (or repulsion) can be proportional to a number (and/or a concentration) of field-attractable particles in each droplet. That is, the electric force acting on a droplet, from the same electric field, can be proportional to a number (and/or a concentration) of field-attractable particles in the droplet.

The first field application unit 236 can be operatively coupled to the first controller 240. For example, the first field application unit 236 may receive instructions from the first controller 240 regarding force field strength, orientation, frequency, and/or other variables. The first controller 240 may instruct the first field application unit 236 to apply a force field sufficiently strong and in a sufficiently targeted direction towards the mixed (occupied and unoccupied) droplets such as to direct the unoccupied droplets in one channel and direct the occupied droplets to another channel. In an example, the first field application unit 236 can be placed in a location closer to a first channel (e.g., channel 224) than a second channel (e.g., channel 226) to direct the unoccupied droplets (which are subject to a stronger force from the same field) to the first channel, assuming that the field is strongest when closest to the first field application unit 236. The stronger a force from the field acts on a droplet, the more likely that the droplet will deviate from an initial flow direction (e.g., direction of flow in channel 222) into another channel having another direction. In some instances, the field application unit may be located at least in part downstream, from the intersection 231, of a channel intended to isolate unoccupied droplets (e.g., channel 224).

For example, a force field applied can be strong enough to direct the unoccupied droplets to flow to a first channel but weak enough to direct (or leave be) the occupied droplets (whether singularly, doubly, or otherwise multiply occupied) to flow to a second channel. In some instances, a magnetic field applied by the field application unit 236 can have a magnetic flux density range from at least about $10^{-5}$ Teslas (T) to about 1 T. Alternatively, the magnetic flux density can be less than or equal to about $10^{-5}$ T and/or greater than or equal to about 1 T. In some instances, an electric field applied by the field application unit 236 can have an electric field strength of at least about 1 volt per meter (V/m), 2 V/m, 3 V/m, 4 V/m, 5 V/m, 10 V/m, or more. Alternatively, the electric field strength can be less than about 10 V/m, 5 V/m, 4 V/m, 3 V/m, 2 V/m, 1 V/m, or less.

The first and third sets of droplets (e.g., 230A, C) isolated to channel 226 may be subjected to a second stage of sorting at or near the intersection 233. After the second stage of sorting at or near the intersection 233, the third subset of droplets (e.g., 230C) can be directed to flow along channel segment 246 and away from the intersection 233, and the first subset of droplets 230A can be directed to flow along channel segment 244 and away from the intersection 233. Thus, the singularly occupied droplets (first subset of droplets) may be isolated from both the unoccupied droplets and the multiply occupied droplets.

The second field application unit 237 can be configured to apply a force field to the channel structure. In some instances, the field application unit 237 can be configured to apply a force field at or near the intersection 233 such that the first subset of droplets (singularly occupied droplets) are generally directed along the channel segment 244 and away from the intersection 233, and the third subset of droplets (multiply occupied droplets) are generally directed along the channel segment 246 and away from the intersection 233, thereby separating the first and third subsets of droplets. For example, as described elsewhere herein, the second field application unit 237 may apply a magnetic field at or near the intersection 233. As described elsewhere herein, as between occupied droplets, there may be a stronger (differential) force acting on a given singularly occupied droplet than a given doubly occupied droplet. Similarly, the more occupied a droplet is (with more biological particles), the less it will be affected by the magnetic field. In another example, as described elsewhere herein, the second field application unit 237 can apply an electric field at or near the intersection 233.

The second field application unit 237 can be operatively coupled to the second controller 241. For example, the second field application unit 237 may receive instructions from the second controller 241 regarding force field strength, orientation, frequency, and/or other variables. The second controller 241 may instruct the second field application unit 237 to apply a force field sufficiently strong and in a sufficiently targeted direction towards the mixed (singularly occupied and multiply occupied) droplets such as to direct the singularly occupied droplets in one channel and direct the multiply occupied droplets to another channel. In an example, the second field application unit 237 can be placed in a location closer to a first channel (e.g., channel 244) than a second channel (e.g., channel 246) to direct the singularly occupied droplets (which are subject to a stronger force from the same field than multiply occupied droplets) to the first channel, assuming that the field is strongest when closest to the second field application unit 237. The stronger a force from the field acts on a droplet, the more likely that the droplet will deviate from an initial flow direction (e.g., direction of flow in channel 226) into another channel having another direction. In some instances, the field application unit may be located at least in part downstream, from the intersection 233, of a channel intended to isolate singularly occupied droplets (e.g., channel 244). Alternatively or in addition to, the second field application unit 236 can be operatively coupled to the first controller 240.

For example, a force field applied can be strong enough to direct the singularly occupied droplets to flow to a first channel but weak enough to direct (or leave be) the multiply occupied droplets (whether singularly, doubly, or otherwise multiply occupied) to flow to a second channel. In some instances, the force field applied by the second field application unit 237 may be stronger than the force field applied by the first field application unit 236. In some instances, a magnetic field applied by the second field application unit 237 can have a magnetic flux density range from at least about $10^{-5}$ Teslas (T) to about 1 T. Alternatively, the magnetic flux density can be less than or equal to about $10^{-5}$ T and/or greater than or equal to about 1 T. In some instances, an electric field applied by the field application unit 236 can have an electric field strength of at least about 1 volt per meter (V/m), 2 V/m, 3 V/m, 4 V/m, 5 V/m, 10 V/m, or more. Alternatively, the electric field strength can be less than about 10 V/m, 5 V/m, 4 V/m, 3 V/m, 2 V/m, 1 V/m, or less.

The systems and methods described with respect to FIGS. 2A-B may be used to isolate cell beads from particles unoccupied with biological particles, and/or separate singularly occupied cell beads from unoccupied and multiply occupied cell beads. As described elsewhere herein, a plurality of particles may comprise a first subset of particles (e.g., cell beads) occupied by biological particles (e.g., cells) and a second subset of particles unoccupied by biological particles. Both occupied and unoccupied particles may comprise field-attractable particles. Occupied particles may include singularly occupied cell beads, each containing a single biological particle, and multiply occupied cell beads, each containing two or more biological particles. For example, such particles comprising the field-attractable particles may be generated from polymerizing the plurality of droplets comprising the field-attractable particles (e.g., in FIG. 1). In a channel structure including channel segments 202, 204, and 206 meeting at a channel intersection 211, the plurality of particles may be directed to flow (e.g., as suspensions in a fluid, e.g., aqueous fluid) to the channel intersection 211 for subsequent sorting. A controller 220 can be operatively coupled to a fluid flow unit 218, to facilitate flow of fluid in the channel structure, and a field application unit 216, to apply one or more fields to the channel structure.

In operation, a plurality of discrete particles, including both cell beads and unoccupied particles, can be directed to flow along channel segment 202 into intersection 211. The plurality of particles can comprise a first subset of particles (e.g., cell beads) that are each occupied with at least a biological particle and a second subset of particles that are each unoccupied. Every particle, including cell beads and unoccupied particles, can comprise some concentration of field-attractable particles. As described with respect to the relative concentrations of field-attractable particles in occupied and unoccupied droplets, a given unoccupied particle can have a higher concentration of field-attractable particles than a given cell bead (e.g., a given occupied particle) to account for the volume occupied by a biological particle in a cell bead.

After sorting at or near the intersection 211, the first subset of particles (e.g., cell beads) can be directed to flow along channel segment 206 and away from the intersection 211, and the second subset of particles can be directed to flow along channel segment 204 and away from the intersection 211.

The fluid flow unit 218 can be configured to subject the second fluid 208 containing the plurality of particles, including both cell beads and unoccupied particles, to flow along the channel 202 towards the intersection 211. The fluid flow unit 218 can be configured to subject the second fluid 208 containing a plurality of particles, wherein a majority of the particles is unoccupied, to flow along the channel 204 away from the intersection 211. The fluid flow unit 218 can be configured to subject the second fluid 208 containing a plurality of particles, wherein a majority of the particles is cell beads (e.g., occupied particles), to flow along the channel 206 away from the intersection 211. Alternatively, the fluid flow unit 218 can be configured to subject the second fluid 208 containing a plurality of particles wherein a majority of the particles is unoccupied particles, to flow along the channel 206 away from the intersection 211, and configured to subject the second fluid 208 containing a plurality of particles, wherein a majority of the particles is cell beads, to flow along the channel 204 away from the intersection 211. The fluid flow unit 218 can be operatively coupled to the controller 220. For example, the fluid flow unit 218 may receive instructions from the controller 220 regarding fluid pressure and/or velocity.

The field application unit 216 can be configured to apply a force field to the channel structure. In some instances, the field application unit 216 can be configured to apply a force field at or near the intersection 211 such that the second subset of particles (unoccupied particles) is generally directed along the channel segment 204 and away from the intersection 211, and the first subset of particles (cell beads) is generally directed along the channel segment 206 and away from the intersection 211, thereby isolating the two subsets of particles.

For example, the field application unit 216 can apply a magnetic field at or near the intersection 211. The field application unit 216 can be a magnet and/or a circuit (e.g., current carrying device) configured to generate a magnetic field. On account of each particle containing field-attractable particles (e.g., paramagnetic particles), each particle may be attracted (e.g., due to paramagnetic particles) or repelled (e.g., due to diamagnetic particles) to or away, respectively, from the magnetic field. The degree of attraction (or repulsion) can be proportional to a number (and/or a concentration) of field-attractable particles in each particle. That is, the magnetic force acting on a particle, from the same magnetic field, can be proportional to a number (and/or a concentration) of field-attractable particles in the particle. For example, assuming that (i) the particle is spherical and has the radius $R_{CB}$, (ii) a biological particle is spherical and has the radius $R_+$, and (iii) the concentration of field-attractable particles in the particle is substantially uniform, the ratio of a number of field-attractable particles in a singularly occupied cell bead ($N_+$) (wherein the cell bead contains a single biological particle) to a number of field-attractable particles in an unoccupied particle ($N_-$) will be, and thus the ratio of a magnetic force acting on a singularly occupied cell bead ($F_{M+}$) to a magnetic force acting on an unoccupied particle ($F_{M-}$) will be:

$$\frac{N_+}{N_-} = \frac{F_{M+}}{F_{M-}} = 1 - \left(\frac{R_+}{R_{CB}}\right)^3$$

That is, there may be a stronger (differential) force acting on a given unoccupied particle than a given cell bead. As can be appreciated, the above ratio may change with deviations from the above assumptions (e.g., non-spherical biological particle, non-spherical particle, non-uniform concentration of field-attractable particles in volume of particle, etc.).

In another example, the field application unit 216 can apply an electric field at or near the intersection 211. On account of each particle containing field-attractable particles (e.g., conductive particles), each particle may be attracted or repelled to or away, respectively, from the electric field. The degree of attraction (or repulsion) can be proportional to a number (and/or a concentration) of field-attractable particles in each particle. That is, the electric force acting on a particle, from the same electric field, can be proportional to a number (and/or a concentration) of field-attractable particles in the particle. As previously described above, assuming that (i) the particle is spherical and has the radius $R_{O3}$, (ii) a biological particle is spherical and has the radius $R_+$, and (iii) the concentration of field-attractable particles in the volume of a particle is substantially uniform, the ratio of a number of field-attractable particles in a singularly occupied cell bead ($N_+$) (wherein the cell bead contains a single biological particle) to a number of field-attractable particles in an unoccupied particle ($N_-$) will be, and thus the ratio of an electric force acting on a singularly occupied cell bead ($F_{E+}$) to an electric force acting on an unoccupied particle ($F_E$) will be:

$$\frac{N_+}{N_-} = \frac{F_{E+}}{F_{E-}} = 1 - \left(\frac{R_+}{R_D}\right)^3$$

As can be appreciated, the above ratio may change with deviations from the above assumptions (e.g., non-spherical biological particle, non-spherical particle, non-uniform concentration of field-attractable particles in volume of a particle, etc.). In some instances, the fluid flow unit 218 can apply both an electric field and a magnetic field.

The field application unit 216 can be operatively coupled to the controller 220. For example, the field application unit 216 may receive instructions from the controller 220 regarding force field strength, orientation, frequency, and/or other variables. The controller 220 may instruct the field application unit 216 to apply a force field sufficiently strong and in a sufficiently targeted direction towards the mixed (occupied and unoccupied) particles such as to direct the unoccupied particles in one channel and direct the occupied particles to another channel. In an example, the field application unit 216 can be placed in a location closer to a first channel (e.g., channel 204) than a second channel (e.g., channel 206) to direct the unoccupied particles (which are subject to a stronger force from the same field) to the first channel, assuming that the field is strongest when closest to the field application unit 216. The stronger a force from the field acts on a particle, the more likely that the particle will deviate from an initial flow direction (e.g., direction of flow in channel 202) into another channel having another direction. In some instances, the field application unit may be located at least in part downstream, from the intersection 211, of a channel intended to isolate unoccupied particles (e.g., channel 204).

For example, a force field applied can be strong enough to direct the unoccupied particles to flow to a first channel but weak enough to direct (or leave be) the occupied particles to flow to a second channel. In some instances, a magnetic field applied by the field application unit 216 can have a magnetic flux density range from at least about $10^{-5}$ Teslas (T) to about 1 T. Alternatively, the magnetic flux density can be less than or equal to about $10^{-5}$ T and/or greater than or equal to about 1 T. In some instances, an electric field applied by the field application unit 216 can have an electric field strength of at least about 1 volt per meter (V/m), 2 V/m, 3 V/m, 4 V/m, 5 V/m, 10 V/m, or more. Alternatively, the electric field strength can be less than about 10 V/m, 5 V/m, 4 V/m, 3 V/m, 2 V/m, 1 V/m, or less.

Similarly, singularly occupied cell beads may be sorted from unoccupied particles and multiply occupied cell beads by using the systems and methods described with respect to FIG. 2B but introducing a plurality of particles (comprising a first subset of singularly occupied cell beads, a second subset of unoccupied particles, and a third subset of multiply occupied cell beads), each particle comprising field attractable particles, in place of the plurality of droplets comprising the field attractable particles.

While FIG. 2A and FIG. 2B each depicts a channel structure wherein a second channel (e.g., channel 204) branches off a first channel (e.g., channel 202) at a sorting intersection (e.g., intersection 211) such that a third channel (channel 204) continues in the same direction as the first channel, it can be appreciated that the systems and methods disclosed herein may be application to different channel structures. For example, the third channel can be at a different angle (e.g., not) 180° than the first channel. In some examples, the channel structure may have more than two channels branching off the first channel, wherein the field application unit 216 is configured to separate the droplets into unoccupied droplets, droplets containing only one biological particle, droplets containing more than one biological particles, droplets containing only barcode carrying beads, droplets containing both a biological particle and barcode carrying beads, or other variations. In some examples, the channel structure may have more than two channels branching off the first channel, wherein the field application unit 216 is configured to separate the particles into unoccupied particles, particles containing only one biological particle, particles containing more than one biological particles, particles containing only barcode carrying beads, particles containing both a biological particle and barcode carrying beads, or other variations. For example, the more volume of a droplet or a particle is occupied by one or more biological particles and/or one or more barcode carrying beads contained therein, the weaker can be the force acting on the droplet or the particle by the field applied by the field application unit 216, and thus the less the deviation in direction of flow relative to the direction of flow in the first channel. That is, upon application of a force field, the unoccupied droplets or particles may be capable of deviating the most (e.g., to a channel closest to the field application unit), a droplet or particle containing a single biological particle (e.g., singularly occupied cell bead) may be capable of deviating but not as much as the unoccupied droplets or particles (e.g., to a channel second closest to the field application unit), and a droplet or particle containing both a biological particle and a barcode carrying bead may be capable of deviating the least of the three types of droplets or particles (e.g., to a channel farthest from the field application unit).

While FIGS. 2A-2B depict narrow channels allowing for the flow of droplets and/or particles only in single file, the systems and methods disclosed herein may be applicable to channels having a broader width (e.g., diameter) that allows for the flow of droplets and/or particles in more than single file.

While FIG. 2A depicts one controller 220 operatively coupled to both the fluid flow unit 218 and the field application unit 216, a separate controller can be coupled to the fluid flow unit 218 and a separate controller can be coupled to the field application unit 216. The two separate controllers may or may not be in communication with each other. In some instances, there may be a plurality of controllers (e.g., two controllers to a fluid flow unit 218), wherein each controller may or may not be in communication with each other. The controller 220 may send instructions to the fluid flow unit 218 and/or the field application unit 216 via wired connection and/or wireless connection (e.g., Wi-Fi, Bluetooth, NFC, etc.).

Figure 3:
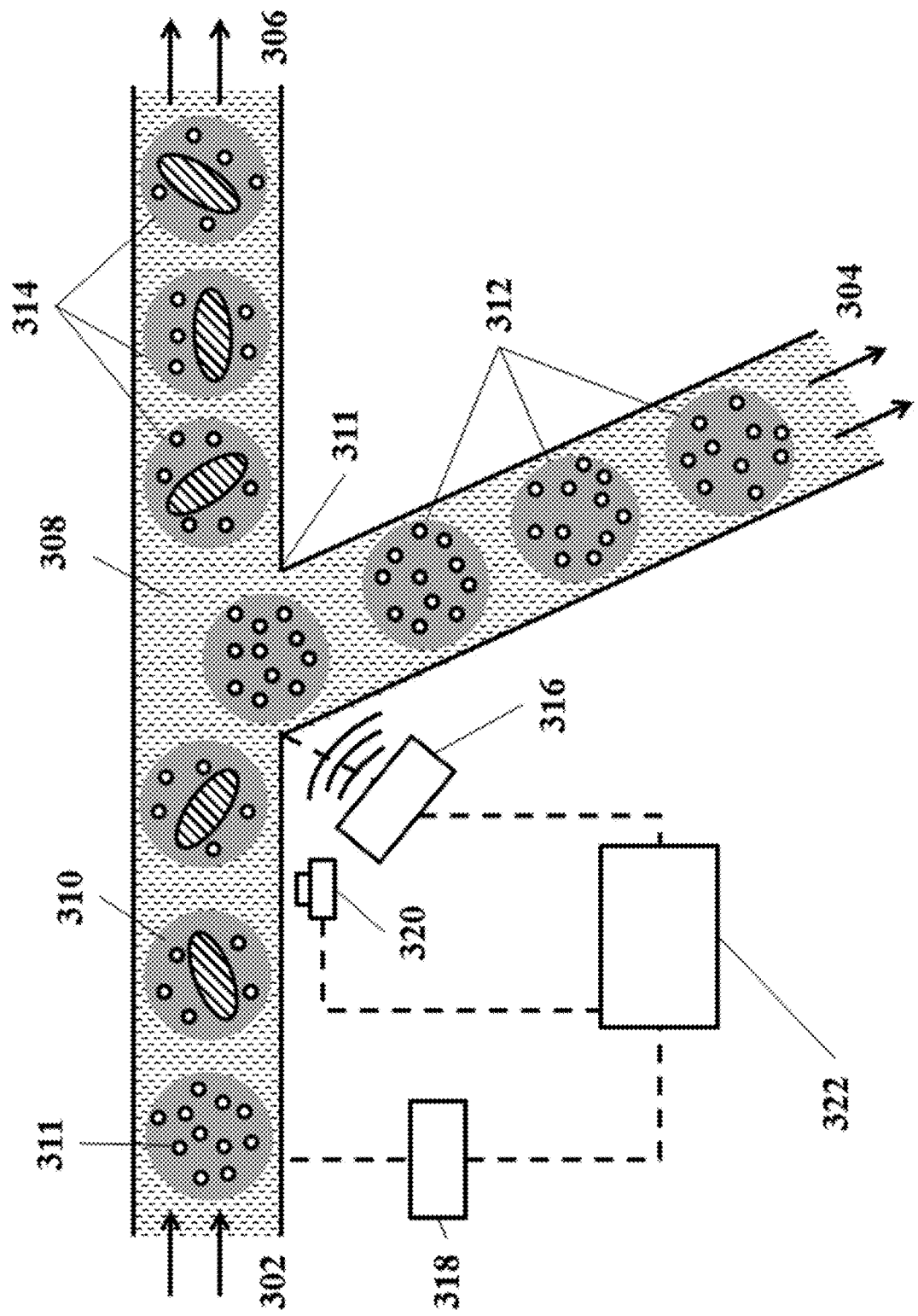
FIG. 3 shows another example of a microfluidic channel structure for separating occupied droplets from unoccupied droplets.

FIG. 3 shows another example of a microfluidic channel structure for separating occupied droplets from unoccupied droplets. As described elsewhere herein, when droplets are generated, there may be a first subset population of occupied droplets containing one or more biological particles and a second subset population of unoccupied droplets not containing any biological particles. In some cases, the droplets may additionally contain one or more barcode carrying beads. For example, a droplet may have only a biological particle, a droplet may have only a barcode carrying bead, a droplet may have both a biological particle and a barcode carrying bead, or a droplet may have neither biological particles nor barcode carrying beads. In some cases, the majority of occupied partitions can include no more than one biological particle per occupied partition and, in some cases, some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

As shown in FIG. 3, the channel structure can include channel segments 302, 304, and 306 meeting at a channel intersection 311. In some instances, the outflow channel 108 of the emulsion carrying the generated droplets in FIG. 1 can be upstream of the channel segment 302, such that the generated droplets are directed to flow to the channel intersection 211 for subsequent sorting. A controller 322 can be operatively coupled to a fluid flow unit 318, to facilitate flow of fluid in the channel structure, a sensor 320, to detect at least a characteristic of a droplet or a plurality of droplets, and a pressure application unit 316, to apply a pressure pulse to the channel structure.

In operation, a plurality of discrete droplets, each comprising a first aqueous fluid 310 can flow as emulsions in a second fluid 308, wherein the second fluid 308 is immiscible to the first aqueous fluid 310. The droplets being transported along channel segment 302 into intersection 311 can comprise a first subset of droplets 314 that are each occupied with at least a biological particle and/or a barcode carrying bead and a second subset of droplets 312 that are each unoccupied. Every droplet, including occupied and unoccupied droplets, may or may not comprise some concentration of field-attractable particles. Although FIG. 3 depicts each droplet as comprising field-attractable particles 315, this is not required.

After sorting at or near the intersection 311, the first subset of droplets 314 can be directed to flow along channel segment 306 and away from the intersection 311, and the second subset of droplets 312 can be directed to flow along channel segment 304 and away from the intersection 311.

The fluid flow unit 318 can be configured to subject the second fluid 308 containing a plurality of droplets, including both occupied droplets and unoccupied droplets, to flow along the channel 302 towards the intersection 311. The fluid flow unit 318 can be configured to subject the second fluid 308 containing a plurality of droplets, wherein a majority of the droplets is unoccupied droplets, to flow along the channel 304 away from the intersection 311. The fluid flow unit 318 can be configured to subject the second fluid 308 containing a plurality of droplets, wherein a majority of the droplets is occupied droplets, to flow along the channel 306 away from the intersection 311. Alternatively, the fluid flow unit 318 can be configured to subject the second fluid 308 containing a plurality of droplets, wherein a majority of the droplets is unoccupied droplets, to flow along the channel 306 away from the intersection 311, and configured to subject the second fluid 308 containing a plurality of droplets, wherein a majority of the droplets is occupied droplets, to flow along the channel 304 away from the intersection 311. The fluid flow unit 318 can be operatively coupled to the controller 322. For example, the fluid flow unit 318 may receive instructions from the controller 322 regarding fluid pressure and/or velocity.

In some instances, the fluid flow unit 318 may comprise a compressor to provide positive pressure at an upstream location to direct the fluid from the upstream location to flow to a downstream location. In some instances, the fluid flow unit 318 may comprise a pump to provide negative pressure at a downstream location to direct the fluid from an upstream location to flow to the downstream location. In some instances, the fluid flow unit 318 may comprise both a compressor and a pump, each at different locations. In some instances, the fluid flow unit 318 may comprise different devices at different locations. The fluid flow unit 318 may comprise an actuator. While FIG. 3 depicts one fluid flow unit 318, it may be appreciated that there may be a plurality of fluid flow units 318, each in communication with the controller 322 and/or with each other. For example, there can be a separate fluid flow unit to direct the fluid in channel 302 towards the intersection 311, a separate fluid flow unit to direct the fluid in channel 304 away from the intersection 311, and a separate fluid flow unit to direct the fluid in channel 306 away from the intersection 311.

The sensor 320 can be configured to sense at least a characteristic of a droplet or a plurality of droplets in the first channel segment 302. In some instances, the sensor 320 may detect the characteristic of a droplet as the droplet passes the sensor 320. The sensor 320 may be located upstream of the intersection 311. One or more characteristics detected by the sensor 320 of a droplet can be indicative of the type of droplet, such as whether the droplet is occupied or unoccupied, or whether the droplet contains a biological particle and/or a barcode carrying bead. In some instances, the sensor 320 can be an impedance sensor configured to measure bulk impedance when droplets pass by the sensor 320. In some instances, a higher impedance can be measured for occupied droplets than for unoccupied droplets (e.g., due to mass and/or weight distribution of occupied droplet, etc.). In some instances, the sensor 320 can be an optical sensor configured to measure optical properties of a droplet, such as to distinguish whether the droplet is occupied or unoccupied. The optical sensor and/or a supporting device may be configured to emit a detection signal configured to probe one or more droplets, including for example an electromagnetic signal (e.g., in any wavelength) and/or an acoustic signal. In some instances, the optical sensor and/or a supporting device may comprise an illumination source configured to illuminate the droplet or droplets with one or more types of electromagnetic radiation. In some instances, the electromagnetic radiation can include illumination in one or more of the visible spectrum, infrared spectrum, the ultraviolet spectrum, and ionizing radiation spectrum. In some instances, the ionizing radiation can include x-rays. Alternatively the sensor 320 may be one or more devices that are configured to provide one or more of optical sensing, thermal sensing, laser imaging, infrared imaging, capacitance sensing, mass sensing, vibration sensing across at least a portion of the electromagnetic spectrum, and magnetic induction sensing. The sensor 320 can be operatively coupled to the controller 322. For example, the sensor 320 may transmit sensor data (e.g., on one or more characteristics of a droplet or a plurality of droplets) to the controller 322. The controller 322 may then use such data to determine whether the droplet is occupied or unoccupied.

While FIG. 3 depicts one sensor 320, it may be appreciated that there may be a plurality of sensors, each in communication with the controller 322 and/or with each other. For example, there can be a plurality of sensors upstream of the intersection 311 at different locations, for example, detecting one or more characteristics of a droplet or a plurality of droplets at different angles.

The pressure application unit 316 can be configured to apply a pressure pulse to the channel structure. In some instances, the pressure application unit 316 can be configured to apply a pressure pulse at or near the intersection 311 such that, via hydrodynamic forces, the second subset of droplets (unoccupied droplets) are generally directed along the channel segment 304 and away from the intersection 311, and the first subset of droplets (occupied droplets) are generally directed along the channel segment 306 and away from the intersection 311, thereby isolating the two subsets of droplets.

In some instances, the pressure application unit 316 may comprise a compressor to provide positive pressure pulses at an upstream location to direct the fluid from the upstream location to flow to a downstream location. In some instances, the pressure application unit 316 may comprise a pump to provide negative pressure pulses at a downstream location to direct the fluid from an upstream location to flow to the downstream location. In some instances, the pressure application unit 316 may comprise both a compressor and a pump, each at different locations. In some instances, the pressure application unit 316 may comprise different devices at different locations. The pressure application unit 316 may comprise an actuator. While FIG. 3 depicts one pressure application unit 316, it may be appreciated that there may be a plurality of pressure application units, each in communication with the controller 322 and/or with each other. In some instances, the pressure application unit 316 and a fluid flow unit 318 may be the same device or same devices. In some instances, the pressure application unit 316 may be, entirely or at least in part, external to the microfluidic structure (e.g., microfluidic channels), as illustrated in FIG. 3. In some instances, the pressure application unit 316 may be, entirely or at least in part, internal to and/or integral to the microfluidic structure. For example, a pressure pulse may be generated by deflection of membranes. In some instances, a pressure pulse may be generated from generation of air bubbles, wherein expansion of the bubble may displace fluid parcels.

Occupied droplets and unoccupied droplets may respond differently to a pressure pulse, for example due to varying predetermined particle and fluid characteristics. In some instances, singularly occupied droplets and multiply occupied droplets may respond differently to a pressure pulse. The predetermined particle and fluid characteristics can include size of a droplet, mass of a droplet, viscosity of droplet suspension in the emulsion, deformability, and other characteristics. That is, a given singularly occupied droplet, a multiply occupied droplet, and an unoccupied droplet may respond differently when subject to hydrodynamic forces triggered by the pressure pulses. In some instances, the controller 322 may, based on a determination made from data received from the sensor 320 (e.g., determination on whether droplet is occupied or unoccupied), instruct the pressure application unit 316 to apply different pressure pulses, for example, by varying frequency of the pulses and/or changing pressure differential. For example, the pressure application unit 316 may apply a first type of pressure pulse when an occupied droplet is approaching the intersection 311 and a second type of pressure pulse when an unoccupied droplet is approaching the intersection 311. Alternatively, the same pressure pulse can be applied for any type of droplet approaching the intersection 311, and the droplet may react (or respond) differently (e.g., deviating from a fluid flow direction at different angles) depending on whether the droplet is occupied or unoccupied.

The pressure application unit 316 can be operatively coupled to the controller 320. For example, the pressure application unit 316 may receive instructions from the controller 322 regarding pressure pulse strength, frequency, and/or other variables.

The systems and methods described with respect to FIG. 3 may be used to separate occupied particles from unoccupied particles. As described elsewhere herein, a plurality of particles may comprise a first subset of particles (e.g., cell beads) occupied by biological particles (e.g., cells) and a second subset of particles unoccupied by biological particles. In a channel structure including channel segments 302, 304, and 306 meeting at a channel intersection 311, the plurality of particles may be directed to flow (e.g., as suspensions in a fluid, e.g., aqueous fluid) to the channel intersection 311 for subsequent sorting. A controller 322 can be operatively coupled to a fluid flow unit 318, to facilitate flow of fluid in the channel structure, a sensor 320, to detect at least a characteristic of a particle or a plurality of particles, and a pressure application unit 316, to apply a pressure pulse to the channel structure.

After sorting at or near the intersection 311, the first subset of particles (e.g., cell beads) can be directed to flow along channel segment 306 and away from the intersection 311, and the second subset of particles can be directed to flow along channel segment 304 and away from the intersection 311.

The fluid flow unit 318 can be configured to subject the second fluid 308 containing a plurality of particles, including both cell beads and unoccupied particles, to flow along the channel 302 towards the intersection 311. The fluid flow unit 318 can be configured to subject the second fluid 308 containing a plurality of particles, wherein a majority of the particles is unoccupied particles, to flow along the channel 304 away from the intersection 311. The fluid flow unit 318 can be configured to subject the second fluid 308 containing a plurality of particles, wherein a majority of the particles is occupied particles, to flow along the channel 306 away from the intersection 311. Alternatively, the fluid flow unit 318 can be configured to subject the second fluid 308 containing a plurality of particles, wherein a majority of the particles is unoccupied particles, to flow along the channel 306 away from the intersection 311, and configured to subject the second fluid 308 containing a plurality of particles, wherein a majority of the particles is occupied particles, to flow along the channel 304 away from the intersection 311. The fluid flow unit 318 can be operatively coupled to the controller 322. For example, the fluid flow unit 318 may receive instructions from the controller 322 regarding fluid pressure and/or velocity.

The sensor 320 can be configured to sense at least a characteristic of a particle or a plurality of particles in the first channel segment 302. In some instances, the sensor 320 may detect the characteristic of a particle as the particle passes the sensor 320. The sensor 320 may be located upstream of the intersection 311. One or more characteristics detected by the sensor 320 of a particle can be indicative of the type of particle, such as whether the particle is occupied or unoccupied, or whether the particle contains a biological particle and/or a barcode carrying bead. In some instances, the sensor 320 can be an impedance sensor configured to measure bulk impedance when particles pass by the sensor 320. In some instances, a higher impedance can be measured for occupied particles than for unoccupied particles (e.g., due to mass and/or weight distribution of occupied particle, etc.). In some instances, the sensor 320 can be an optical sensor configured to measure optical properties of a particle, such as to distinguish whether the particle is occupied or unoccupied. The optical sensor and/or a supporting device may be configured to emit a detection signal configured to probe one or more particles, including for example an electromagnetic signal (e.g., in any wavelength) and/or an acoustic signal. In some instances, the optical sensor and/or a supporting device may comprise an illumination source configured to illuminate the particle or particles with one or more types of electromagnetic radiation. In some instances, the electromagnetic radiation can include illumination in one or more of the visible spectrum, infrared spectrum, the ultraviolet spectrum, and ionizing radiation spectrum. In some instances, the ionizing radiation can include x-rays. Alternatively the sensor 320 may be one or more devices that are configured to provide one or more of optical sensing, thermal sensing, laser imaging, infrared imaging, capacitance sensing, mass sensing, vibration sensing across at least a portion of the electromagnetic spectrum, and magnetic induction sensing. The sensor 320 can be operatively coupled to the controller 322. For example, the sensor 320 may transmit sensor data (e.g., on one or more characteristics of a particle or a plurality of particles) to the controller 322. The controller 322 may then use such data to determine whether the particle is occupied or unoccupied.

While FIG. 3 depicts one sensor 320, it may be appreciated that there may be a plurality of sensors, each in communication with the controller 322 and/or with each other. For example, there can be a plurality of sensors upstream of the intersection 311 at different locations, for example, detecting one or more characteristics of a particle or a plurality of particles at different angles.

The pressure application unit 316 can be configured to apply a pressure pulse to the channel structure. In some instances, the pressure application unit 316 can be configured to apply a pressure pulse at or near the intersection 311 such that, via hydrodynamic forces, the second subset of particles (unoccupied particles) are generally directed along the channel segment 304 and away from the intersection 311, and the first subset of particles (cell beads) are generally directed along the channel segment 306 and away from the intersection 311, thereby isolating the two subsets of particles.

Occupied particles and unoccupied particles may respond differently to a pressure pulse, for example due to varying predetermined particle and fluid characteristics. The predetermined particle and fluid characteristics can include size of a particle, mass of a particle, viscosity of particle suspension in the fluid, deformability, and other characteristics. That is, a given singularly occupied cell bead, multiply occupied cell bead, and an unoccupied particle may respond differently when subject to hydrodynamic forces triggered by the pressure pulses. In some instances, the controller 322 may, based on a determination made from data received from the sensor 320 (e.g., determination on whether particle is occupied or unoccupied), instruct the pressure application unit 316 to apply different pressure pulses, for example, by varying frequency of the pulses and/or changing pressure differential. For example, the pressure application unit 316 may apply a first type of pressure pulse when an occupied particle is approaching the intersection 311 and a second type of pressure pulse when an unoccupied particle is approaching the intersection 311. Alternatively, the same pressure pulse can be applied for any type of particle approaching the intersection 311, and the particle may react (or respond) differently (e.g., deviating from a fluid flow direction at different angles) depending on whether the particle is occupied or unoccupied. In some instances, different pressure pulses may be applied as between occupied and unoccupied droplets, occupied and unoccupied particles, singularly occupied and multiply occupied droplets, and/or singularly occupied and multiply occupied cell beads.

The pressure application unit 316 can be operatively coupled to the controller 320. For example, the pressure application unit 316 may receive instructions from the controller 322 regarding pressure pulse strength, frequency, and/or other variables.

While FIG. 3 depicts a channel structure wherein a second channel (channel 304) branches off a first channel (channel 302) such that a third channel (channel 304) continues in the same direction as the first channel, it can be appreciated that the systems and methods disclosed herein may be application to different channel structures. For example, the third channel can be at a different angle (e.g., not 180°) than the first channel. In some examples, the channel structure may have more than two channels branching off the first channel, wherein the pressure application unit 316 is configured to separate the droplets into unoccupied droplets, droplets containing only one biological particle, droplets containing more than one biological particles, droplets containing only barcode carrying beads, droplets containing both a biological particle and barcode carrying beads, or other variations. The pressure application unit 316 can be configured to separate particles into unoccupied particles, particles containing only one biological particle, particles containing more than one biological particle, particles containing only barcode carrying beads, particles containing both a biological particle and barcode carrying beads, or other variations. For example, upon application of a pressure pulse, the unoccupied droplets or particles may be capable of deviating the most (e.g., to a first channel), a droplet or particle containing a single biological particle may be capable of deviating but not as much as the unoccupied droplets or particles (e.g., to a second channel), and a droplet or particle containing both a biological particle and a barcode carrying bead may be capable of deviating the least of the three types of droplets or particles (e.g., to a third channel).

While FIG. 3 depicts narrow channels allowing for the flow of droplets or particles only in single file, the systems and methods disclosed herein may be applicable to channels having a broader width (e.g., diameter) that allows for the flow of droplets or particles in more than single file.

While FIG. 3 depicts one controller 322 operatively coupled to all of the fluid flow unit 318, the sensor 320, and the pressure application unit 316, a separate controller can be coupled to the fluid flow unit 318, a separate controller can be coupled to the sensor 320, and a separate controller can be coupled to the pressure application unit 216. The three separate controllers may or may not be in communication with each other. In some instances, there may be a plurality of controllers (e.g., two controllers to a fluid flow unit 318), wherein each controller may or may not be in communication with each other. The controller 322 may send instructions to the fluid flow unit 318, sensor 320, and/or the pressure application unit 316 via wired connection and/or wireless connection (e.g., Wi-Fi, Bluetooth, NFC, etc.). The controller 322 may receive data from the fluid flow unit 318, sensor 320, and/or the pressure application unit 316 via wired connection and/or wireless connection (e.g., Wi-Fi, Bluetooth, NFC, etc.). In some instances, the components can be directly or indirectly be in communication with each other, with or without going through the controller 322. For example, the sensor 320 may be directly coupled to the pressure application unit 316.

The separation systems and methods disclosed herein may achieve super Poisson loading. For example, the droplets can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of droplets that is isolated are occupied droplets (e.g., containing at least one biological particle). Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of the first subset of droplets can be occupied droplets. In some instances, at least about 97%, 98%, 99%, or a higher percentage of a second subset of droplets that is isolated can be unoccupied droplets (e.g., not containing any biological particle and not containing any barcode carrying beads). Alternatively, less than about 97% of the second subset of droplets can be unoccupied droplets. For example, the particles can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of particles that is isolated are cell beads (e.g., containing at least one biological particle). Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of the first subset of particles can be occupied particles (e.g., cell beads). In some instances, at least about 97%, 98%, 99%, or a higher percentage of a second subset of particles that is isolated can be unoccupied particles (e.g., not containing any biological particle and not containing any barcode carrying beads). Alternatively, less than about 97% of the second subset of particles can be unoccupied particles.

The channel networks, e.g., as described herein above or further below, can be fluidly coupled to appropriate fluidic components. For example, the inlet channel segments (e.g., channel segment 202 in FIG. 2A, channel segments 102, 104, 106 in FIG. 1) are fluidly coupled to appropriate sources of the materials they are to deliver to a channel junction (e.g., intersection 211 in FIG. 2A, junction 110 in FIG. 1). For example, channel segment 202 will be fluidly coupled to a source of an aqueous suspension of biological particles (e.g., biological particles 114 in FIG. 1) to be analyzed and field-attractable particles (e.g., field-attractable particles 115 in FIG. 1). Channel segments 104 and 106 may then be fluidly connected to one or more sources of the non-aqueous (or other immiscible) fluid. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment 206 may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

In some instances, a plurality of droplets not containing any field-attractable particles, may also be sorted using dielectrophoresis. For example, occupied droplets and unoccupied droplets can have different dielectric properties. When an electric field is applied, such as via methods described elsewhere herein (e.g., with reference to FIG. 2A), to a plurality of droplets comprising both occupied droplets and unoccupied droplets, such as at an intersection wherein a first channel branches off into a second channel and a third channel, the occupied droplets may be directed to flow through the first channel and unoccupied droplets may be directed to flow through the second channel, due at least in part to the varying interactions with (or influence of) the electric field of the occupied droplets and the unoccupied droplets having different dielectric properties. Such systems and methods for dielectrophoresis may also be used to sort a plurality of particles into a first subset of occupied particles (e.g., cell beads) and a second subset of unoccupied particles.

The biological particle can be subjected to conditions sufficient to polymerize or gel the precursors. The conditions sufficient to polymerize or gel the precursors may comprise exposure to heating, cooling, electromagnetic radiation, or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles. In some cases, the cell bead may further comprise one or more field-attractable particles (e.g., paramagnetic particles, conductive particles, etc.), such as via the systems and methods described elsewhere herein, for facilitating subsequent sorting and/or solvent exchange. The field-attractable particles may be trapped in the gel matrix. In some instances, the field-attractable particles may be trapped evenly throughout the gel matrix. In some instances, the field-attractable particles may be trapped throughout the gel matrix such as to subject the whole of the cell bead evenly to a force (e.g., magnetic, electric) field.

In another aspect, provided herein are systems and methods for selective polymerization of partitions (or cells therein). In some instances, the partitions may be selectively polymerized based on occupancy. In some instances, the partitions may be selectively polymerized based on size.

Figure 4:
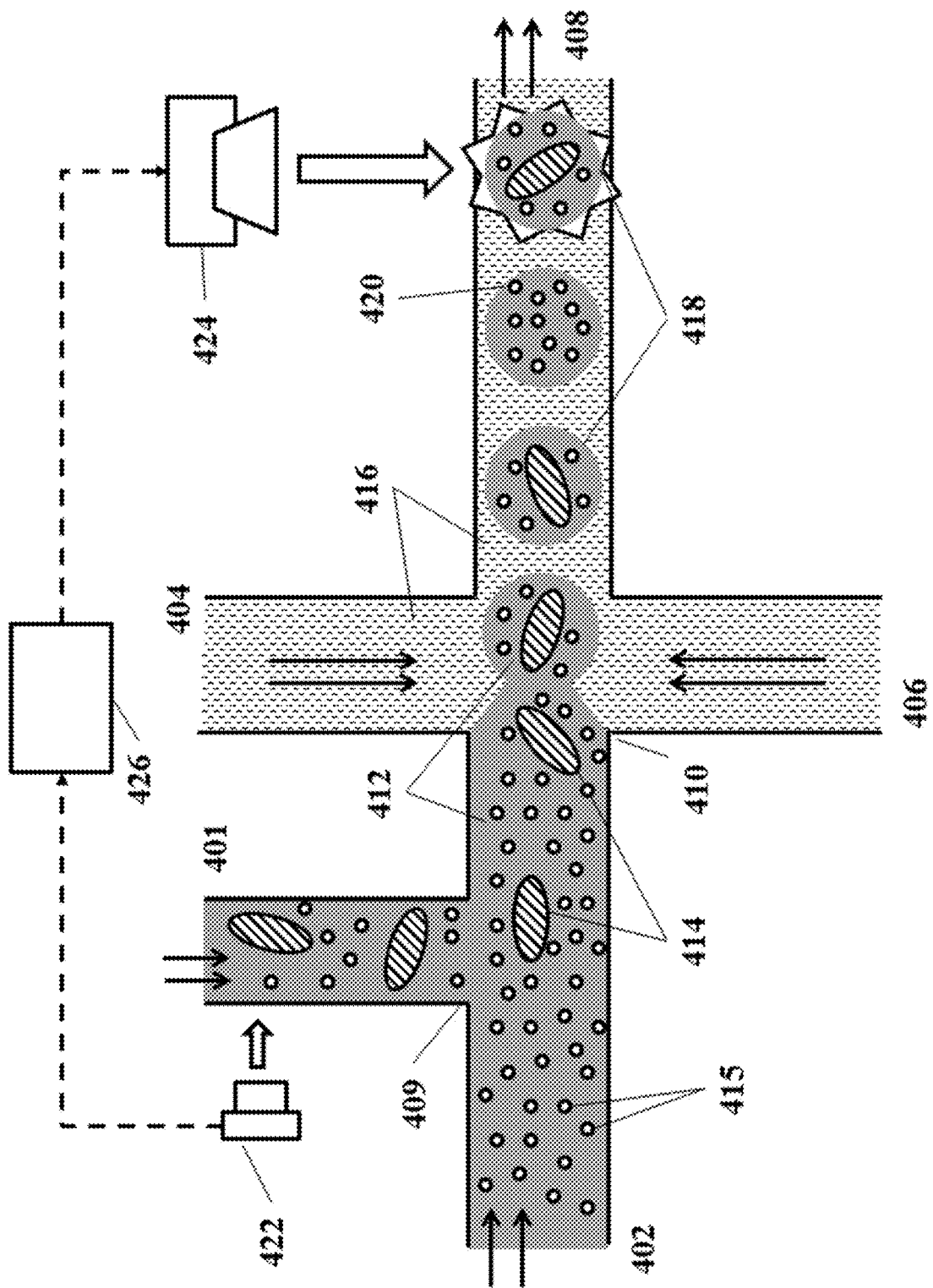
FIG. 4 shows an example of a microfluidic channel structure for selective polymerization of partitions based on occupancy.

FIG. 4 shows an example of a microfluidic channel structure for selective polymerization of partitions based on occupancy. As described elsewhere herein, in some cases, the majority of occupied partitions can include no more than one biological particle per occupied partition and, in some cases, some of the generated partitions can be unoccupied (of any biological particle). In some cases, though, some of the occupied partitions may include more than one biological particle. In some cases, the partitioning process may be controlled such that fewer than 25% of the occupied partitions contain more than one biological particle, and in many cases, fewer than 20% of the occupied partitions have more than one biological particle, while in some cases, fewer than 10% or even fewer than 5% of the occupied partitions include more than one biological particle per partition.

The emulsion mechanism of FIG. 4 can largely parallel that of FIG. 1. As shown in FIG. 4, the channel structure can include channel segments 401, 402, 404, 406 and 408. Channel segments 401 and 402 can communicate at a channel junction 409. Channel segments 402, 404, 406, and 408 can communicate at a channel junction 410. In operation, a first aqueous fluid 412 can be delivered to junction 409 from each of channel segments 402 and 401. Cells 414 can be introduced into the junction 409 via the channel segment 401 as suspensions in the first aqueous fluid 412 flowing along the channel segment 401. The first aqueous fluid 412 may or may not contain suspended field-attractable particles 115. As described elsewhere herein, occupied droplets and unoccupied droplets may be sorted via the field-attractable particles 115. A second fluid 416 that is immiscible with the aqueous fluid 412 is delivered to the junction 410 from each of channel segments 404 and 406 to create discrete droplets 418, 420 of the first aqueous fluid 412 flowing into channel segment 408, and flowing away from junction 410. A discrete droplet generated may or may not include biological particles 414.

The second fluid 416 can comprise an oil, such as a fluorinated oil, and a surfactant, such as a fluorosurfactant for stabilizing the resulting droplets, e.g., inhibiting subsequent coalescence of the resulting droplets. Examples of particularly useful partitioning fluids and fluorosurfactants are described for example, in U.S. Patent Application Publication No. 2010/0105112, which is entirely incorporated herein by reference for all purposes.

The generated droplets may comprise two subsets of droplets: (1) occupied droplets 418, containing one or more biological particles 414, and (2) unoccupied droplets 420, not containing any biological particles 414.

A photo polymerization light source 424, such as a laser, can be located downstream of the junction 410 to selectively polymerize occupied droplets (e.g., polymerize the biological particles therein). In some instances, the light source 424 can be a lamp or light emitting diode (LED). The light source can be an ultraviolet (UV) radiation source. The light source 424 can generate optical pulses or an electromagnetic beam at a targeted direction. For example, the light source 424 can be configured to only emit electromagnetic waves when an occupied droplet is passing by. The light source 424 can be operatively coupled to a controller 426. The light source 424 can receive instructions from the controller 426 on whether or not a droplet passing by the light source 424, or a droplet expected to pass by the light source at a certain time, is occupied. While FIG. 4 depicts one light source 424, it may be appreciated that there may be a plurality of light sources, each in communication with the controller 426 and/or with each other. For example, a plurality of light sources may each be located at different locations, including different upstream/downstream locations in the fluidic channels. Alternatively, a different polymerization application unit can be used to subject the droplets to a stimulus, such as to trigger polymerization via heating, cooling, electromagnetic radiation, and/or light. The stimulus can be a chemical stimulus. In some instances, a plurality of the same or different types of polymerization application units can be used at different locations.

A sensor 422 can be configured to sense the presence of a biological particle (or cell) 414 in the fluid flow. For example, the sensor 422 can be configured to sense the presence of a biological particle (or cell) 414 in the channel segment 401 upstream of the junction 409. The sensor 422 may be located upstream of the junction 409. In some instances, the sensor 422 can be an impedance sensor configured to measure bulk impedance when cells 414 pass by the sensor 422. In some instances, a higher impedance can be measured when a cell 414 passes by than when only the first aqueous fluid 412 passes by. In some instances, the sensor 422 can be an optical sensor configured to measure optical properties of a cell 414. The optical sensor and/or a supporting device may be configured to emit a detection signal configured to probe one or more droplets, including for example an electromagnetic signal (e.g., in any wavelength) and/or an acoustic signal. In some instances, the optical sensor and/or a supporting device may comprise an illumination source configured to illuminate the cell with one or more types of electromagnetic radiation. In some instances, the electromagnetic radiation can include illumination in one or more of the visible spectrum, infrared spectrum, the ultraviolet spectrum, and ionizing radiation spectrum. In some instances, the ionizing radiation can include x-rays. The illumination can be transillumination or epi-illumination. Alternatively, the sensor 422 may be one or more devices that are configured to provide one or more of optical sensing, thermal sensing, laser imaging, infrared imaging, capacitance sensing, mass sensing, vibration sensing across at least a portion of the electromagnetic spectrum, and magnetic induction sensing. The sensor 422 may collect sensor data on one or more properties (e.g., optical properties, impendence properties, etc.) or characteristics of a cell 414.

The sensor 422 can be operatively coupled to the controller 426. For example, the sensor 426 may transmit sensor data (e.g., on presence of one or more cells 414) to the controller 426. The controller 426 may determine when a cell has passed by the sensor location from the sensor data. The controller 426 may then use such sensor data, the location of the sensor and/or the location in the fluidic channel at which the presence of a cell 414 was detected, the time the sensor detected a presence of the cell 414 in the flow, fluid flow rate of the first aqueous fluid 412 in the channel segment 402, fluid flow rate of emulsion in the channel segment 408, location of the light source 424, time it takes for the sensor 426 to detect and/or transmit data to the controller 426, and/or time it takes for the controller 426 to send instructions to the light source 424, to send instructions to the light source 424 on whether or not to emit an electromagnetic wave to polymerize a droplet. For example, assuming that the fluid flow rates in the channel segments 402 and/or 408 are substantially constant, the controller 426 may determine whether a droplet created (e.g., at junction 410) at a certain time contains a cell or does not contain a cell. Based on the fluid flow rates in the channel segments 402 and/or 408, the controller 426 may determine whether a droplet passing by the light source 424 at a certain time (e.g., time it takes for droplet to travel from junction 410 to the location of the light source 424 site is the same every time) is occupied or unoccupied.

While FIG. 4 depicts one sensor 422, it may be appreciated that there may be a plurality of sensors, each in communication with the controller 426 and/or with each other. For example, there can be a plurality of sensors upstream of the junction 409 and/or upstream of the junction 410 at different locations, for example, detecting the presence of a cell 414.

While FIG. 4 depicts one controller 426 operatively coupled to both the sensor 422 and the light source 424, a separate controller can be coupled to the sensor 422 and a separate controller can be coupled to the light source 424. The separate controllers may or may not be in communication with each other. In some instances, there may be a plurality of controllers (e.g., two controllers to sensor 422), wherein each controller may or may not be in communication with each other. The controller 426 may send instructions to sensor 422 and/or the light source 424 via wired connection and/or wireless connection (e.g., Wi-Fi, Bluetooth, NFC, etc.). The controller 422 may receive data from the sensor 422 and/or the light source 424 via wired connection and/or wireless connection (e.g., Wi-Fi, Bluetooth, NFC, etc.). In some instances, the components can be directly or indirectly be in communication with each other, with or without going through the controller 426. For example, the sensor 422 may be directly coupled to the light source 426.

Figure 5:
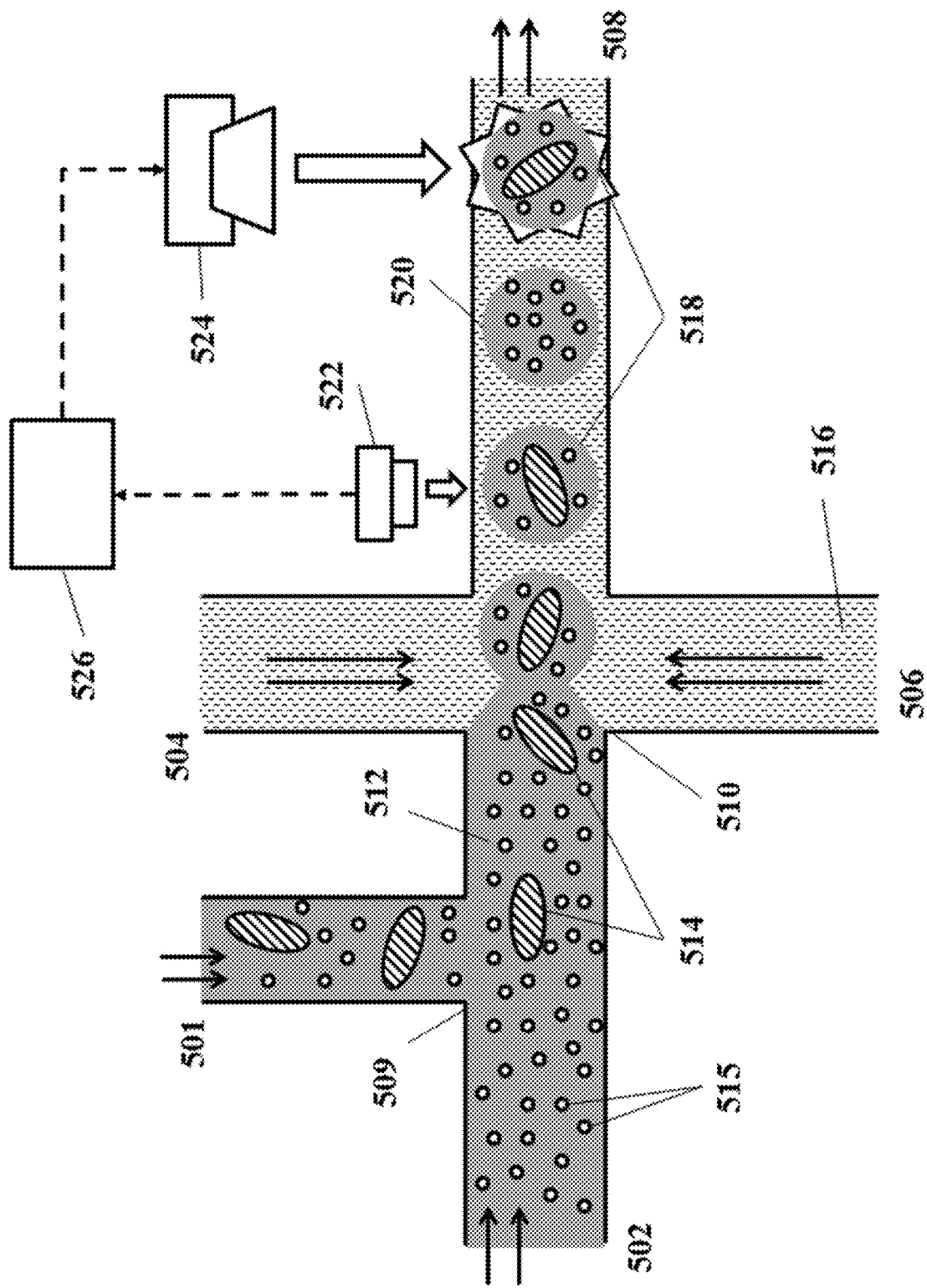
FIG. 5 shows another example of a microfluidic channel structure for selective polymerization of partitions based on occupancy.

FIG. 5 shows another example of a microfluidic channel structure for selective polymerization of partitions (e.g., biological particles therein) based on occupancy.

The emulsion mechanism of FIG. 5 can largely parallel that of FIGS. 1 and 4. As shown in FIG. 5, the channel structure can include channel segments 501, 502, 504, 506 and 508. Channel segments 501 and 502 can communicate at a channel junction 509. Channel segments 502, 504, 506, and 508 can communicate at a channel junction 510. In operation, a first aqueous fluid 512 can be delivered to junction 509 from each of channel segments 502 and 501. Cells 514 can be introduced into the junction 509 via the channel segment 501 as suspensions in the first aqueous fluid 512 flowing along the channel segment 501. The first aqueous fluid 512 may or may not contain suspended field-attractable particles 515. As described elsewhere herein, occupied droplets and unoccupied droplets may be subsequently sorted via the field-attractable particles 515. A second fluid 516 that is immiscible with the aqueous fluid 512 is delivered to the junction 510 from each of channel segments 504 and 506 to create discrete droplets 518, 520 of the first aqueous fluid 512 flowing into channel segment 508, and flowing away from junction 510. A discrete droplet generated may or may not include biological particles 514. Each cell 514 introduced into the droplet can comprise fluorescent labels (such as in accordance with the widely used Fluorescence-Activated Cell Sorting (FACS) mechanism) or other optical labels that allow for detection by an optical sensor.

The second fluid 516 can comprise an oil, such as a fluorinated oil, that includes a fluorosurfactant for stabilizing the resulting droplets, e.g., inhibiting subsequent coalescence of the resulting droplets. Examples of particularly useful partitioning fluids and fluorosurfactants are described for example, in U.S. Patent Application Publication No. 2010/0105112, which is entirely incorporated herein by reference for all purposes.

The generated droplets may comprise two subsets of droplets: (1) occupied droplets 518, containing one or more biological particles 514, and (2) unoccupied droplets 520, not containing any biological particles 514.

A photo polymerization light source 524, such as a laser, can be located downstream of the junction 510 to selectively polymerize occupied droplets. In some instances, the light source 524 can be a lamp or light emitting diode (LED). The light source 524 can generate optical pulses or an electromagnetic beam at a targeted direction. For example, the light source 524 can be configured to only emit electromagnetic waves when an occupied droplet is passing by. The light source 524 can be operatively coupled to a controller 526. The light source 524 can receive instructions from the controller 526 on whether or not a droplet passing by the light source 524, or a droplet expected to pass by the light source at a certain time, is occupied. While FIG. 5 depicts one light source 524, it may be appreciated that there may be a plurality of light sources, each in communication with the controller 526 and/or with each other. For example, a plurality of light sources may each be located at different locations, including different upstream/downstream locations in the fluidic channels. Alternatively, a different polymerization application unit can be used to subject the droplets to a stimulus, such as to trigger polymerization of one or more biological particles therein via heating, cooling, electromagnetic radiation, and/or light. The stimulus can be a chemical stimulus. In some instances, a plurality of the same or different types of polymerization application units can be used at different locations.

A sensor 522 can be configured to sense one or more characteristics of a droplet indicative of whether the droplet is occupied or unoccupied. The sensor 522 may be located downstream of the junction 510. In some instances, the sensor 522 can be an impedance sensor configured to measure bulk impedance when droplets pass by the sensor 522. In some instances, a higher impedance can be measured when an occupied droplet 518 passes by than when an unoccupied droplet 520 passes by. In some instances, the sensor 522 can be an optical sensor configured to measure optical properties of a droplet. The optical sensor and/or a supporting device may be configured to emit a detection signal configured to probe one or more droplets, including for example an electromagnetic signal (e.g., in any wavelength) and/or an acoustic signal. In some instances, the optical sensor and/or a supporting device may comprise an illumination source configured to illuminate the droplet or droplets with one or more types of electromagnetic radiation. In some instances, the electromagnetic radiation can include illumination in one or more of the visible spectrum, infrared spectrum, the ultraviolet spectrum, and ionizing radiation spectrum. In some instances, the ionizing radiation can include x-rays. The illumination can be transillumination or epi-illumination. Alternatively the sensor 522 may be one or more devices that are configured to provide one or more of optical sensing, thermal sensing, laser imaging, infrared imaging, capacitance sensing, mass sensing, vibration sensing across at least a portion of the electromagnetic spectrum, and magnetic induction sensing. The sensor 522 may collect sensor data on one or more properties (e.g., optical properties, impendence properties, etc.) or characteristics of a droplet 414. For example, the one or more properties or characteristics determined by the sensor 522 can be indicative of a certain type of droplets, such as occupied droplets, unoccupied droplets, singularly occupied droplets, multiply occupied droplets, droplets of a certain size or size range, etc.

The sensor 522 can be operatively coupled to the controller 526. For example, the sensor 526 may transmit sensor data (e.g., one or more characteristics indicative of an occupancy of a droplet) to the controller 526. The controller 526 may then use such data, the location of the sensor and/or the location in the fluidic channel at which the occupied droplet 518 was detected, the time the sensor 522 detected an occupied droplet 518, fluid flow in the channel segment 508, location of the light source 524, time it takes for the sensor 526 to detect and/or transmit data to the controller 526, and/or time it takes for the controller 526 to send instructions to the light source 524, to send instructions to the light source 524 on whether or not to emit an electromagnetic wave to polymerize a droplet. For example, using such data, the controller 526 may determine whether a droplet passing by the sensor 522 location at a certain time is occupied or unoccupied. Based on the fluid flow rate in channel segment 508, the controller 526 may determine whether a droplet passing by the light source 524 at a certain time (e.g., assuming time it takes for droplet to travel from the sensor 522 location to the location of the light source 524 site is the same every time) is occupied or unoccupied.

While FIG. 5 depicts one sensor 522, it may be appreciated that there may be a plurality of sensors, each in communication with the controller 526 and/or with each other. For example, there can be a plurality of sensors upstream or downstream of the junction 510 at different locations, for example, detecting the occupancy of a droplet.

While FIG. 5 depicts one controller 526 operatively coupled to both the sensor 522 and the light source 524, a separate controller can be coupled to the sensor 522 and a separate controller can be coupled to the light source 524. The separate controllers may or may not be in communication with each other. In some instances, there may be a plurality of controllers (e.g., two controllers to sensor 522), wherein each controller may or may not be in communication with each other. The controller 526 may send instructions to sensor 522 and/or the light source 524 via wired connection and/or wireless connection (e.g., Wi-Fi, Bluetooth, NFC, etc.). The controller 522 may receive data from the sensor 522 and/or the light source 524 via wired connection and/or wireless connection (e.g., Wi-Fi, Bluetooth, NFC, etc.). In some instances, the components can be directly or indirectly be in communication with each other, with or without going through the controller 526. For example, the sensor 522 may be directly coupled to the light source 526.

Figure 6:
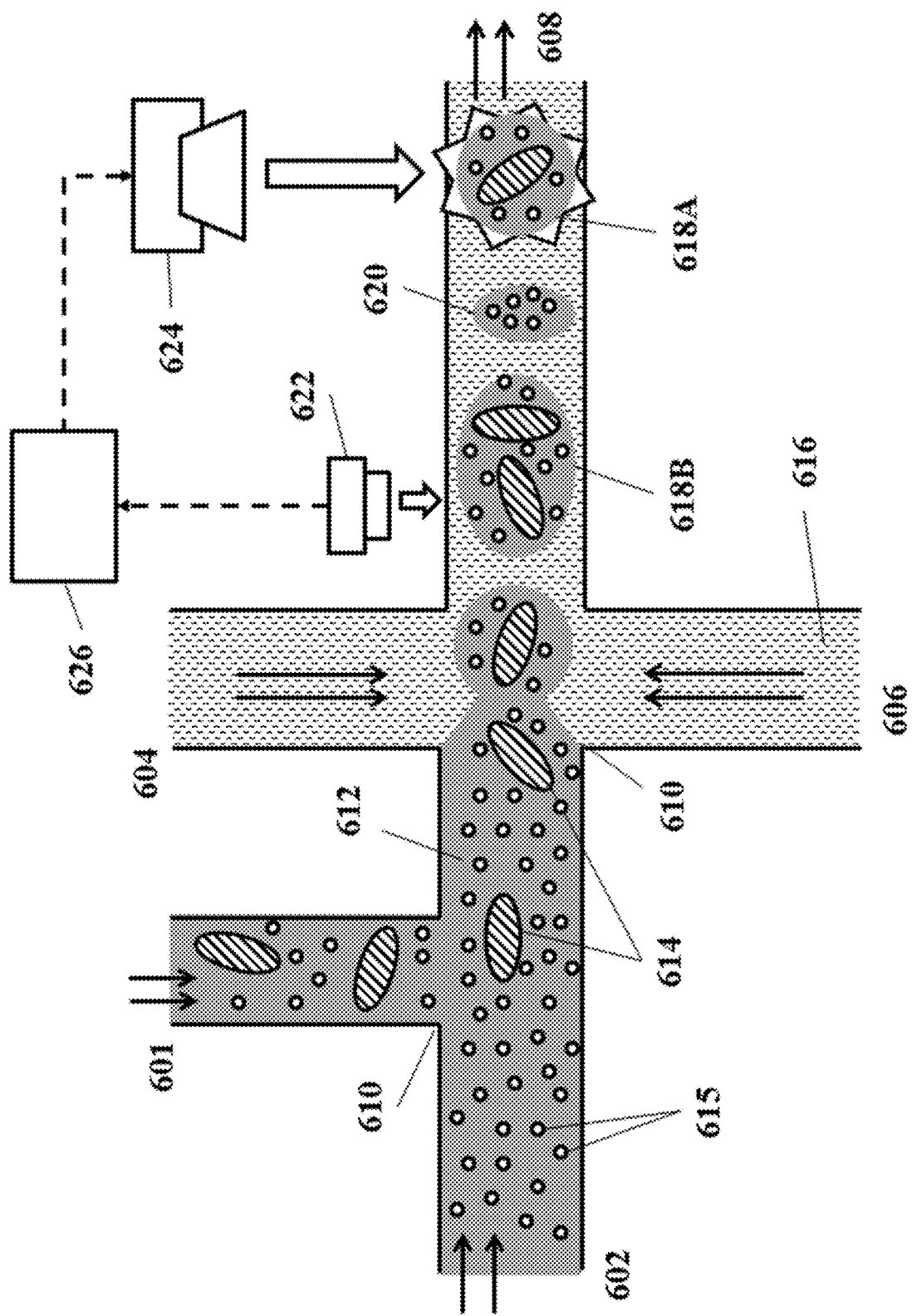
FIG. 6 shows an example of a microfluidic channel structure for selective polymerization of partitions based on droplet size.

FIG. 6 shows an example of a microfluidic channel structure for selective polymerization of partitions based on droplet size.

The emulsion mechanism of FIG. 6 can largely parallel that of FIGS. 1, 4, and 5. As shown in FIG. 6, the channel structure can include channel segments 601, 602, 604, 606 and 608. Channel segments 601 and 602 can communicate at a channel junction 609. Channel segments 602, 604, 606, and 608 can communicate at a channel junction 610. In operation, a first aqueous fluid 612 can be delivered to junction 609 from each of channel segments 602 and 601. Cells 614 can be introduced into the junction 609 via the channel segment 601 as suspensions in the first aqueous fluid 612 flowing along the channel segment 601. The first aqueous fluid 612 may or may not contain suspended field-attractable particles 615. As described elsewhere herein, occupied droplets and unoccupied droplets may be subsequently sorted via the field-attractable particles 615. A second fluid 616 that is immiscible with the aqueous fluid 612 is delivered to the junction 610 from each of channel segments 604 and 606 to create discrete droplets 618, 620 of the first aqueous fluid 612 flowing into channel segment 608, and flowing away from junction 610. A discrete droplet generated may or may not include biological particles 614. Each cell 614 introduced into the droplet can comprise fluorescent labels (such as in accordance with the widely used Fluorescence-Activated Cell Sorting (FACS) mechanism).

In some instances, each droplet generated by the above emulsion may be of substantially uniform size that is appropriate (and/or acceptable) for feeding to subsequent single cell applications. In some instances, some droplets may be of substantially uniform size, and some droplets may have different sizes. For example, the droplets generated can have a size distribution where at least about 10%, 20%, 30%, 40%, 50%, 55%, 60%, 65%, 70%, 75%, 80%, 85%, 90%, 95%, 96%, 97%, 98%, 99% or a higher percentage of droplets generated can have a substantially uniform size. Alternatively, less than 10% of the droplets generated can have a size distribution where less than 10% of the droplets generated have a substantially uniform size. The system and methods described herein may selectively polymerize only droplets (e.g., polymerize biological particles contained therein the droplets) that have the appropriate (and/or acceptable) size and/or droplets that are occupied.

The second fluid 616 can comprise an oil, such as a fluorinated oil, that includes a fluorosurfactant for stabilizing the resulting droplets, e.g., inhibiting subsequent coalescence of the resulting droplets. Examples of particularly useful partitioning fluids and fluorosurfactants are described for example, in U.S. Patent Application Publication No. 2010/0105112, which is entirely incorporated herein by reference for all purposes.

The generated droplets may comprise two subsets of droplets: (1) occupied droplets 618A, 618B, containing one or more biological particles 614, and (2) unoccupied droplets 620, not containing any biological particles 614. As described above, within the subset of occupied droplets 618A, 618B, some droplets may have the appropriate size (e.g., droplet 618A) and some droplets may have an inappropriate size (e.g., droplet 618B).

A photo polymerization light source 624, such as a laser, can be located downstream of the junction 610 to selectively polymerize occupied droplets. In some instances, the light source 624 can be a lamp or light emitting diode (LED). The light source 624 can generate optical pulses or an electromagnetic beam at a targeted direction. For example, the light source 624 can be configured to only emit electromagnetic waves when an occupied droplet is passing by. The light source 624 can be operatively coupled to a controller 626. The light source 624 can receive instructions from the controller 626 on whether or not a droplet passing by the light source 624, or a droplet expected to pass by the light source at a certain time, is occupied. While FIG. 6 depicts one light source 624, it may be appreciated that there may be a plurality of light sources, each in communication with the controller 626 and/or with each other. For example, a plurality of light sources may each be located at different locations, including different upstream/downstream locations in the fluidic channels. Alternatively, a different polymerization application unit can be used to subject the droplets to a stimulus, such as to trigger polymerization via heating, cooling, electromagnetic radiation, and/or light. The stimulus can be a chemical stimulus. In some instances, a plurality of the same or different types of polymerization application units can be used at different locations.

A sensor 622 can be configured to sense one or more characteristics of a droplet indicative of whether the droplet is occupied or unoccupied. The sensor 622 may be located downstream of the junction 610. In some instances, the sensor 622 can be an impedance sensor configured to measure bulk impedance when droplets pass by the sensor 622. In some instances, a higher impedance can be measured when a larger droplet (e.g., droplet 618B) passes by than when a smaller droplet (e.g., droplet 618A or droplet 620) passes by. In some instances, a higher impedance can be measured when an occupied droplet (e.g., droplets 618A, 618B) passes by than when an unoccupied droplet (e.g., droplet 620) passes by. In some instances, the sensor 622 can be an optical sensor configured to measure optical properties of a droplet. The optical sensor and/or a supporting device may be configured to emit a detection signal configured to probe one or more droplets, including for example an electromagnetic signal (e.g., in any wavelength) and/or an acoustic signal. In some instances, the optical sensor and/or a supporting device may comprise an illumination source configured to illuminate the droplet or droplets with one or more types of electromagnetic radiation. In some instances, the electromagnetic radiation can include illumination in one or more of the visible spectrum, infrared spectrum, the ultraviolet spectrum, and ionizing radiation spectrum. In some instances, the ionizing radiation can include x-rays. The illumination can be transillumination or epi-illumination. Alternatively the sensor 622 may be one or more devices that are configured to provide one or more of optical sensing, thermal sensing, laser imaging, infrared imaging, capacitance sensing, mass sensing, vibration sensing across at least a portion of the electromagnetic spectrum, and magnetic induction sensing. The sensor 622 may collect sensor data on one or more properties (e.g., optical properties, impendence properties, etc.) or characteristics of a droplet. For examples, the one or more properties and/or other characteristics of a droplet measured by the sensor 622 can be indicative of a size and/or an occupancy of the droplet.

The sensor 622 can be operatively coupled to the controller 626. For example, the sensor 626 may transmit sensor data (e.g., size and/or occupancy of a droplet) to the controller 626. The controller 626 may then use such data, the location of the sensor and/or the location in the fluidic channel at which the occupancy and/or size of a droplet was detected, the time the sensor 622 detected, fluid flow in the channel segment 608, location of the light source 624, time it takes for the sensor 626 to detect and/or transmit data to the controller 626, and/or time it takes for the controller 626 to send instructions to the light source 624, to send instructions to the light source 624 on whether or not to emit an electromagnetic wave to polymerize a droplet. For example, assuming that the fluid flow rates in the channel segment 608 are substantially constant, the controller 626 may determine whether a droplet passing by a sensor 622 location at a certain time is occupied or unoccupied. Based on the fluid flow rate in channel segment 608, the controller 626 may determine whether a droplet passing by the light source 624 at a certain time (e.g., assuming time it takes for droplet to travel from the sensor 622 location to the location of the light source 624 site is the same every time) is occupied or unoccupied.

While FIG. 6 depicts one sensor 622, it may be appreciated that there may be a plurality of sensors, each in communication with the controller 626 and/or with each other. For example, there can be a plurality of sensors upstream or downstream of the junction 610 at different locations, for example, detecting the occupancy of a droplet. In some instances, a separate sensor can detect occupancy of a droplet and a separate sensor can detect size of the droplet. The separate sensors may or may not detect such characteristics at the same upstream/downstream location of the fluid channel.

While FIG. 6 depicts one controller 626 operatively coupled to both the sensor 622 and the light source 624, a separate controller can be coupled to the sensor 622 and a separate controller can be coupled to the light source 624. The separate controllers may or may not be in communication with each other. In some instances, there may be a plurality of controllers (e.g., two controllers to sensor 622), wherein each controller may or may not be in communication with each other. The controller 626 may send instructions to sensor 622 and/or the light source 624 via wired connection and/or wireless connection (e.g., Wi-Fi, Bluetooth, NFC, etc.). The controller 622 may receive data from the sensor 622 and/or the light source 624 via wired connection and/or wireless connection (e.g., Wi-Fi, Bluetooth, NFC, etc.). In some instances, the components can be directly or indirectly be in communication with each other, with or without going through the controller 626. For example, the sensor 622 may be directly coupled to the light source 626.

In some instances, a plurality of droplets, wherein a first subset comprises polymerized droplets and a second subset comprises pre-polymerized droplets can be further sorted based on polymerization status, such as via solvent exchange. For example, the pre-polymerized droplets can be washed away during solvent exchange to isolate the polymerized droplets.

The separation systems and methods for sorting and/or selective polymerization described above and further below may achieve super Poissonian loading. For example, the droplets can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of droplets that is isolated are occupied droplets (e.g., containing at least one biological particle). Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of the first subset of droplets can be occupied droplets. In some instances, at least about 97%, 98%, 99%, or a higher percentage of a second subset of droplets that is isolated are unoccupied droplets (e.g., not containing any biological particle and not containing any barcode carrying beads). Alternatively, less than about 97% of the second subset of droplets can be unoccupied droplets. The separation systems and methods described above and below may achieve super Poissonian monodispersity. For example, the droplets can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of droplets that is isolated are within a given droplet size range. Such monodispersity may be greater than or equal to 1%, 2%, 3%, 4%, 5%, 10%, 20%, 30%, 40%, 50%, 60%, 70%, 80%, 90%, 95%, or higher. Alternatively, less than about 97% of the first subset of droplets can be within a given droplet size range.

As described elsewhere herein, a cell bead can be formed after the polymerization process, such as via the selective polymerization systems and methods described herein. Alternatively, a different polymerization procedure can be used. For example, cell beads can be formed by selectively polymerizing one or more biological particles within droplets, such as via methods described in relation to FIG. 4-6. In another example, a cell bead can be formed by polymerizing one or more biological particles that are suspended in a first solvent, such as oil. In some cases, a plurality of biological particles (e.g., cells) may be hardened and/or polymerized in bulk by applying a stimulus (e.g., light, chemical, temperature, etc.) to the first solvent carrying the plurality of biological particles (e.g., as suspensions). Upon formation, a plurality of cell beads may be surrounded by the first solvent, such as an oil. In order to promote integration of a cell bead into a droplet with a gel bead, the cell bead may be placed into an aqueous environment by a solvent exchange process. The solvent exchange process may comprise the operations of collecting a plurality of cell beads surrounded by oil (for instance, in an Eppendorf tube or other collection vessel), removing excess oil (for instance, by pipetting), adding a ligation buffer (such as a 3× ligation buffer), vortexing, adding a buffer (such as a 1× 1H,1H,2H, 2H-perfluoro-1-octanol (PFO) buffer), vortexing, centrifugation, and separation. The separation operation may comprise magnetic separation.

Each of the cell beads may comprise field-attractable particles (e.g., paramagnetic particles). For example, cell beads comprising field-attractable particles can be formed using the systems and methods described elsewhere herein (e.g., field-attractable particles 115 in FIG. 1 are suspended in fluids that form emulsion droplets which can be polymerized to form cell beads). The magnetic separation may be accomplished by using a magnetic separating apparatus to pull cell beads containing paramagnetic particles away from unwanted remaining oil and solvents. In some instances, the magnetic separating apparatus can be a field application unit as described elsewhere herein (e.g., the same type of field application unit 216 in FIG. 2A, field application unit 316 in FIG. 3). For instance, the magnetic separation apparatus may be used to pull cell beads containing paramagnetic particles away from the ligation buffer and PFO to allow removal of the ligation buffer and PFO (for instance by pipetting). The cell beads containing paramagnetic particles may then be suspended in a ligation buffer and vortexed. The cell beads containing paramagnetic particles may again be separated magnetically and the ligation buffer may be removed. This cycle of re-suspension, vortexing, and magnetic separation may be repeated until the cell beads are clean. For instance, the cycle may be repeated 1, 2, 3, 4, 5, 6, 7, 8, 9, 10, or more than 10 times. The cell beads may then be placed into an aqueous medium.

Once the cell beads are in an aqueous medium, the cell beads may be further treated. For instance, the cell beads in aqueous solution may be filtered (for instance, using a 70 µm filter) to remove clumps and/or large cell beads from the solution. In some cases, additional reagents may be added to and/or removed from the aqueous medium to further process the cell beads. The cell beads may then be combined into droplets with gel beads, as described herein.

Also provided herein are the microfluidic devices used for partitioning the cells as described above. Such microfluidic devices can comprise channel networks for carrying out the partitioning process like those set forth in FIGS. 1, 4, 5, and 6. These microfluidic devices can comprise channel networks, such as those described herein, for partitioning cells into separate partitions, and co-partitioning such cells with oligonucleotide barcode library members, e.g., disposed on beads. These channel networks can be disposed within a solid body, e.g., a glass, semiconductor or polymer body structure in which the channels are defined, where those channels communicate at their termini with reservoirs for receiving the various input fluids, and for the ultimate deposition of the partitioned cells, etc., from the output of the channel networks. By way of example, and with reference to FIG. 1, a reservoir fluidly coupled to channel 102 may be provided with an aqueous suspension of cells 114, while a reservoir coupled to another channel (not shown) may be provided with an aqueous suspension of beads carrying the oligonucleotides. Channel segments 106 and 108 may be provided with a non-aqueous solution, e.g., an oil, into which the aqueous fluids are partitioned as droplets at the channel junction 110. Finally, an outlet reservoir may be fluidly coupled to channel 108 into which the partitioned cells and beads can be delivered and from which they may be harvested. As will be appreciated, while described as reservoirs, it will be appreciated that the channel segments may be coupled to any of a variety of different fluid sources or receiving components, including tubing, manifolds, or fluidic components of other systems.

Also provided are systems that control flow of these fluids through the channel networks e.g., through applied pressure differentials, centrifugal force, electrokinetic pumping, compressors, capillary or gravity flow, or the like.

The systems and methods described herein may allow for the production of one or more droplets containing a single biological particle and/or a single bead. The systems and methods may also allow for the production of one or more droplets containing a single biological particle and more than one bead, one or more droplets containing more than one biological particle and a single bead, or one or more droplets containing more than one biological particle and more than one bead. The systems and methods described herein may allow for the production of one or more cell beads containing a single biological particle and/or a single bead. The systems and methods may also allow for selective polymerization of occupied droplets and/or appropriately sized droplets, which mixture of polymerized and pre-polymerized droplets may or may not be subjected to subsequent sorting.

Figure 7:
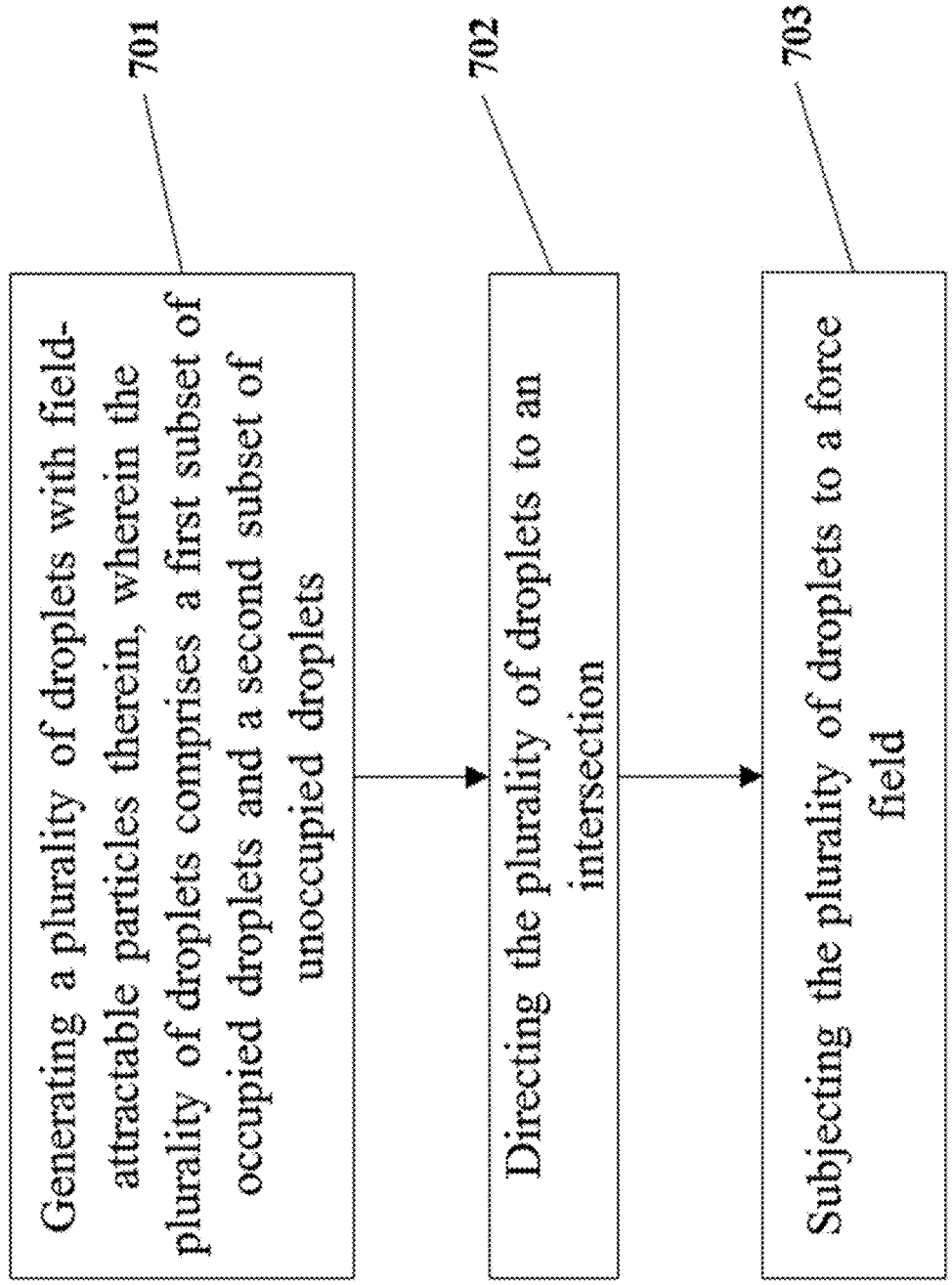
FIG. 7 shows a flowchart for a method of sorting occupied droplets and unoccupied droplets.

FIG. 7 shows a flowchart for a method of sorting occupied droplets and unoccupied droplets, wherein an occupied droplet contains at least a biological particle (cell) and/or a barcode carrying bead (particle).

In an operation 701, a plurality of droplets are generated upon bringing a first phase in contact with a second phase, wherein the first phase and the second phase are immiscible. Each of the plurality of droplets comprises some number and/or concentration of field-attractable particles. A first subset of the plurality of droplets contains therein cells and/or barcode carrying particles, and a second subset of the plurality of droplets does not contains therein cells and/or barcode carrying particles. A given droplet in the first subset of the plurality of droplets may contain a single cell or a plurality of cells. A given droplet in the first subset of the plurality of droplets may contain a single barcode carrying particle or a plurality of barcode carrying particles. A given droplet of the first subset of the plurality of droplets may contain a fewer number and/or lower concentration of field-attractable particles than a given droplet of the second subset of the plurality of droplets, on account of the volume occupied by the cell and/or barcode carrying particles contained in the occupied droplet.

In an operation 702, the plurality of droplets is directed along the first channel towards an intersection of the first channel. The intersection can be between the first channel, a second channel, and a third channel. The plurality of droplets may be directed along one or more channels in a flow of fluid (e.g., either the first phase or the second phase used to generate the droplets), such as via a fluid flow unit.

In an operation 703, the plurality of droplets is subject to a force field, such as via a field application unit, at or near the intersection. The force field can be a magnetic field and/or an electric field. The plurality of droplets can be subjected to the force field under conditions sufficient to separate the first subset of droplets from the second subset of the droplets, wherein upon separation, the first subset of droplets flows along the second channel, and the second subset of droplets flows along the third channel. For example, the field-attractable particles can be paramagnetic particles when a magnetic field is applied. The field-attractable particles can be conductive particles when an electric field is applied. Because a given droplet in the second subset of the plurality of droplets has a greater number and/or concentration of field-attractable particles than a given droplet in the first subset of the plurality of droplets, for the same field applied, a stronger force can act on a given droplet in the second subset of droplets than on a given droplet in the first subset of droplets. The force differential may separate the two subsets, such as by influencing a greater deviation in fluid flow path direction for a given droplet in the second subset of droplets than for a given droplet in the first subset of droplets.

The method of FIG. 7 may isolate occupied droplets (e.g., first subset of droplets) with super-Poissonian loading. For example, a plurality of droplets can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of droplets that is isolated are occupied droplets (e.g., containing at least one biological particle). Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of droplets of a separated subset of the plurality of droplets may be occupied droplets.

The method of FIG. 7 may be similarly used to isolate occupied particles from a plurality of particles containing occupied and unoccupied particles. For example, a plurality of particles may be generated to comprise a first subset of occupied particles (containing a biological particle and/or a barcode carrying particle therein) and a second subset of unoccupied particles, wherein particles of both the first subset and the second subset comprise field-attractable particles. A given particle of the first subset may contain a fewer number and/or lower concentration of field-attractable particles than a given particle of the second subset, on account of the volume occupied by the cell and/or barcode carrying particles contained in the occupied particle. The plurality of particles may be directed along a first channel towards an intersection of the first channel. The intersection can be between the first channel, a second channel, and a third channel.

The plurality of particles can be subject to a force field, such as via a field application unit, at or near the intersection. The force field can be a magnetic field and/or an electric field. The plurality of particles can be subjected to the force field under conditions sufficient to separate the first subset from the second subset, wherein upon separation, the first subset of particles flows along the second channel, and the second subset of particles flows along the third channel. For example, the field-attractable particles can be paramagnetic particles when a magnetic field is applied. The field-attractable particles can be conductive particles when an electric field is applied. Because a given particle in the second subset has a greater number and/or concentration of field-attractable particles than a given particle in the first subset, for the same field applied, a stronger force can act on a given particle in the second subset than on a given particle in the first subset. The force differential may separate the two subsets, such as by influencing a greater deviation in fluid flow path direction for a given particle in the second subset than for a given particle in the first subset.

The method of FIG. 7 may isolate occupied particles (e.g., first subset of particles) with super-Poissonian loading. For example, a plurality of particles can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of particles that is isolated are occupied particles (e.g., containing at least one biological particle). Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of particles of a separated subset of the plurality of particles may be occupied particles.

Figure 8:
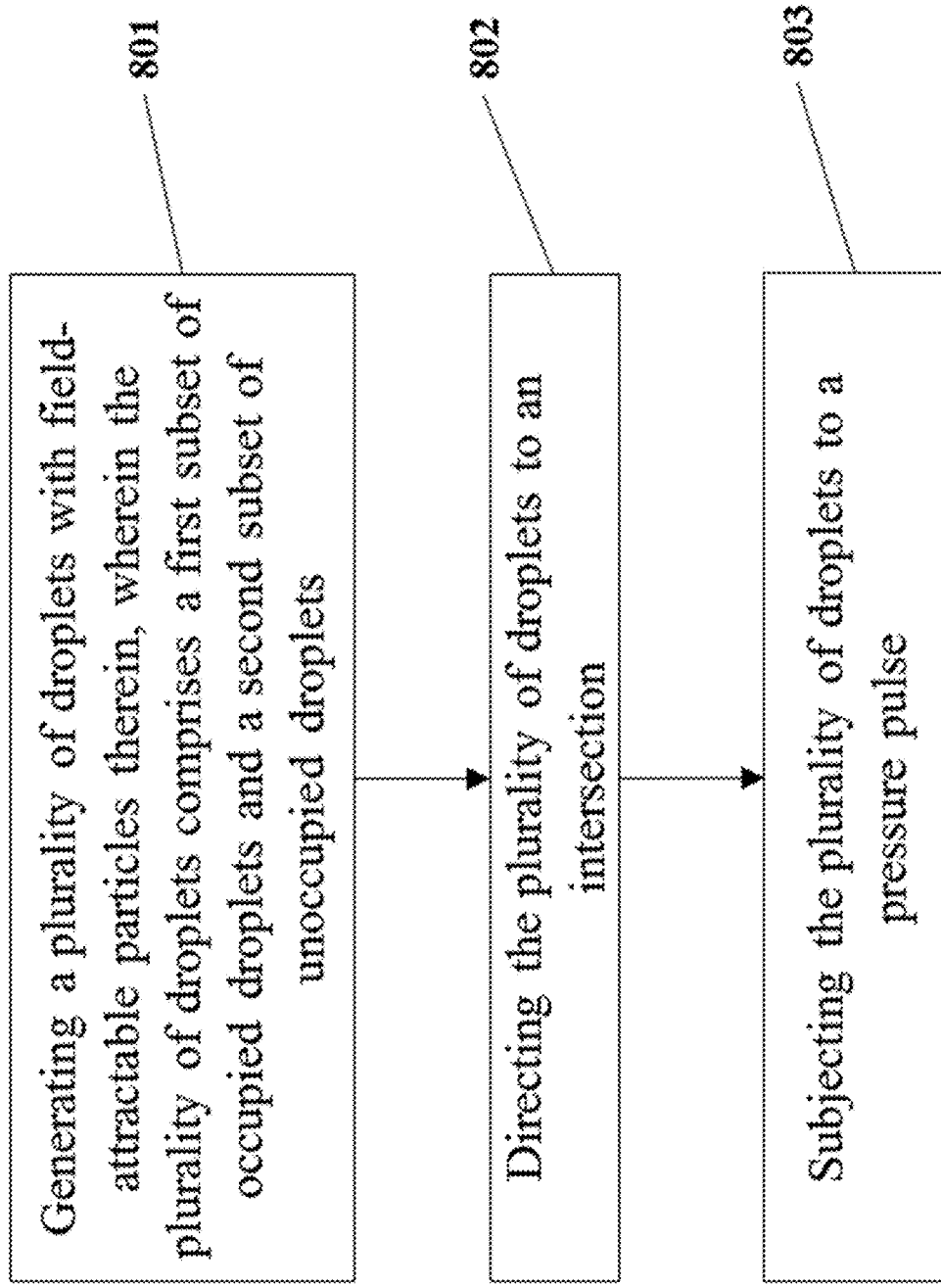
FIG. 8 shows a flowchart for another method of sorting occupied droplets and unoccupied droplets.

FIG. 8 shows a flowchart for a method of sorting occupied droplets and unoccupied droplets, wherein an occupied droplet contains at least a biological particle (cell) and/or a barcode carrying bead (particle).

In an operation 801, a plurality of droplets are generated upon bringing a first phase in contact with a second phase, wherein the first phase and the second phase are immiscible. Each of the plurality of droplets comprises may or may not comprise some number and/or concentration of field-attractable particles. The presence of field-attractable particles is not required. A first subset of the plurality of droplets contains therein cells and/or barcode carrying particles, and a second subset of the plurality of droplets does not contain therein cells and/or barcode carrying particles. A given droplet in the first subset of the plurality of droplets may contain a single cell or a plurality of cells. A given droplet in the first subset of the plurality of droplets may contain a single barcode carrying particle or a plurality of barcode carrying particles.

In an operation 802, the plurality of droplets is directed along the first channel towards an intersection of the first channel. The intersection can be between the first channel, a second channel, and a third channel. The plurality of droplets may be directed along one or more channels in a flow of fluid (e.g., either the first phase or the second phase used to generate the droplets), such as via a fluid flow unit.

In an operation 803, the plurality of droplets is subject to a pressure pulse, such as via a pressure application unit, at or near the intersection. The pressure pulse can be provided as a positive pressure pulse or a negative pressure pulse. The plurality of droplets can be subjected to the pressure pulse under conditions sufficient to separate the first subset of droplets from the second subset of the droplets, wherein upon separation, the first subset of droplets flows along the second channel, and the second subset of droplets flows along the third channel. Because a given droplet in the second subset of the plurality of droplets has different particle and/or suspension characteristics in the fluid than a given droplet in the first subset of the plurality of droplets, for the same pressure pulse applied, a different hydrodynamic force can act on a given droplet in the second subset of droplets than on a given droplet in the first subset of droplets. The pressure pulse may separate the two subsets, such as by influencing a greater deviation in fluid flow path direction for a given droplet in the second subset of droplets than for a given droplet in the first subset of droplets.

In some instances, a sensor, such as an impedance sensor or an optical sensor, may measure one or more characteristics of a droplet at an upstream location of the intersection. The sensing data may be indicative of the occupancy of the droplet. The sensing data may be transmitted to a controller. The controller may use the sensing data to determine the occupancy of the droplet and instruct the pressure application unit to generate or not generate pressure pulses to separate the first subset from the second subset.

The method of FIG. 8 may isolate occupied droplets (e.g., first subset of droplets) with super-Poissonian loading. For example, a plurality of droplets can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of droplets that is isolated are occupied droplets (e.g., containing at least one biological particle). Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of droplets of a separated subset of the plurality of droplets may be occupied droplets.

The method of FIG. 8 may be similarly used to isolate cell beads from a plurality of particles containing both cell beads and unoccupied particles. For example, a plurality of particles may be generated to comprise a first subset of occupied particles (containing a biological particle and/or a barcode carrying particle therein) and a second subset of unoccupied particles. The presence of field-attractable particles is not required. The plurality of particles may be directed along a first channel towards an intersection of the first channel. The intersection can be between the first channel, a second channel, and a third channel. The plurality of particles may be subject to a pressure pulse, such as via a pressure application unit, at or near the intersection. The pressure pulse can be provided as a positive pressure pulse or a negative pressure pulse.

The plurality of particles can be subjected to the pressure pulse under conditions sufficient to separate the first subset of particles (e.g., cell beads) from the second subset of the particles (e.g., unoccupied particles), wherein upon separation, the first subset of particles flows along the second channel, and the second subset of particles flows along the third channel. Because a given particle in the second subset of the plurality of particles has different particle and/or suspension characteristics in the fluid than a given particle in the first subset of the plurality of particles, for the same pressure pulse applied, a different hydrodynamic force can act on a given particle in the second subset of particles than on a given particle in the first subset of particles. The pressure pulse may separate the two subsets, such as by influencing a greater deviation in fluid flow path direction for a given particle in the second subset of particles than for a given particle in the first subset of particles.

In some instances, a sensor, such as an impedance sensor or an optical sensor, may measure one or more characteristics of a particle at an upstream location of the intersection. The sensing data may be indicative of the occupancy of the particle. The sensing data may be transmitted to a controller. The controller may use the sensing data to determine the occupancy of the particle and instruct the pressure application unit to generate or not generate pressure pulses to separate the first subset from the second subset.

The method of FIG. 8 may isolate cell beads (e.g., first subset of particles) with super-Poissonian loading. For example, a plurality of particles can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of particles that is isolated are cell beads (e.g., containing at least one biological particle). Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of particles of a separated subset of the plurality of particles may be cell beads.

Figure 9:
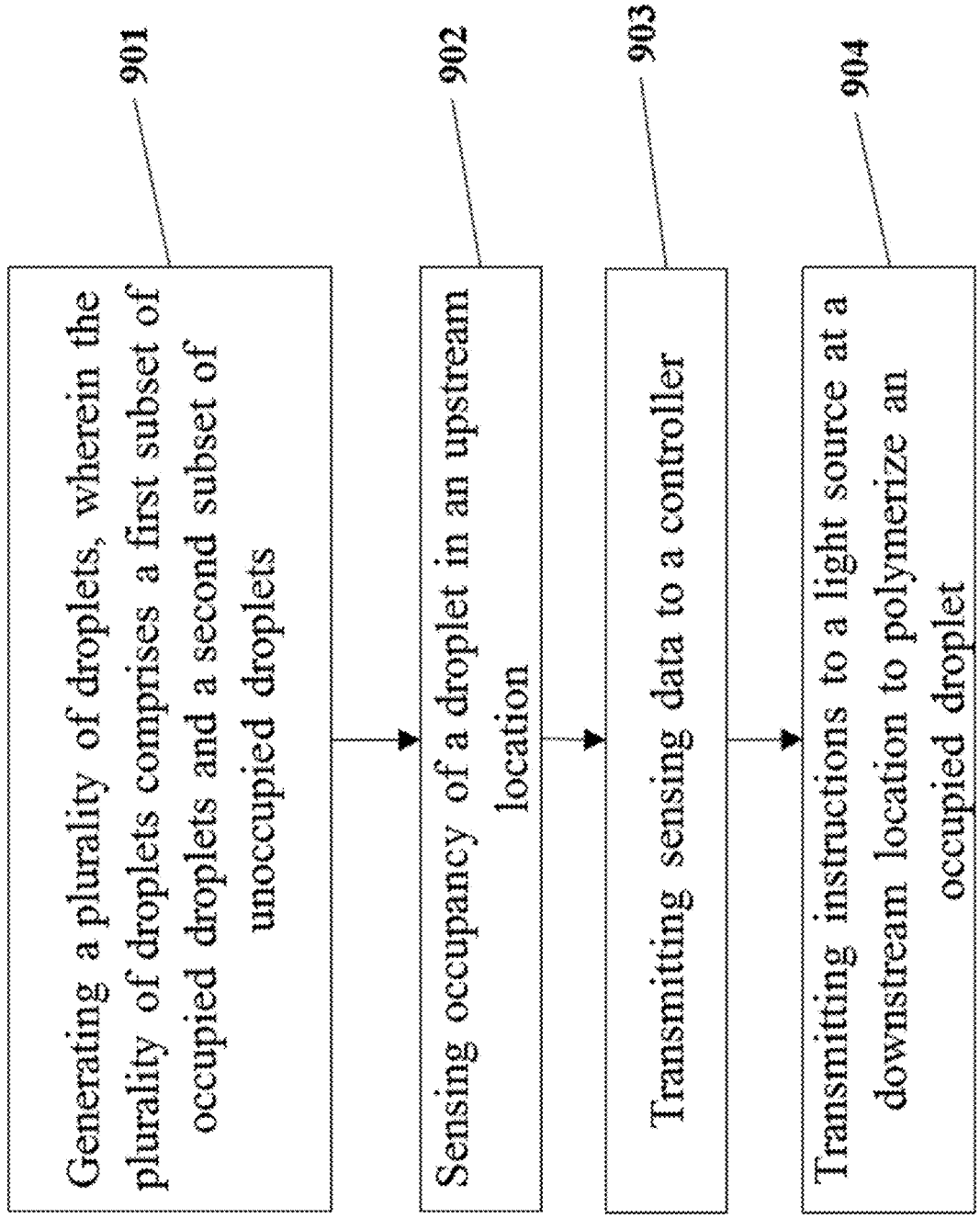
FIG. 9 shows a flowchart for a method of selectively polymerizing occupied droplets.

FIG. 9 shows a flowchart for a method of selectively polymerizing occupied droplets, wherein an occupied droplet contains at least a biological particle (cell) and/or a barcode carrying bead (particle).

In an operation 901, a plurality of droplets are generated upon bringing a first phase in contact with a second phase, wherein the first phase and the second phase are immiscible. Each of the plurality of droplets comprises may or may not comprise some number and/or concentration of field-attractable particles. The presence of field-attractable particles is not required. A first subset of the plurality of droplets contains therein cells and/or barcode carrying particles, and a second subset of the plurality of droplets does not contain therein cells and/or barcode carrying particles. A given droplet in the first subset of the plurality of droplets may contain a single cell or a plurality of cells. A given droplet in the first subset of the plurality of droplets may contain a single barcode carrying particle or a plurality of barcode carrying particles.

In an operation 902, at an upstream location, a sensor detects and/or measures one or more characteristics of a droplet passing through the upstream location. The one or more characteristics can be indicative of the occupancy of the droplet. In some instances, the sensor can be an impedance sensor configured to detect bulk impedance as a droplet or a plurality of droplets passes through the upstream location. A higher impedance can be measured for occupied droplets than for unoccupied droplets. In some instances, the sensor can be an optical sensor configured to detect one or more optical characteristics of the droplet as the droplet passes through the upstream location. Alternatively, a plurality of the same or different types of sensors can be used to detect and/or measure one or more characteristics of the droplet passing through the upstream location.

In an operation 903, the sensing data may transmitted to a controller. For example, the sensor can be operatively coupled to the controller. The controller can determine, based at least in part on the sensor data, whether a droplet passing through a downstream location is occupied or unoccupied. For example, the controller may use such sensor data, the location of the sensor and/or the location in the fluidic channel at which the occupancy of a droplet was detected, the time the sensor detected the occupancy of a droplet, fluid flow rate of one or more channels, location of the light source, time it takes for the sensor to detect and/or transmit data to the controller, and/or time it takes for the controller to send instructions to the light source, to send instructions to the light source on whether or not to emit an electromagnetic wave to polymerize a droplet.

Alternatively, in some instances, the sensor may detect the presence of a cell suspended in a fluid flow before the droplets are generated (e.g., at the intersection), and use such sensor data of the presence of the cell, and other information (e.g., location, times, fluid flow rates) to determine whether a droplet at a downstream location is occupied.

In an operation 904, the controller may transmit instruction to a light source at a downstream location to emit electromagnetic waves to polymerize a droplet if the droplet is occupied, and not to emit electromagnetic waves if the droplet is unoccupied, thus letting the unoccupied droplet pass through unpolymerized. Alternatively, other polymerization application units can be used in place of, or in conjunction with the light source.

The method of FIG. 9 may polymerize occupied droplets (e.g., first subset of droplets) with super-Poissonian distribution. The separation systems and methods disclosed herein may achieve super Poisson loading. For example, at least about 5%, 10%, 15%, 20%, 25%, 30%, 40%, 50%, 60%, 70%, 80%, 90%, 95%, 96%, 97%, 98%, 99%, or greater of a plurality of droplets that are polymerized can be occupied droplets. Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of polymerized droplets may be occupied droplets.

Figure 10:
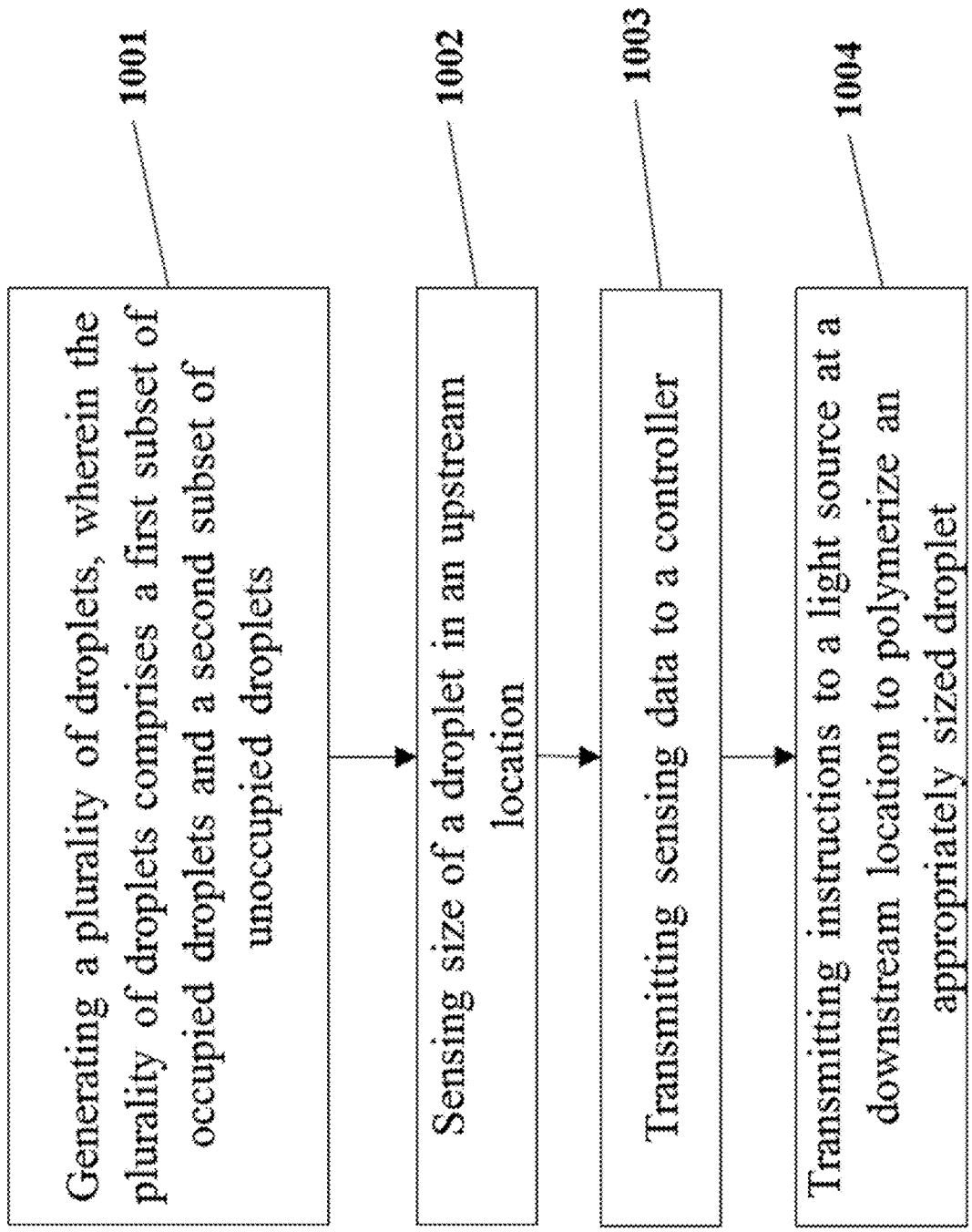
FIG. 10 shows a flowchart for a method of selectively polymerizing appropriately sized droplets.

FIG. 10 shows a flowchart for a method of selectively polymerizing appropriately sized droplets.

In an operation 1001, a plurality of droplets are generated upon bringing a first phase in contact with a second phase, wherein the first phase and the second phase are immiscible. Each of the plurality of droplets comprises may or may not comprise some number and/or concentration of field-attractable particles. The presence of field-attractable particles is not required. A first subset of the plurality of droplets contains therein cells and/or barcode carrying particles, and a second subset of the plurality of droplets does not contain therein cells and/or barcode carrying particles. A given droplet in the first subset of the plurality of droplets may contain a single cell or a plurality of cells. A given droplet in the first subset of the plurality of droplets may contain a single barcode carrying particle or a plurality of barcode carrying particles.

In an operation 1002, at an upstream location, a sensor detects and/or measures one or more characteristics of a droplet passing through the upstream location. The one or more characteristics can be indicative of a size of the droplet. In some instances, the sensor can be an impedance sensor configured to detect bulk impedance as a droplet or a plurality of droplets passes through the upstream location. A higher impedance can be measured for larger droplets than for smaller droplets. In some instances, the sensor can be an optical sensor configured to detect one or more optical characteristics of the droplet as the droplet passes through the upstream location. Alternatively, a plurality of the same or different types of sensors can be used to detect and/or measure one or more characteristics of the droplet passing through the upstream location.

In an operation 1003, the sensing data may transmitted to a controller. For example, the sensor can be operatively coupled to the controller. The controller can determine, based at least in part on the sensor data, whether a droplet passing through a downstream location is appropriately sized or inappropriately sized. For example, the controller may use such sensor data, the location of the sensor and/or the location in the fluidic channel at which the size of a droplet was detected, the time the sensor detected the size of a droplet, fluid flow rate of one or more channels, location of the light source, time it takes for the sensor to detect and/or transmit data to the controller, and/or time it takes for the controller to send instructions to the light source, to send instructions to the light source on whether or not to emit an electromagnetic wave to polymerize a droplet.

In an operation 1004, the controller may transmit instruction to a light source at a downstream location to emit electromagnetic waves to polymerize a droplet if the droplet is appropriately sized, and not to emit electromagnetic waves if the droplet is inappropriately sized, thus letting the inappropriately sized droplet pass through unpolymerized. Alternatively, other polymerization application units can be used in place of, or in conjunction with the light source.

The method of FIG. 10 may polymerize appropriately sized droplets (e.g., first subset of droplets) with super-Poissonian distribution. For example, at least about 5%, 10%, 15%, 20%, 25%, 30%, 40%, 50%, 60%, 70%, 80%, 90%, 95%, 96%, 97%, 98%, 99%, or greater of a plurality of droplets that is polymerized can be appropriately sized droplets. Alternatively, less than about 97% of polymerized droplets may be appropriately sized droplets.

In some instances, the methods of FIG. 9 and FIG. 10 can be combined such that one or more sensors detect one or more characteristics of a droplet at an upstream location (or upstream locations), wherein the one or more characteristics of the droplet are indicative of both a size and an occupancy of the droplet, and transmits the sensor data to a controller. The controller transmits instructions to a light source at a downstream location to polymerize the droplet only if the droplet is both appropriately sized and occupied.

In another aspect, provided is a passive mechanism for sorting occupied droplets from unoccupied droplets. The passive mechanism may not require application of external forces (e.g., magnetic field, electric field, pressure pulse, etc.) on the droplets to achieve sorting. The passive mechanism may sort droplets based at least in part on mechanical properties of the droplets. For example, the passive mechanism may sort droplets based at least in part on properties such as deformability and surface tension (e.g., surface interface energy) of the droplets. In some instances, due to the presence of one or more biological particles in an occupied droplet, the occupied droplet may demonstrate lower deformability and/or higher surface tension properties than unoccupied droplets, making occupied droplets 'harder' or 'stiffer' than unoccupied droplets. Thus, when a plurality of droplets comprising both a first subset of occupied droplets and a second subset of unoccupied droplets is directed to pass through an aperture which is smaller in size than a diameter of a given droplet in the plurality of droplets, only those droplets capable of deforming (e.g., unoccupied droplets having higher deformability properties) may pass through the aperture, trapping the occupied droplets, thereby sorting the occupied droplets from the unoccupied droplets.

Figure 11:
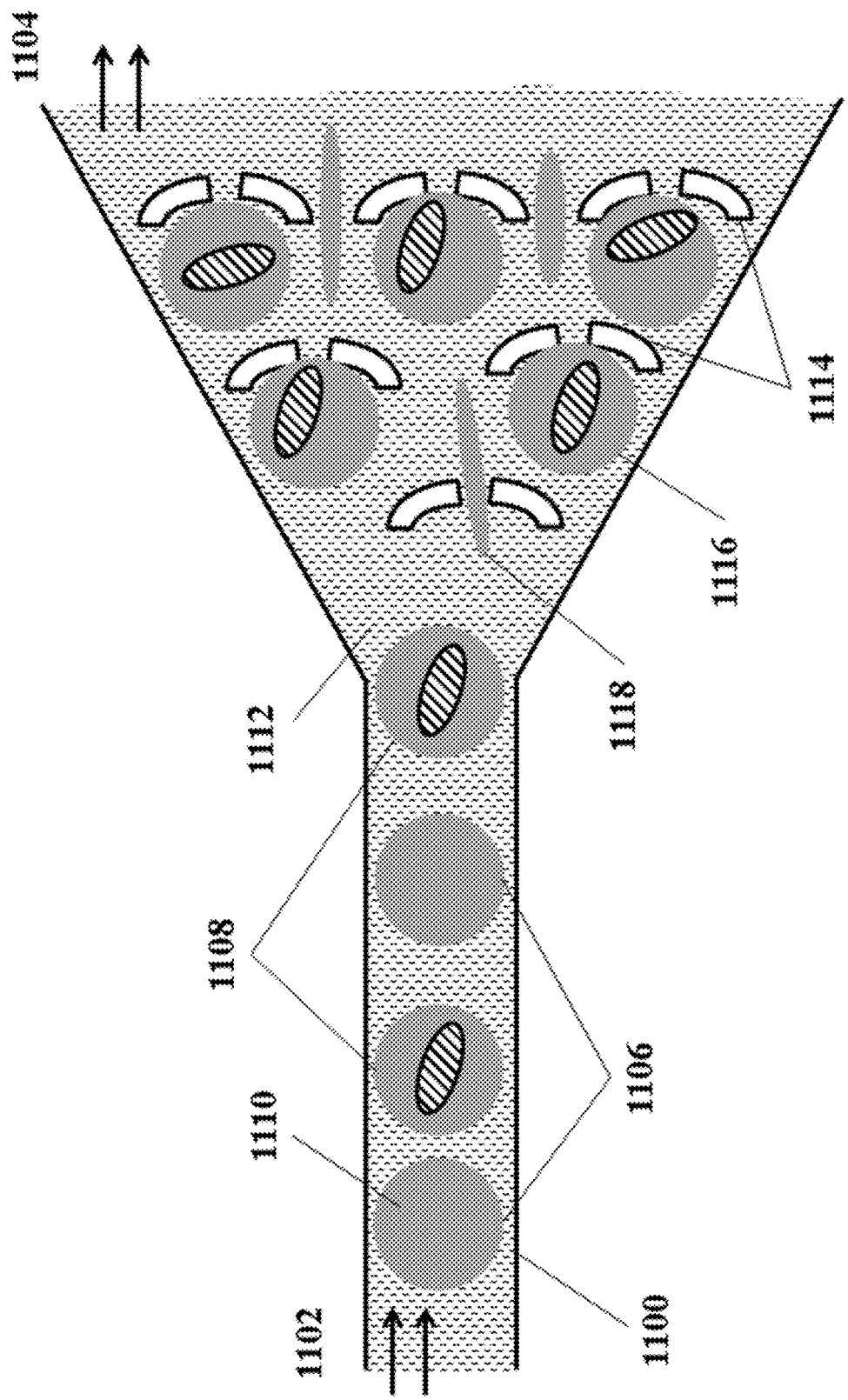
FIG. 11 shows an example of a microfluidic channel structure for separating occupied droplets from unoccupied droplets.

FIG. 11 shows a schematic example of a microfluidic channel structure for separating occupied droplets from unoccupied droplets. As described elsewhere herein, when droplets are generated, there may be at least a first subset population of occupied droplets containing one or more biological particles and at least a second subset population of unoccupied droplets not containing any biological particles. In some cases, the droplets may additionally contain one or more barcode carrying beads. For example, a droplet may have only a biological particle, a droplet may have only a barcode carrying bead, a droplet may have both a biological particle and a barcode carrying bead, or a droplet may have neither biological particles nor barcode carrying beads. In some cases, the majority of occupied partitions (e.g., droplets) can include no more than one biological particle per occupied partition and, in some cases, some of the generated partitions can be unoccupied (e.g., by any biological particle). In some cases, though, some of the occupied partitions may include more than one biological particle. In some cases, the partitioning process may be controlled such that fewer than 25% of the occupied partitions contain more than one biological particle, fewer than 20% of the occupied partitions have more than one biological particle, or fewer than 10% or even fewer than 5% of the occupied partitions include more than one biological particle per partition.

As shown in FIG. 11, the channel structure can include a channel segment 1100 with an entrance 1102 and exit 1104. In some instances, the outflow channel 108 of the emulsion carrying the generated droplets in FIG. 1 can be upstream of the channel segment 1100. A fluid flow unit (not shown) can be configured to facilitate flow of fluid in the channel structure.

In operation, a plurality of discrete droplets, each comprising a first aqueous fluid 1100 can flow as emulsions in a second fluid 1112, wherein the second fluid 1112 is immiscible to the first aqueous fluid 1110. The droplets being transported along channel segment 1100 can comprise a first subset of droplets 1108 that are each occupied with at least a biological particle and/or a barcode carrying bead and a second subset of droplets 1110 that are each unoccupied. As described above, a given unoccupied droplet can have a higher deformability and/or lower surface tension property than a given occupied droplet, due to the presence of one or more biological particles in the occupied droplet.

The channel segment 1100 can comprise a plurality of entrapment structures 1114. An entrapment structure can define an aperture. A size of the aperture may be less than a diameter (or other size dimension) of a droplet. A size of the aperture may be less than a minimum dimension of a droplet. In some instances, the size of the aperture can be at most about 90%, 80%, 70%, 60%, 50%, 45%, 40%, 35%, 30%, 25%, 20%, 15%, 10%, or 5% of the diameter of a droplet (in a pre-deformed state). The size of the aperture can be less than about 5% of the diameter of a droplet. Alternatively, the size of the aperture can be greater than 50%, 60%, 70%, 80%, 90%, 100%, 150%, or 200% of the diameter of a droplet. The size of the aperture can be greater than the diameter of the droplet. When a plurality of droplets comprising both a first subset of occupied droplets 1108 and a second subset of unoccupied droplets 1110 is directed to pass through entrapment structures 1114 defining apertures which is smaller in size than a diameter of a given droplet in the plurality of droplets, only those droplets deforming 1118 (e.g., unoccupied droplets 1110 having higher deformability properties) such that at least one dimension of the droplet is less than a size of the aperture may pass through one or more apertures defined by the entrapment structures 1114. Because occupied droplets 1108 may be 'harder' or 'stiffer,' due to a presence of one or more biological particles in the droplets, the occupied droplets may resist deformation, at least from deforming to a size smaller than a size of the aperture, and remain trapped by the entrapment structures 1114.

In some embodiments, there may exist more entrapment structures 1114 (and thus more apertures) in the channel structure than there are droplets 1106, 1108 passing through the channel structure. Beneficially, when the occupied droplets 1108 are prevented from flowing through the entrapment structures 1114, and the occupied droplets 1108 clog (or block) some apertures of the entrapment structures 1114, the unoccupied droplets 1110 may still deform and flow through other apertures. After sorting, the entrapment structures 1114 may retain from the plurality of droplets only the first subset of occupied droplets 1108. The unoccupied droplets 1104 may flow through all entrapment structures 1114 and exit the channel segment 1100 to a separate compartment, such as for recycling or discarding. While FIG. 11 shows exemplary configurations and a layout of entrapment structures in the channel structure, the configurations and layout of entrapment structures are not limited as such. For example, an entrapment structure can be a single plate with a plurality of apertures (e.g., holes) defined in the plate. The plate can be planar, curved, and/or a combination thereof. The channel structure and the entrapment structures 1114 can be configured such that a droplet from the plurality of droplets passes through at least one entrapment structure (and aperture defined therein). After entrapment and/or sorting of the occupied droplets, the fluid flow unit (not shown) can be configured to reverse a fluid flow direction to collect the occupied droplets from the entrapment structures.

In some instances, the fluid flow unit may comprise a compressor to provide positive pressure at an upstream location to direct the fluid from the upstream location to flow to a downstream location. In some instances, the fluid flow unit may comprise a pump to provide negative pressure at a downstream location to direct the fluid from an upstream location to flow to the downstream location. In some instances, the fluid flow unit may comprise both a compressor and a pump, each at different locations. In some instances, the fluid flow unit may comprise different devices at different locations. The fluid flow unit may comprise an actuator.

The systems and methods described with respect to FIG. 11 may be used to separate occupied particles (e.g., cell beads) from unoccupied particles. As described elsewhere herein, a plurality of particles may comprise a first subset of particles occupied by biological particles (e.g., cells) and a second subset of particles unoccupied by biological particles. As described above, a given unoccupied particle can have a higher deformability and/or lower surface tension property than a given occupied particle (e.g., cell bead) due to the presence of one or more biological particles in the occupied particle. In a channel structure including channel segment 1100 with an entrance 1102 and exit 1104, and comprising the plurality of entrapment structures 1114, the plurality of particles may be directed to flow (e.g., as suspensions in a fluid, e.g., aqueous fluid) along the channel segment 1100 from entrance 1102 to exit 1104 across the plurality of entrapment structures 1114.

An entrapment structure can define an aperture. A size of the aperture may be less than a diameter (or other size dimension) of a particle. A size of the aperture may be less than a minimum dimension of a particle. In some instances, the size of the aperture can be at most about 90%, 80%, 70%, 60%, 50%, 45%, 40%, 35%, 30%, 25%, 20%, 15%, 10%, or 5% of the diameter of a particle (in a pre-deformed state). The size of the aperture can be less than about 5% of the diameter of a particle. Alternatively, the size of the aperture can be greater than 50%, 60%, 70%, 80%, 90%, 100%, 150%, or 200% of the diameter of a particle. The size of the aperture can be greater than the diameter of the particle. When a plurality of particles comprising both a first subset of occupied particles 1108 and a second subset of unoccupied particles 1110 is directed to pass through entrapment structures 1114 defining apertures which is smaller in size than a diameter of a given particle in the plurality of particles, only those particles deforming 1118 (e.g., unoccupied particles 1110 having higher deformability properties) such that at least one dimension of the particle is less than a size of the aperture may pass through one or more apertures defined by the entrapment structures 1114. Because occupied particles 1108 (e.g., cell beads) may be harder or stiffer, due to a presence of one or more biological particles in the particles, the occupied particles may resist deformation, at least from deforming to a size smaller than a size of the aperture, and remain trapped by the entrapment structures 1114.

In some embodiments, there may exist more entrapment structures 1114 (and thus more apertures) in the channel structure than there are particles 1106, 1108 passing through the channel structure. Beneficially, when the occupied particles 1108 are prevented from flowing through the entrapment structures 1114, and the occupied particles 1108 clog (or block) some apertures of the entrapment structures 1114, the unoccupied particles 1110 may still deform and flow through other apertures. After sorting, the entrapment structures 1114 may retain from the plurality of particles only the first subset of occupied particles 1108. The unoccupied particles 1104 may flow through all entrapment structures 1114 and exit the channel segment 1100 to a separate compartment, such as for recycling or discarding.

The separation systems and methods disclosed herein (such as with reference to FIG. 11) may achieve super Poisson loading. For example, the droplets can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of droplets that is isolated are occupied droplets (e.g., containing at least one biological particle). Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of the first subset of droplets can be occupied droplets. In some instances, at least about 97%, 98%, 99%, or a higher percentage of a second subset of droplets that is isolated can be unoccupied droplets (e.g., not containing any biological particle and not containing any barcode carrying beads). Alternatively, less than about 97% of the second subset of droplets can be unoccupied droplets. For example, the plurality of particles can be separated into two subsets such that at least about 5%, 10%, 15%, 20%, 25%, 30%, 40%, 50%, 60%, 70%, 80%, 90%, 95%, 96%, 97%, 98%, 99%, or greater of a first subset of particles that is isolated are cell beads (e.g., containing at least one biological particle). Such occupancy may be greater than or equal to 1%, 2%, 3%, 4%, 5%, 10%, 20%, 30%, 40%, 50%, 60%, 70%, 80%, 90%, 95%, or higher. Alternatively, less than about 97% of the first subset of particles can be cell beads. In some instances, at least about 97%, 98%, 99%, or a higher percentage of a second subset of particles that is isolated can be unoccupied particles (e.g., not containing any biological particle and not containing any barcode carrying beads). Alternatively, less than about 97% of the second subset of particles can be unoccupied particles.

Microfluidic Architectures

In an aspect, provided herein are various microfluidic architectures that can be used in conjunction with the systems and methods described herein.

Figure 12:
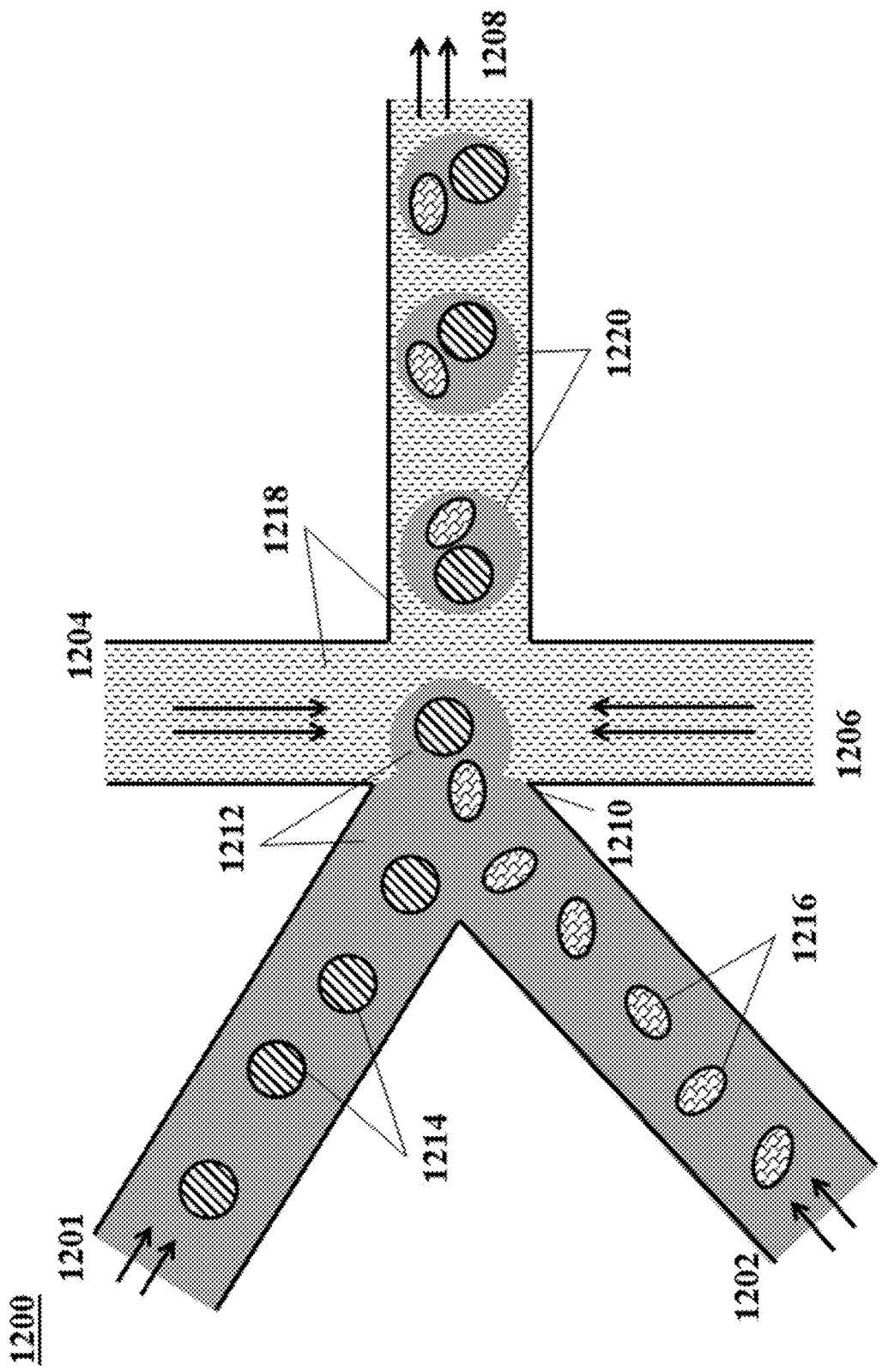
FIG. 12 shows an example of a microfluidic channel structure for delivering barcode carrying beads to droplets.

In accordance with certain aspects, beads may be delivered to droplets. FIG. 12 shows an example of a microfluidic channel structure 1200 for delivering barcode carrying beads to droplets. An example of a barcode carrying bead is described with respect to FIG. 19. The channel structure 1200 can include channel segments 1201, 1202, 1204, 1206 and 1208 communicating at a channel junction 1210. In operation, the channel segment 1201 may transport an aqueous fluid 1212 that includes a plurality of beads 1214 (e.g., with nucleic acid molecules, oligonucleotides, molecular tags) along the channel segment 1201 into junction 1210. The plurality of beads 1214 may be sourced from a suspension of beads. For example, the channel segment 1201 may be connected to a reservoir comprising an aqueous suspension of beads 1214. The channel segment 1202 may transport the aqueous fluid 1212 that includes a plurality of biological particles 1216 along the channel segment 1202 into junction 1210. The plurality of biological particles 1216 may be sourced from a suspension of biological particles. For example, the channel segment 1202 may be connected to a reservoir comprising an aqueous suspension of biological particles 1216. In some instances, the aqueous fluid 1212 in either the first channel segment 1201 or the second channel segment 1202, or in both segments, can include one or more reagents, as further described below. A second fluid 1218 that is immiscible with the aqueous fluid 1212 (e.g., oil) can be delivered to the junction 1210 from each of channel segments 1204 and 1206. Upon meeting of the aqueous fluid 1212 from each of channel segments 1201 and 1202 and the second fluid 1218 from each of channel segments 1204 and 1206 at the channel junction 1210, the aqueous fluid 1212 can be partitioned as discrete droplets 1220 in the second fluid 1218 and flow away from the junction 1210 along channel segment 1208. The channel segment 1208 may deliver the discrete droplets to an outlet reservoir fluidly coupled to the channel segment 1208, where they may be harvested.

As an alternative, the channel segments 1201 and 1202 may meet at another junction upstream of the junction 1210. At such junction, beads and biological particles may form a mixture that is directed along another channel to the junction 1210 to yield droplets 1220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 12015/0292988, which is entirely incorporated herein by reference.

The second fluid 1218 can comprise an oil, such as a fluorinated oil, that includes a fluorosurfactant for stabilizing the resulting droplets, for example, inhibiting subsequent coalescence of the resulting droplets 1220.

A discrete droplet that is generated may include an individual biological particle 1216. A discrete droplet that is generated may include a barcode or other reagent carrying bead 1214. A discrete droplet generated may include both an individual biological particle and a barcode carrying bead, such as droplets 1220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 1200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone, such as through an additional channel or channels upstream of the channel junction. In accordance with other aspects, additionally or alternatively, biological particles may be partitioned along with other reagents, as will be described further below.

Figure 13:
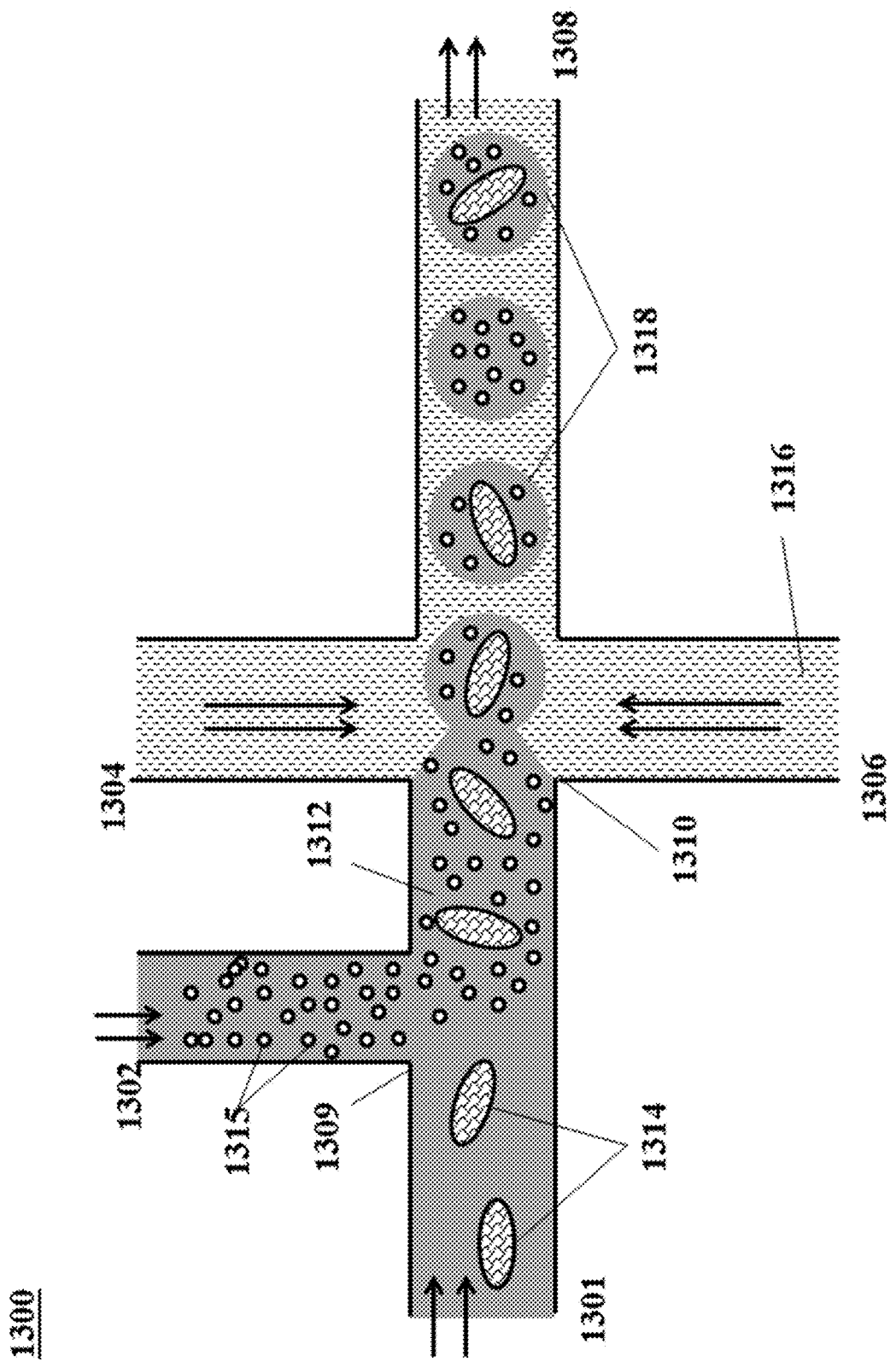
FIG. 13 shows an example of a microfluidic channel structure for co-partitioning biological particles and reagents.

FIG. 13 shows an example of a microfluidic channel structure 1300 for co-partitioning biological particles and reagents. The channel structure 1300 can include channel segments 1301, 1302, 1304, 1306 and 1308. Channel segments 1301 and 1302 communicate at a first channel junction 1309. Channel segments 1302, 1304, 1306, and 1308 communicate at a second channel junction 1310.

In an example operation, the channel segment 1301 may transport an aqueous fluid 1312 that includes a plurality of biological particles 1314 along the channel segment 1301 into the second junction 1310. As an alternative or in addition to, channel segment 1301 may transport beads (e.g., gel beads). The beads may comprise barcode molecules.

For example, the channel segment 1301 may be connected to a reservoir comprising an aqueous suspension of biological particles 1314. Upstream of, and immediately prior to reaching, the second junction 1310, the channel segment 1301 may meet the channel segment 1302 at the first junction 1309. The channel segment 1302 may transport a plurality of reagents 1315 (e.g., lysis agents) suspended in the aqueous fluid 1312 along the channel segment 1302 into the first junction 1309. For example, the channel segment 1302 may be connected to a reservoir comprising the reagents 1315. After the first junction 1309, the aqueous fluid 1312 in the channel segment 1301 can carry both the biological particles 1314 and the reagents 1315 towards the second junction 1310. In some instances, the aqueous fluid 1312 in the channel segment 1301 can include one or more reagents, which can be the same or different reagents as the reagents 1315. A second fluid 1316 that is immiscible with the aqueous fluid 1312 (e.g., oil) can be delivered to the second junction 1310 from each of channel segments 1304 and 1306. Upon meeting of the aqueous fluid 1312 from the channel segment 1301 and the second fluid 1316 from each of channel segments 1304 and 1306 at the second channel junction 1310, the aqueous fluid 1312 can be partitioned as discrete droplets 1318 in the second fluid 1316 and flow away from the second junction 1310 along channel segment 1308. The channel segment 1308 may deliver the discrete droplets 1318 to an outlet reservoir fluidly coupled to the channel segment 1308, where they may be harvested.

The second fluid 1316 can comprise an oil, such as a fluorinated oil, that includes a fluorosurfactant for stabilizing the resulting droplets, for example, inhibiting subsequent coalescence of the resulting droplets 1318.

A discrete droplet generated may include an individual biological particle 1314 and/or one or more reagents 1315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 1300 may have other geometries. For example, a microfluidic channel structure can have more than two channel junctions.

For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 14:
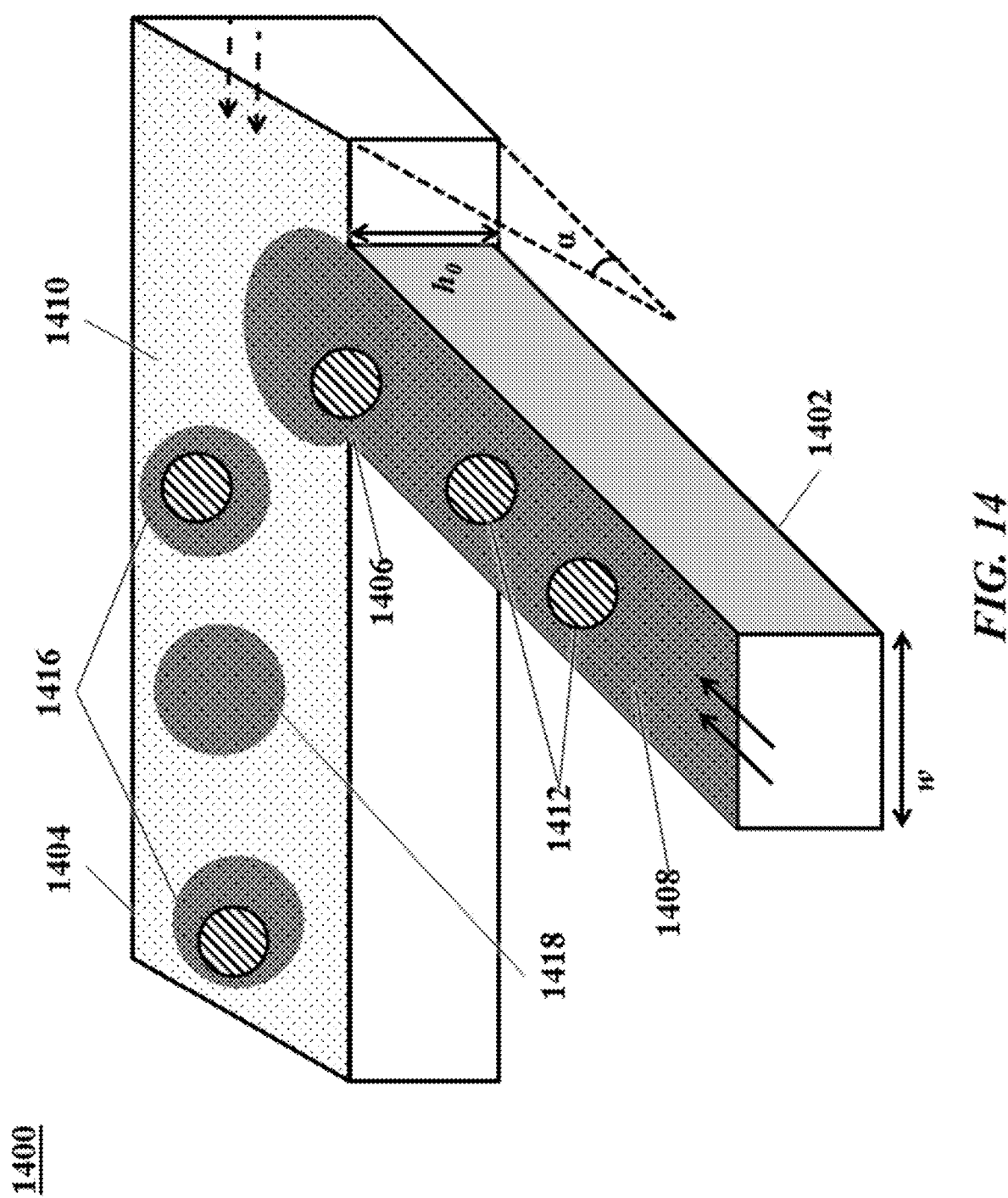
FIG. 14 shows an example of a microfluidic channel structure for the controlled partitioning of beads into discrete droplets.

FIG. 14 shows an example of a microfluidic channel structure for the controlled partitioning of beads into discrete droplets. A channel structure 1400 can include a channel segment 1402 communicating at a channel junction 1406 (or intersection) with a reservoir 1404. The reservoir 1404 can be a chamber. Any reference to "reservoir," as used herein, can also refer to a "chamber." In operation, an aqueous fluid 1408 that includes suspended beads 1412 may be transported along the channel segment 1402 into the junction 1406 to meet a second fluid 1410 that is immiscible with the aqueous fluid 1408 in the reservoir 1404 to create droplets 1416, 1418 of the aqueous fluid 1408 flowing into the reservoir 1404. At the junction 1406 where the aqueous fluid 1408 and the second fluid 1410 meet, droplets can form based on factors such as the hydrodynamic forces at the junction 1406, flow rates of the two fluids 1408, 1410, fluid properties, and certain geometric parameters (e.g., w, $h_0$, α, etc.) of the channel structure 1400. A plurality of droplets can be collected in the reservoir 1404 by continuously injecting the aqueous fluid 1408 from the channel segment 1402 through the junction 1406.

A discrete droplet generated may include a bead (e.g., as in occupied droplets 1416). Alternatively, a discrete droplet generated may include more than one bead. Alternatively, a discrete droplet generated may not include any beads (e.g., as in unoccupied droplet 1418). In some instances, a discrete droplet generated may contain one or more biological particles, as described elsewhere herein. In some instances, a discrete droplet generated may comprise one or more reagents, as described elsewhere herein.

In some instances, the aqueous fluid 1408 can have a substantially uniform concentration or frequency of beads 1412. The beads 1412 can be introduced into the channel segment 1402 from a separate channel (not shown in FIG. 14). The frequency of beads 1412 in the channel segment 1402 may be controlled by controlling the frequency in which the beads 1412 are introduced into the channel segment 1402 and/or the relative flow rates of the fluids in the channel segment 1402 and the separate channel. In some instances, the beads can be introduced into the channel segment 1402 from a plurality of different channels, and the frequency controlled accordingly.

In some instances, the aqueous fluid 1408 in the channel segment 1402 can comprise biological particles. In some instances, the aqueous fluid 1408 can have a substantially uniform concentration or frequency of biological particles. As with the beads, the biological particles can be introduced into the channel segment 1402 from a separate channel. The frequency or concentration of the biological particles in the aqueous fluid 1408 in the channel segment 1402 may be controlled by controlling the frequency in which the biological particles are introduced into the channel segment 1402 and/or the relative flow rates of the fluids in the channel segment 1402 and the separate channel. In some instances, the biological particles can be introduced into the channel segment 1402 from a plurality of different channels, and the frequency controlled accordingly. In some instances, a first separate channel can introduce beads and a second separate channel can introduce biological particles into the channel segment 1402. The first separate channel introducing the beads may be upstream or downstream of the second separate channel introducing the biological particles.

The second fluid 1410 can comprise an oil, such as a fluorinated oil, that includes a fluorosurfactant for stabilizing the resulting droplets, for example, inhibiting subsequent coalescence of the resulting droplets.

In some instances, the second fluid 1410 may not be subjected to and/or directed to any flow in or out of the reservoir 1404. For example, the second fluid 1410 may be substantially stationary in the reservoir 1404. In some instances, the second fluid 1410 may be subjected to flow within the reservoir 1404, but not in or out of the reservoir 1404, such as via application of pressure to the reservoir 1404 and/or as affected by the incoming flow of the aqueous fluid 1408 at the junction 1406. Alternatively, the second fluid 1410 may be subjected and/or directed to flow in or out of the reservoir 1404. For example, the reservoir 1404 can be a channel directing the second fluid 1410 from upstream to downstream, transporting the generated droplets.

The channel structure 1400 at or near the junction 1406 may have certain geometric features that at least partly determine the sizes of the droplets formed by the channel structure 1400. The channel segment 1402 can have a height, $h_0$ and width, w, at or near the junction 1406. By way of example, the channel segment 1402 can comprise a rectangular cross-section that leads to a reservoir 1404 having a wider cross-section (such as in width or diameter). Alternatively, the cross-section of the channel segment 1402 can be other shapes, such as a circular shape, trapezoidal shape, polygonal shape, or any other shapes. The top and bottom walls of the reservoir 1404 at or near the junction 1406 can be inclined at an expansion angle, α. The expansion angle, α, allows the tongue (portion of the aqueous fluid 1408 leaving channel segment 1402 at junction 1406 and entering the reservoir 1404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and α:

$$R_d \approx 0.44\left(1 + 2.2\sqrt{\tan \alpha}\, \frac{w}{h_0}\right)\frac{h_0}{\sqrt{\tan \alpha}}$$

By way of example, for a channel structure with w=21 μm, h=21 μm, and α=3°, the predicted droplet size is 121 μm. In another example, for a channel structure with w=25 h=25 μm, and α=5°, the predicted droplet size is 123 μm. In another example, for a channel structure with w=28 μm, h=28 μm, and α=7°, the predicted droplet size is 124 μm.

In some instances, the expansion angle, α, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 1408 entering the junction 1406 can be between about 0.04 microliters (μL)/minute (min) and about 40 μL/min. In some instances, the flow rate of the aqueous fluid 1408 entering the junction 1406 can be between about 0.01 microliters (μL)/minute (min) and about 100 μL/min. Alternatively, the flow rate of the aqueous fluid 1408 entering the junction 1406 can be less than about 0.01 μL/min. Alternatively, the flow rate of the aqueous fluid 1408 entering the junction 1406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 1408 entering the junction 1406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 1406) between aqueous fluid 1408 channel segments (e.g., channel segment 1402) and the reservoir 1404. Alternatively or in addition, the throughput of droplet generation can be increased by increasing the flow rate of the aqueous fluid 1408 in the channel segment 1402.

Figure 15:
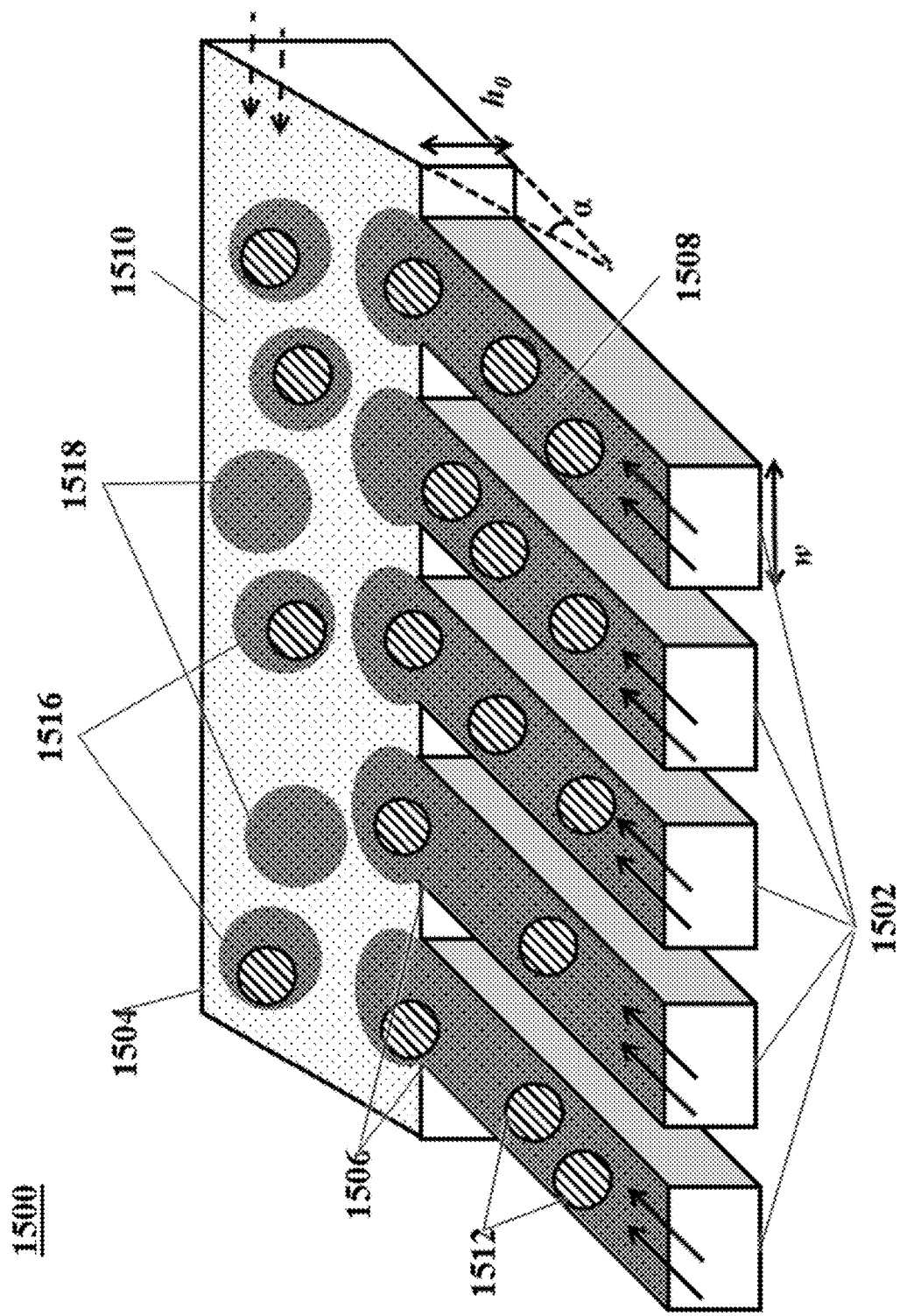
FIG. 15 shows an example of a microfluidic channel structure for increased droplet generation throughput.

FIG. 15 shows an example of a microfluidic channel structure for increased droplet generation throughput. A microfluidic channel structure 1500 can comprise a plurality of channel segments 1502 and a reservoir 1504. Each of the plurality of channel segments 1502 may be in fluid communication with the reservoir 1504. The channel structure 1500 can comprise a plurality of channel junctions 1506 between the plurality of channel segments 1502 and the reservoir 1504. Each channel junction can be a point of droplet generation. The channel segment 1402 from the channel structure 1400 in FIG. 14 and any description to the components thereof may correspond to a given channel segment of the plurality of channel segments 1502 in channel structure 1500 and any description to the corresponding components thereof. The reservoir 1404 from the channel structure 1400 and any description to the components thereof may correspond to the reservoir 1504 from the channel structure 1500 and any description to the corresponding components thereof.

Each channel segment of the plurality of channel segments 1502 may comprise an aqueous fluid 1508 that includes suspended beads 1512. The reservoir 1504 may comprise a second fluid 1510 that is immiscible with the aqueous fluid 1508. In some instances, the second fluid 1510 may not be subjected to and/or directed to any flow in or out of the reservoir 1504. For example, the second fluid 1510 may be substantially stationary in the reservoir 1504. In some instances, the second fluid 1510 may be subjected to flow within the reservoir 1504, but not in or out of the reservoir 1504, such as via application of pressure to the reservoir 1504 and/or as affected by the incoming flow of the aqueous fluid 1508 at the junctions. Alternatively, the second fluid 1510 may be subjected and/or directed to flow in or out of the reservoir 1504. For example, the reservoir 1504 can be a channel directing the second fluid 1510 from upstream to downstream, transporting the generated droplets.

In operation, the aqueous fluid 1508 that includes suspended beads 1512 may be transported along the plurality of channel segments 1502 into the plurality of junctions 1506 to meet the second fluid 1510 in the reservoir 1504 to create droplets 1516, 1518. A droplet may form from each channel segment at each corresponding junction with the reservoir 1504. At the junction where the aqueous fluid 1508 and the second fluid 1510 meet, droplets can form based on factors such as the hydrodynamic forces at the junction, flow rates of the two fluids 1508, 1510, fluid properties, and certain geometric parameters (e.g., w, $h_0$, α, etc.) of the channel structure 1500, as described elsewhere herein. A plurality of droplets can be collected in the reservoir 1504 by continuously injecting the aqueous fluid 1508 from the plurality of channel segments 1502 through the plurality of junctions 1506. Throughput may significantly increase with the parallel channel configuration of channel structure 1500. For example, a channel structure having five inlet channel segments comprising the aqueous fluid 1508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 1502. For example, each channel segment may have the same or different widths at or near its respective channel junction with the reservoir 1504. For example, each channel segment may have the same or different height at or near its respective channel junction with the reservoir 1504. In another example, the reservoir 1504 may have the same or different expansion angle at the different channel junctions with the plurality of channel segments 1502. When the geometric parameters are uniform, beneficially, droplet size may also be controlled to be uniform even with the increased throughput. In some instances, when it is desirable to have a different distribution of droplet sizes, the geometric parameters for the plurality of channel segments 1502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 16:
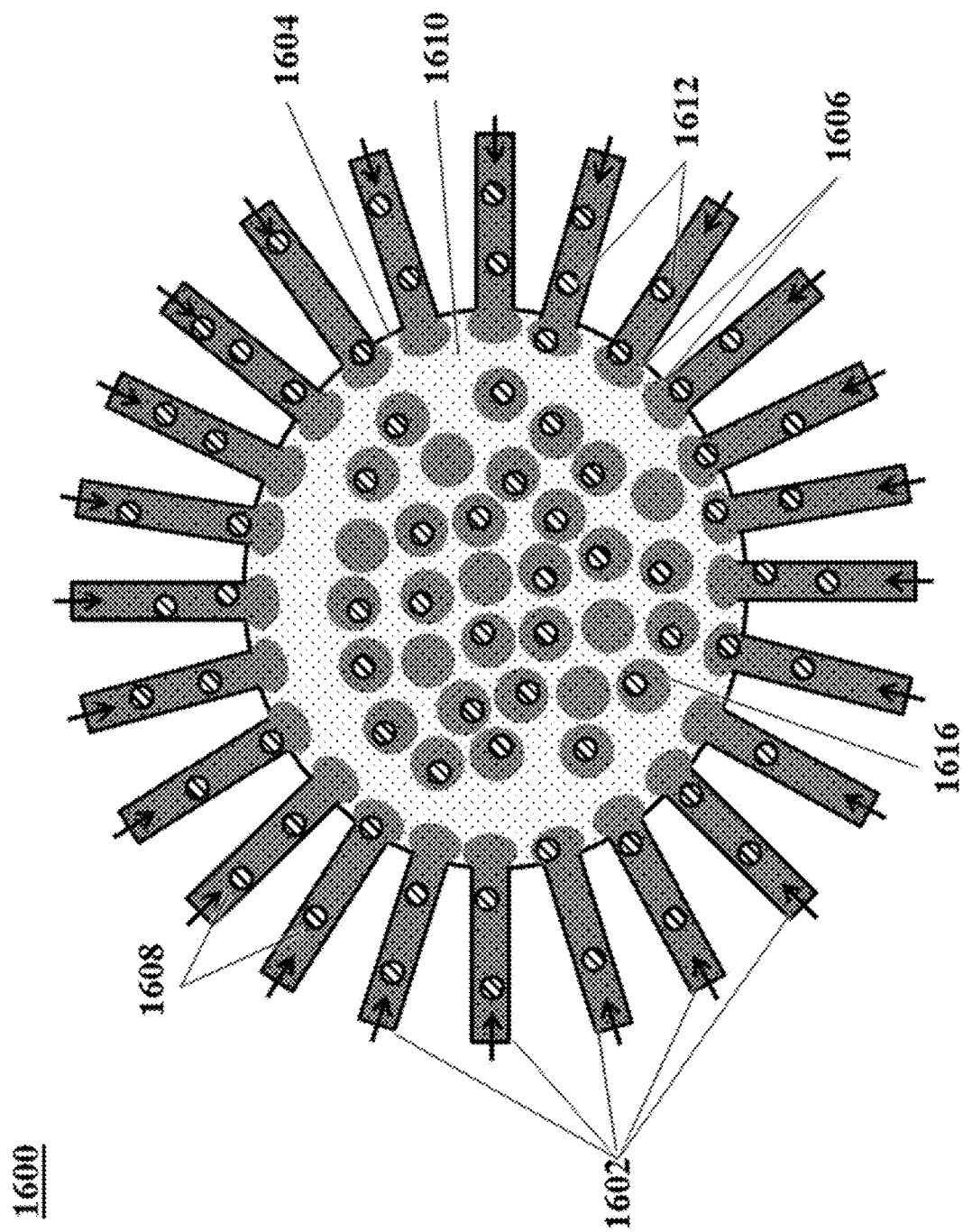
FIG. 16 shows another example of a microfluidic channel structure for increased droplet generation throughput.

FIG. 16 shows another example of a microfluidic channel structure for increased droplet generation throughput. A microfluidic channel structure 1600 can comprise a plurality of channel segments 1602 arranged generally circularly around the perimeter of a reservoir 1604. Each of the plurality of channel segments 1602 may be in fluid communication with the reservoir 1604. The channel structure 1600 can comprise a plurality of channel junctions 1606 between the plurality of channel segments 1602 and the reservoir 1604. Each channel junction can be a point of droplet generation. The channel segment 1402 from the channel structure 1400 in FIG. 14 and any description to the components thereof may correspond to a given channel segment of the plurality of channel segments 1602 in channel structure 1600 and any description to the corresponding components thereof. The reservoir 1404 from the channel structure 1400 and any description to the components thereof may correspond to the reservoir 1604 from the channel structure 1600 and any description to the corresponding components thereof.

Each channel segment of the plurality of channel segments 1602 may comprise an aqueous fluid 1608 that includes suspended beads 1612. The reservoir 1604 may comprise a second fluid 1610 that is immiscible with the aqueous fluid 1608. In some instances, the second fluid 1610 may not be subjected to and/or directed to any flow in or out of the reservoir 1604. For example, the second fluid 1610 may be substantially stationary in the reservoir 1604. In some instances, the second fluid 1610 may be subjected to flow within the reservoir 1604, but not in or out of the reservoir 1604, such as via application of pressure to the reservoir 1604 and/or as affected by the incoming flow of the aqueous fluid 1608 at the junctions. Alternatively, the second fluid 1610 may be subjected and/or directed to flow in or out of the reservoir 1604. For example, the reservoir 1604 can be a channel directing the second fluid 1610 from upstream to downstream, transporting the generated droplets.

In operation, the aqueous fluid 1608 that includes suspended beads 1612 may be transported along the plurality of channel segments 1602 into the plurality of junctions 1606 to meet the second fluid 1610 in the reservoir 1604 to create a plurality of droplets 1616. A droplet may form from each channel segment at each corresponding junction with the reservoir 1604. At the junction where the aqueous fluid 1608 and the second fluid 1610 meet, droplets can form based on factors such as the hydrodynamic forces at the junction, flow rates of the two fluids 1608, 1610, fluid properties, and certain geometric parameters (e.g., widths and heights of the channel segments 1602, expansion angle of the reservoir 1604, etc.) of the channel structure 1600, as described elsewhere herein. A plurality of droplets can be collected in the reservoir 1604 by continuously injecting the aqueous fluid 1608 from the plurality of channel segments 1602 through the plurality of junctions 1606. Throughput may significantly increase with the substantially parallel channel configuration of the channel structure 1600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 1604 may have an expansion angle, α (not shown in FIG. 16) at or near each channel junction. Each channel segment of the plurality of channel segments 1602 may have a width, w, and a height, $h_0$, at or near the channel junction. The geometric parameters, w, $h_0$, and α, may or may not be uniform for each of the channel segments in the plurality of channel segments 1602. For example, each channel segment may have the same or different widths at or near its respective channel junction with the reservoir 1604. For example, each channel segment may have the same or different height at or near its respective channel junction with the reservoir 1604.

The reservoir 1604 may have the same or different expansion angle at the different channel junctions with the plurality of channel segments 1602. For example, a circular reservoir (as shown in FIG. 16) may have a conical, dome-like, or hemispherical ceiling (e.g., top wall) to provide the same or substantially same expansion angle for each channel segments 1602 at or near the plurality of channel junctions 1606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 1602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

FIG. 17A shows a cross-section view of another example of a microfluidic channel structure with a geometric feature for controlled partitioning. A channel structure 1700 can include a channel segment 1702 communicating at a channel junction 1706 (or intersection) with a reservoir 1704. In some instances, the channel structure 1700 and one or more of its components can correspond to any other channel structure described herein and one or more of its components. FIG. 17B shows a perspective view of the channel structure 1700 of FIG. 17A.

An aqueous fluid 1712 comprising a plurality of particles 1716 may be transported along the channel segment 1702 into the junction 1706 to meet a second fluid 1714 (e.g., oil, etc.) that is immiscible with the aqueous fluid 1712 in the reservoir 1704 to create droplets 720 of the aqueous fluid 1712 flowing into the reservoir 1704. At the junction 1706 where the aqueous fluid 1712 and the second fluid 1714 meet, droplets can form based on factors such as the hydrodynamic forces at the junction 1706, relative flow rates of the two fluids 1712, 1714, fluid properties, and certain geometric parameters (e.g., Δh, etc.) of the channel structure 1700. A plurality of droplets can be collected in the reservoir 1704 by continuously injecting the aqueous fluid 1712 from the channel segment 1702 at the junction 1706.

A discrete droplet generated may comprise one or more particles of the plurality of particles 1716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 1712 can have a substantially uniform concentration or frequency of particles 1716. As described elsewhere herein (e.g., with reference to FIG. 14), the particles 1716 (e.g., beads) can be introduced into the channel segment 1702 from a separate channel (not shown in FIG. 17). The frequency of particles 1716 in the channel segment 1702 may be controlled by controlling the frequency in which the particles 1716 are introduced into the channel segment 1702 and/or the relative flow rates of the fluids in the channel segment 1702 and the separate channel. In some instances, the particles 1716 can be introduced into the channel segment 1702 from a plurality of different channels, and the frequency controlled accordingly. In some instances, different particles may be introduced via separate channels. For example, a first separate channel can introduce beads and a second separate channel can introduce biological particles into the channel segment 1702. The first separate channel introducing the beads may be upstream or downstream of the second separate channel introducing the biological particles.

In some instances, the second fluid 1714 may not be subjected to and/or directed to any flow in or out of the reservoir 1704. For example, the second fluid 1714 may be substantially stationary in the reservoir 1704. In some instances, the second fluid 1714 may be subjected to flow within the reservoir 1704, but not in or out of the reservoir 1704, such as via application of pressure to the reservoir 1704 and/or as affected by the incoming flow of the aqueous fluid 1712 at the junction 1706. Alternatively, the second fluid 1714 may be subjected and/or directed to flow in or out of the reservoir 1704. For example, the reservoir 1704 can be a channel directing the second fluid 1714 from upstream to downstream, transporting the generated droplets.

The channel structure 1700 at or near the junction 1706 may have certain geometric features that at least partly determine the sizes and/or shapes of the droplets formed by the channel structure 1700. The channel segment 1702 can have a first cross-section height, $h_1$, and the reservoir 1704 can have a second cross-section height, $h_2$. The first cross-section height, $h_1$, and the second cross-section height, $h_2$, may be different, such that at the junction 1706, there is a height difference of Δh. The second cross-section height, $h_2$, may be greater than the first cross-section height, $h_1$. In some instances, the reservoir may thereafter gradually increase in cross-section height, for example, the more distant it is from the junction 1706. In some instances, the cross-section height of the reservoir may increase in accordance with expansion angle, β, at or near the junction 1706. The height difference, Δh, and/or expansion angle, β, can allow the tongue (portion of the aqueous fluid 1712 leaving channel segment 1702 at junction 1706 and entering the reservoir 1704 before droplet formation) to increase in depth and facilitate decrease in curvature of the intermediately formed droplet. For example, droplet size may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, β, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 1712 entering the junction 1706 can be between about 0.04 microliters (μL)/minute (min) and about 40 μL/min. In some instances, the flow rate of the aqueous fluid 1712 entering the junction 1706 can be between about 0.01 microliters (μL)/minute (min) and about 100 μL/min. Alternatively, the flow rate of the aqueous fluid 1712 entering the junction 1706 can be less than about 0.01 μL/min. Alternatively, the flow rate of the aqueous fluid 1712 entering the junction 1706 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 1712 entering the junction 1706. The second fluid 1714 may be stationary, or substantially stationary, in the reservoir 1704. Alternatively, the second fluid 1714 may be flowing, such as at the above flow rates described for the aqueous fluid 1712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, Δh, being abrupt at the junction 1706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 1706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like.

Likewise, the outlet channel segment (e.g., channel segment 1208, reservoir 1604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Control Systems

Figure 18:
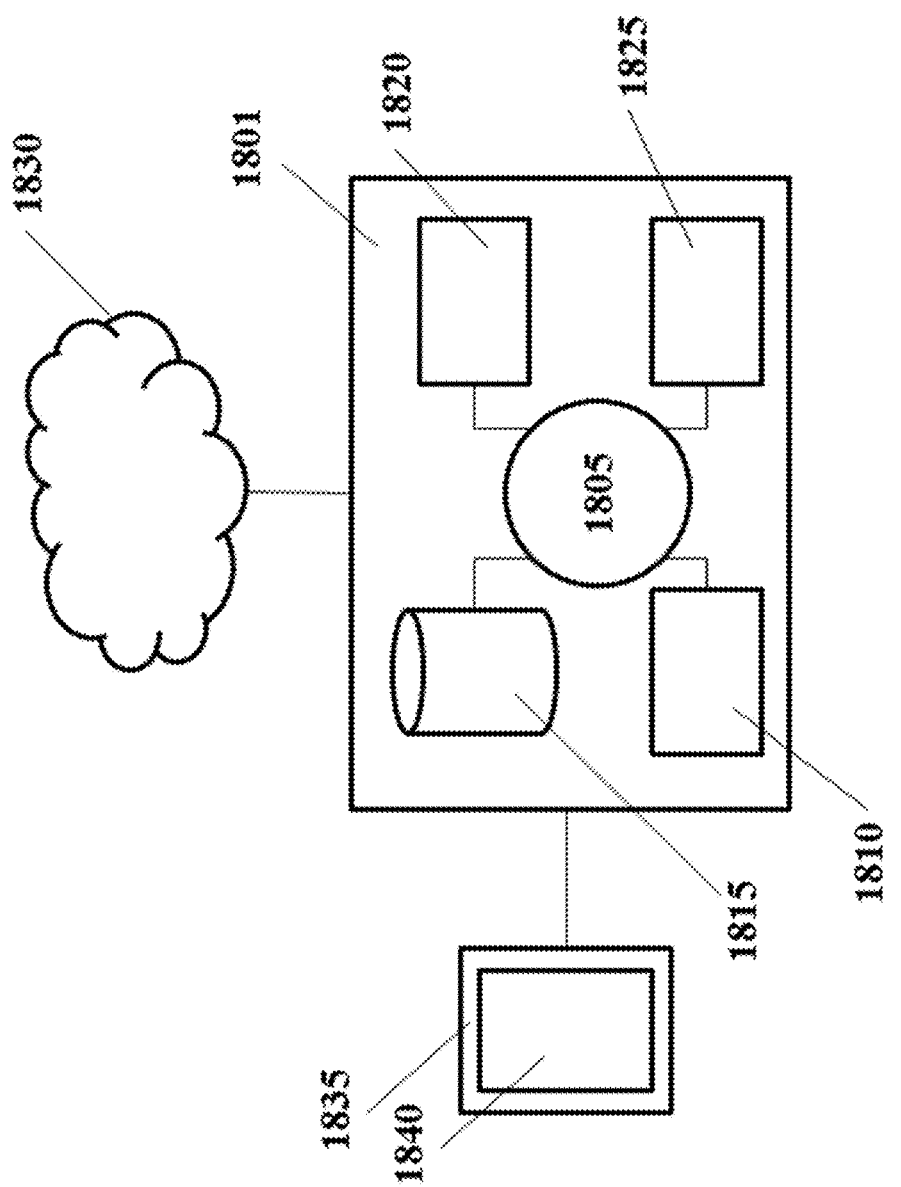
FIG. 18 shows an example computer control system that is programmed or otherwise configured to implement methods provided herein.

The present disclosure provides computer control systems that are programmed to implement methods of the disclosure. FIG. 18 shows a computer system 1801 that is programmed or otherwise configured to (i) sort occupied droplets from unoccupied droplets by including field-attractable particles in each droplet and applying a force field, (ii) sort occupied droplets from unoccupied droplets by applying a pressure pulse, (iii) sort occupied particles (e.g., cell beads) from unoccupied particles using field-attractable particles by applying a force field, (iv) sort occupied particles (e.g., cell beads) from unoccupied particles by applying a pressure pulse, (v) selectively polymerize occupied droplets, and/or (vi) selectively polymerize appropriately sized droplets. The computer system 1801 can regulate various aspects of the present disclosure, such as, for example, the timed exposure of the single biological particle to a variety of chemical or biological operations, regulating fluid flow rate in one or more channels in a microfluidic structure, regulating field strength applied by one or more field application units, regulating pressure pulses applied by one or more pressure application units, and/or regulating timing of polymerization application units. The computer system 1801 can be an electronic device of a user or a computer system that is remotely located with respect to the electronic device. The electronic device can be a mobile electronic device.

The computer system 1801 includes a central processing unit (CPU, also "processor" and "computer processor" herein) 1805, which can be a single core or multi core processor, or a plurality of processors for parallel processing. The computer system 1801 also includes memory or memory location 1810 (e.g., random-access memory, read-only memory, flash memory), electronic storage unit 1815 (e.g., hard disk), communication interface 1820 (e.g., network adapter) for communicating with one or more other systems, and peripheral devices 1825, such as cache, other memory, data storage and/or electronic display adapters. The memory 1810, storage unit 1815, interface 1820 and peripheral devices 1825 are in communication with the CPU 1805 through a communication bus (solid lines), such as a motherboard. The storage unit 1815 can be a data storage unit (or data repository) for storing data. The computer system 1801 can be operatively coupled to a computer network ("network") 1830 with the aid of the communication interface 1820. The network 1830 can be the Internet, an internet and/or extranet, or an intranet and/or extranet that is in communication with the Internet. The network 1830 in some cases is a telecommunication and/or data network. The network 1830 can include one or more computer servers, which can enable distributed computing, such as cloud computing. The network 1830, in some cases with the aid of the computer system 1801, can implement a peer-to-peer network, which may enable devices coupled to the computer system 1801 to behave as a client or a server.

The CPU 1805 can execute a sequence of machine-readable instructions, which can be embodied in a program or software. The instructions may be stored in a memory location, such as the memory 1810. The instructions can be directed to the CPU 1805, which can subsequently program or otherwise configure the CPU 1805 to implement methods of the present disclosure. Examples of operations performed by the CPU 1805 can include fetch, decode, execute, and writeback.

The CPU 1805 can be part of a circuit, such as an integrated circuit. One or more other components of the system 1801 can be included in the circuit. In some cases, the circuit is an application specific integrated circuit (ASIC).

The storage unit 1815 can store files, such as drivers, libraries and saved programs. The storage unit 1815 can store user data, e.g., user preferences and user programs. The computer system 1801 in some cases can include one or more additional data storage units that are external to the computer system 1801, such as located on a remote server that is in communication with the computer system 1801 through an intranet or the Internet.

The computer system 1801 can communicate with one or more remote computer systems through the network 1830. For instance, the computer system 1801 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1801 via the network 1830.

Methods as described herein can be implemented by way of machine (e.g., computer processor) executable code stored on an electronic storage location of the computer system 1801, such as, for example, on the memory 1810 or electronic storage unit 1815. The machine executable or machine readable code can be provided in the form of software. During use, the code can be executed by the processor 1805. In some cases, the code can be retrieved from the storage unit 1815 and stored on the memory 1810 for ready access by the processor 1805. In some situations, the electronic storage unit 1815 can be precluded, and machine-executable instructions are stored on memory 1810.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1801 can include or be in communication with an electronic display 1835 that comprises a user interface (UI) 1840 for providing, for example, fluid control options (e.g., fluid flow rate, timing of applying polymerization source (e.g., light), strength of magnetic of electric force field, strength and/or frequency of pressure pulses, etc.). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1805. The algorithm can, for example, (i) sort occupied droplets from unoccupied droplets by including field-attractable particles in each droplet and applying a force field, (ii) sort occupied droplets from unoccupied droplets by applying a pressure pulse, (iii) sort occupied particles (e.g., cell beads) from unoccupied particles using field-attractable particles by applying a force field, (iv) sort occupied particles (e.g., cell beads) from unoccupied particles by applying a pressure pulse, (v) selectively polymerize occupied droplets, and/or (vi) selectively polymerize appropriately sized droplets. The algorithm can also, for example, generate a plurality of droplets that may or may not contain biological particles (cells) and/or barcode carrying beads (particles).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for sorting droplets, comprising:
   (a) bringing a first phase in contact with a second phase immiscible with said first phase, to generate a plurality of droplets, wherein said plurality of droplets comprises (i) a first subset of droplets each including, and not more than, one biological particle, and (ii) a second subset of droplets each either having more than one biological particle or not having any biological particle, wherein said biological particle is a cell, a derivative of a cell, or a constituent of a cell; wherein each of said plurality of droplets comprises field-attractable particles; and wherein a concentration of said field-attractable particles in droplets of said second subset not having any biological particle is substantially uniform;
   (b) directing said plurality of droplets along a first channel towards an intersection of said first channel with at least a second channel and a third channel; and
   (c) subjecting said plurality of droplets to an electric or magnetic field under conditions sufficient to separate said at least said portion of said first subset from said at least said portion of said second subset, thereby separating at least a portion of said first subset of said plurality of droplets from at least a portion of said second subset of said plurality of droplets, wherein upon separation, said at least said portion of said first subset of said plurality of droplets flows along said second channel and said at least said portion of said second subset of said plurality of droplets flows along said third channel.

2. The method of claim 1, wherein said first subset of said plurality of droplets includes particles having coupled thereto molecules comprising barcode sequences.

3. The method of claim 2, wherein said particles are gel beads.

4. The method of claim 1, further comprising detecting individual droplets of said first subset of said plurality of droplets, and subjecting said individual droplets to a stimulus to facilitate polymerization in said biological particles upon detecting said individual droplets.

5. The method of claim 4 wherein said stimulus is applied prior to said intersection.

6. The method of claim 4, wherein said stimulus is applied subsequent to said intersection.

7. The method of claim 4, wherein said stimulus is an optical stimulus or chemical stimulus.

8. The method of claim 1, wherein said biological particles are cells enclosed within or comprising a gel or polymer matrix.

9. A method for sorting droplets, comprising:
   (a) bringing a first phase in contact with a second phase immiscible with said first phase, to generate a plurality of droplets, wherein said plurality of droplets comprises (i) a first subset of droplets each including, and not more than, one biological particle, and (ii) a second subset of droplets each either having more than one biological particle or not having any biological particle, wherein said biological particle is a cell, a derivative of a cell, or a constituent of a cell; wherein each of said plurality of droplets comprises field-attractable particles; and wherein each droplet of said first subset comprises (i) less field attractable particles than each droplet of said second subset not having any biological particle, and (ii) more field attractable particles than each droplet of said second subset having more than one biological particle;
   (b) directing said plurality of droplets along a first channel towards an intersection of said first channel with at least a second channel and a third channel; and
   (c) subjecting said plurality of droplets to an electric or magnetic field under conditions sufficient to separate said at least said portion of said first subset from said at least said portion of said second subset, thereby separating at least a portion of said first subset of said plurality of droplets from at least a portion of said second subset of said plurality of droplets, wherein upon separation, said at least said portion of said first subset of said plurality of droplets flows along said second channel and said at least said portion of said second subset of said plurality of droplets flows along said third channel.

10. The method of claim 9, wherein forces induced by said electric or magnetic field on droplets of said second subset not having any biological particle are greater than forces induced on said first subset, and wherein forces induced on said first subset are greater than forces induced on droplets of said second subset having more than one biological particle.

11. The method of claim 1, wherein said field-attractable particles are magnetic-field attractable particles.

12. A method for sorting droplets, comprising:
(a) bringing a first phase in contact with a second phase immiscible with said first phase, to generate a plurality of droplets, wherein said plurality of droplets comprises (i) a first subset of droplets each including, and not more than, one biological particle, and (ii) a second subset of droplets each either having more than one biological particle or not having any biological particle, wherein said biological particle is a cell, a derivative of a cell, or a constituent of a cell; and wherein each of said plurality of droplets comprises field-attractable particles,
(b) directing said plurality of droplets along a first channel towards an intersection of said first channel with at least a second channel and a third channel; and
(c) subjecting said plurality of droplets to an electric or magnetic field under conditions sufficient to separate said at least said portion of said first subset from said at least said portion of said second subset, thereby separating at least a portion of said first subset of said plurality of droplets from at least a portion of said second subset of said plurality of droplets, wherein upon separation, said at least said portion of said first subset of said plurality of droplets flows along said second channel and said at least said portion of said second subset of said plurality of droplets flows along said third channel; wherein said conditions of said electric or magnetic field sufficient to separate said at least said portion of said first subset and said at least said portion of said second subset are determined based at least in part on a ratio between sizes of said plurality of droplets and sizes of said biological particles in said first subset of said plurality of droplets.

13. The method of claim 1, further comprising, subsequent to (c), subjecting nucleic acid molecules derived from said biological particles in said first subset to nucleic acid sequencing.

14. The method of claim 13, further comprising, subsequent to (c), subjecting said first subset of said plurality of droplets to conditions sufficient to yield extension products of said nucleic acid molecules from said biological particles in said first subset, and subjecting said extension products or derivatives thereof to nucleic acid sequencing.

15. The method of claim 1, wherein upon separation, said at least said portion of said first subset and droplets of said second subset having more than one biological particle flow along said second channel and droplets of said second subset not having any biological particle flow along said third channel.

16. A method for sorting droplets, comprising:
(a) bringing a first phase in contact with a second phase immiscible with said first phase, to generate a plurality of droplets, wherein said plurality of droplets comprises (i) a first subset of droplets each including, and not more than, one biological particle, and (ii) a second subset of droplets each either having more than one biological particle or not having any biological particle, wherein said biological particle is a cell, a derivative of a cell, or a constituent of a cell;
(b) directing said plurality of droplets along a first channel towards an intersection of said first channel with at least a second channel and a third channel; and
(c) separating at least a portion of said first subset of said plurality of droplets from at least a portion of said second subset of said plurality of droplets, wherein upon separation, said at least said portion of said first subset and said second subset having more than one biological particle flow along said second channel and droplets of said second subset not having any biological particle flow along said third channel;
(d) directing said at least said portion of said first subset and said droplets of said second subset having more than one biological particle along said second channel towards a second intersection of said second channel with at least a fourth channel and a fifth channel; and
(e) separating said at least said portion of said first subset from at least a portion of said droplets of said second subset having more than one biological particle, wherein upon separation, said at least said portion of said first subset flows along said fourth channel and said at least said portion of said droplets of said second subset having more than one biological particle flows along said fifth channel.

17. The method of claim 9, wherein said first subset of said plurality of droplets includes particles having coupled thereto molecules comprising barcode sequences.

18. The method of claim 17, wherein said particles are gel beads.

19. The method of claim 9, wherein said biological particles are cells enclosed within or comprising a gel or polymer matrix.

20. The method of claim 9, further comprising, subsequent to (c), subjecting nucleic acid molecules derived from said biological particles in said first subset to nucleic acid sequencing.

21. The method of claim 12, wherein said first subset of said plurality of droplets includes particles having coupled thereto molecules comprising barcode sequences.

22. The method of claim 21, wherein said particles are gel beads.

23. The method of claim 12, wherein said biological particles are cells enclosed within or comprising a gel or polymer matrix.

24. The method of claim 12, further comprising, subsequent to (c), subjecting nucleic acid molecules derived from said biological particles in said first subset to nucleic acid sequencing.

25. The method of claim 16, wherein said first subset of said plurality of droplets includes particles having coupled thereto molecules comprising barcode sequences.

26. The method of claim 25, wherein said particles are gel beads.

27. The method of claim 16, wherein said biological particles are cells enclosed within or comprising a gel or polymer matrix.

28. The method of claim 16, further comprising, subsequent to (c), subjecting nucleic acid molecules derived from said biological particles in said first subset to nucleic acid sequencing.

29. The method of claim 16, wherein (c) comprises subjecting said plurality of droplets to a pressure pulse under conditions sufficient to separate said at least said portion of said first subset from said at least said portion of said second subset.

30. The method of claim 29, wherein forces induced by said pressure pulse on droplets of said second subset not having any biological particle are greater than forces induced on said first subset, and wherein forces induced on said first subset are greater than forces induced on droplets of said second subset having more than one biological particle.

* * * * *